US011933781B2

(12) United States Patent
Schwartz et al.

(10) Patent No.: US 11,933,781 B2
(45) Date of Patent: Mar. 19, 2024

(54) FIBROSIS MODEL AND METHODS OF USE THEREOF

(71) Applicant: The Regents of the University of Colorado, Aurora, CO (US)

(72) Inventors: David Schwartz, Denver, CO (US); Ian Stancil, Denver, CO (US)

(73) Assignee: THE REGENTS OF THE UNIVERSITY OF COLORADO, Aurora, CO (US)

( * ) Notice: Subject to any disclaimer, the term of this patent is extended or adjusted under 35 U.S.C. 154(b) by 201 days.

(21) Appl. No.: 17/546,554

(22) Filed: Dec. 9, 2021

(65) Prior Publication Data

US 2022/0178912 A1 Jun. 9, 2022

Related U.S. Application Data

(60) Provisional application No. 63/123,246, filed on Dec. 9, 2020.

(51) Int. Cl.
*C12Q 1/00* (2006.01)
*G01N 33/50* (2006.01)

(52) U.S. Cl.
CPC ..... *G01N 33/5029* (2013.01); *G01N 33/5044* (2013.01)

(58) Field of Classification Search
CPC .................................................. G01N 33/5029
See application file for complete search history.

(56) References Cited

U.S. PATENT DOCUMENTS

| | | |
|---|---|---|
| 2004/0210040 A1 | 10/2004 | Landolfi et al. |
| 2006/0246448 A1 | 11/2006 | Ullrich et al. |
| 2017/0130231 A1 | 5/2017 | Chae et al. |
| 2018/0327488 A1 | 11/2018 | Yarden et al. |

OTHER PUBLICATIONS

Park, J.A. et al., "Compressive Stress Causes an Unjamming Transition and an Epithelial-Mesenchymal Transition in the Airway Epithelium in Asthma"; AnnalsATS vol. 13, Supplement 1, Mar. 2016 p. S102.

*Primary Examiner* — Albert M Navarro
(74) *Attorney, Agent, or Firm* — CANTOR COLBURN LLP

(57) ABSTRACT

A method of screening a test compound, e.g., a fibrosis or IPF inhibitor, for induction of an unjammed-to-jammed transition (UJT) in fibrotic primary human bronchial epithelial cells (HBECs) isolated from a subject with a fibrotic lung disease includes culturing the fibrotic primary HBECs at an air-liquid interface for a time sufficient to provide a differentiated pseudostratified epithelium contacting the cultured cells with the test compound; and monitoring the motility of the cultured cells to identify the cultured cells as moving or stationary; wherein stationary cultured cells indicate that the test compound induces the UJT. Also included are methods of identifying lung fibrosis biomarkers.

10 Claims, 49 Drawing Sheets

Specification includes a Sequence Listing.

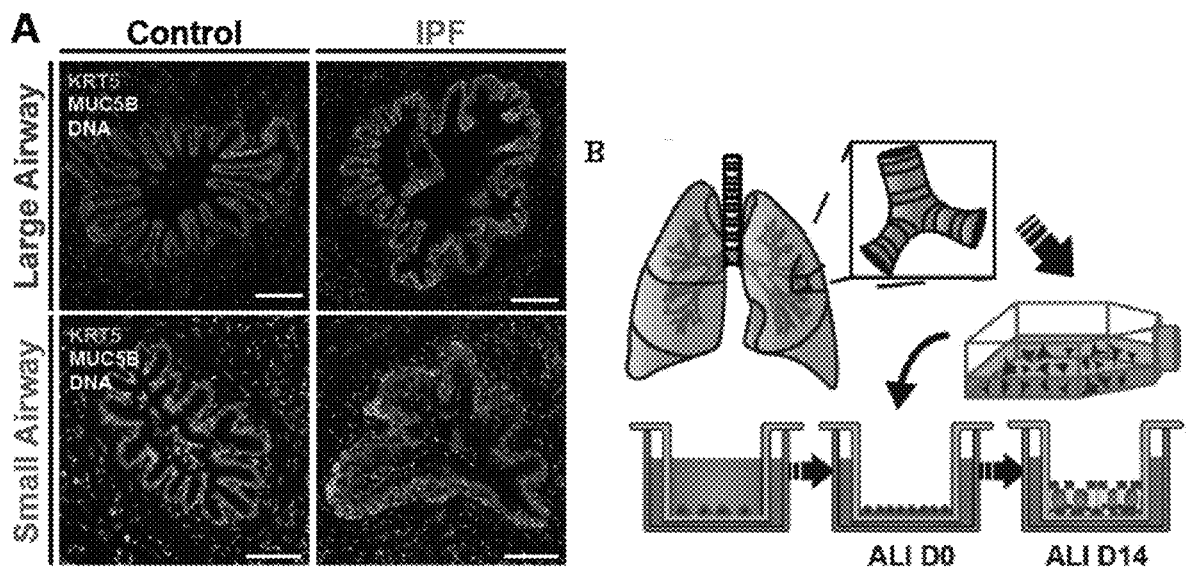
FIG. 1A-B
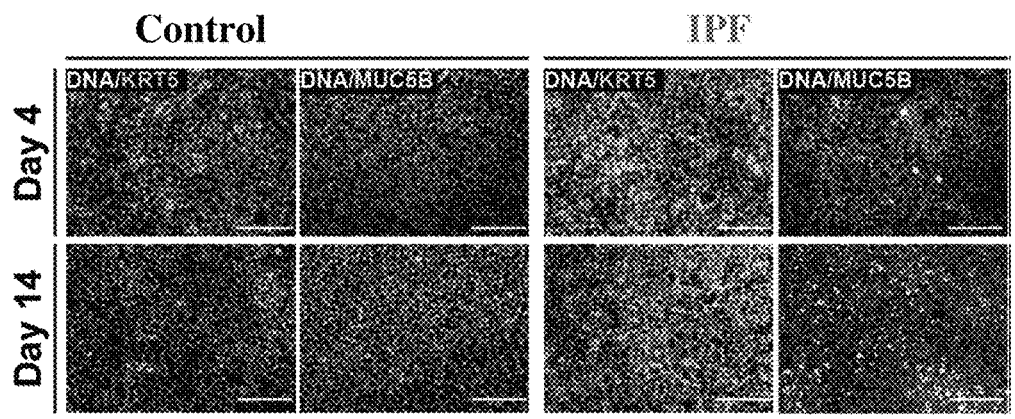
FIG. 1C
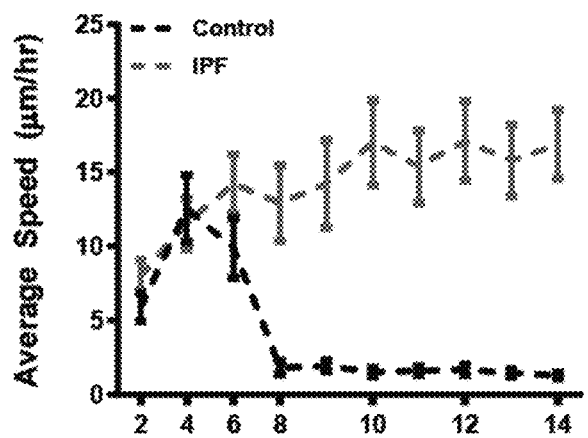
FIG. 1D

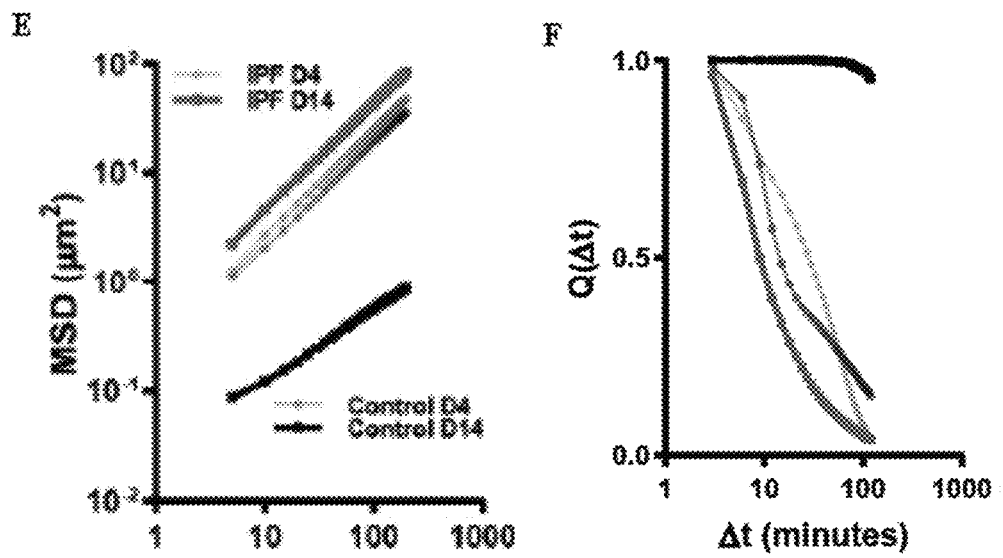
FIG. 1E-F
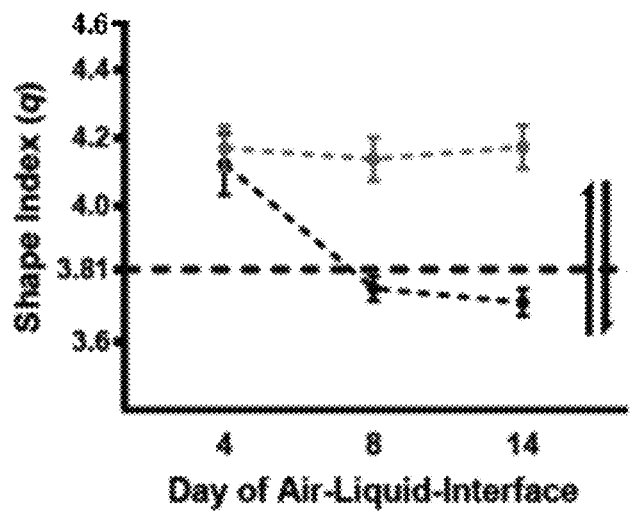
FIG. 1G

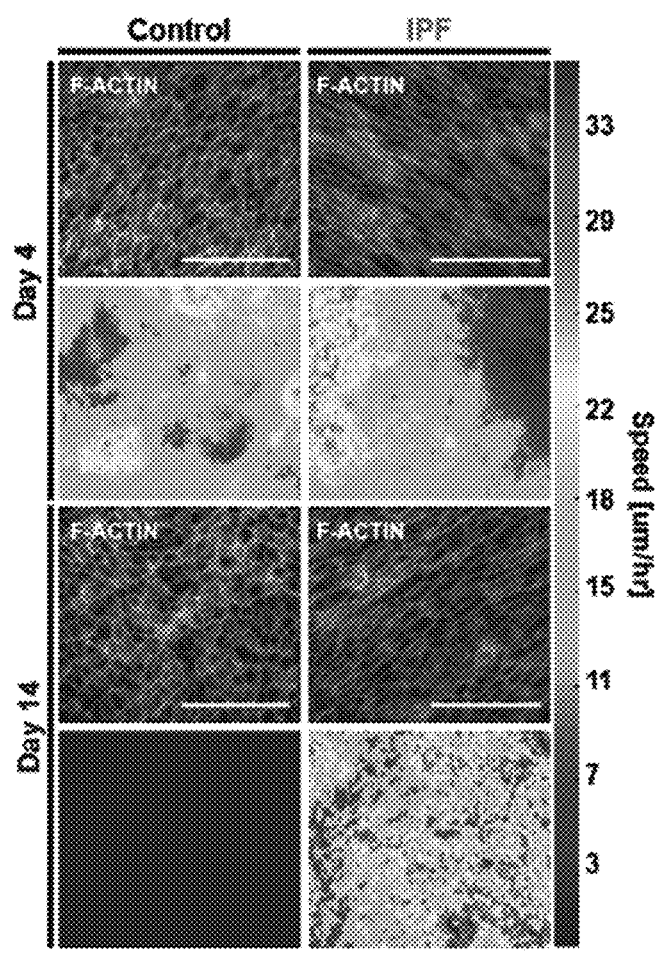
FIG. 1H
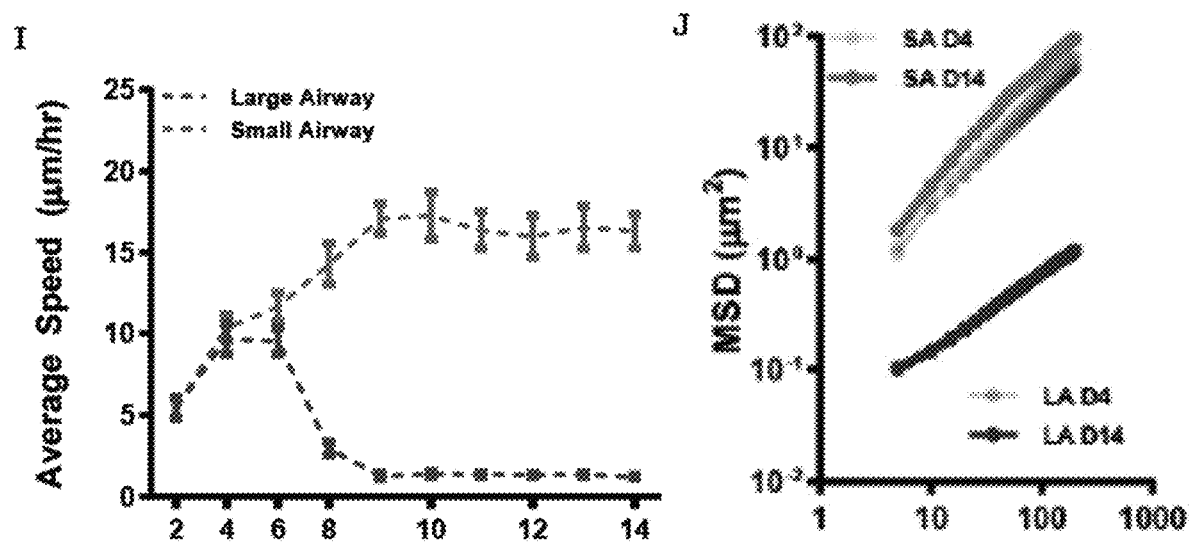
FIG. 1I-J

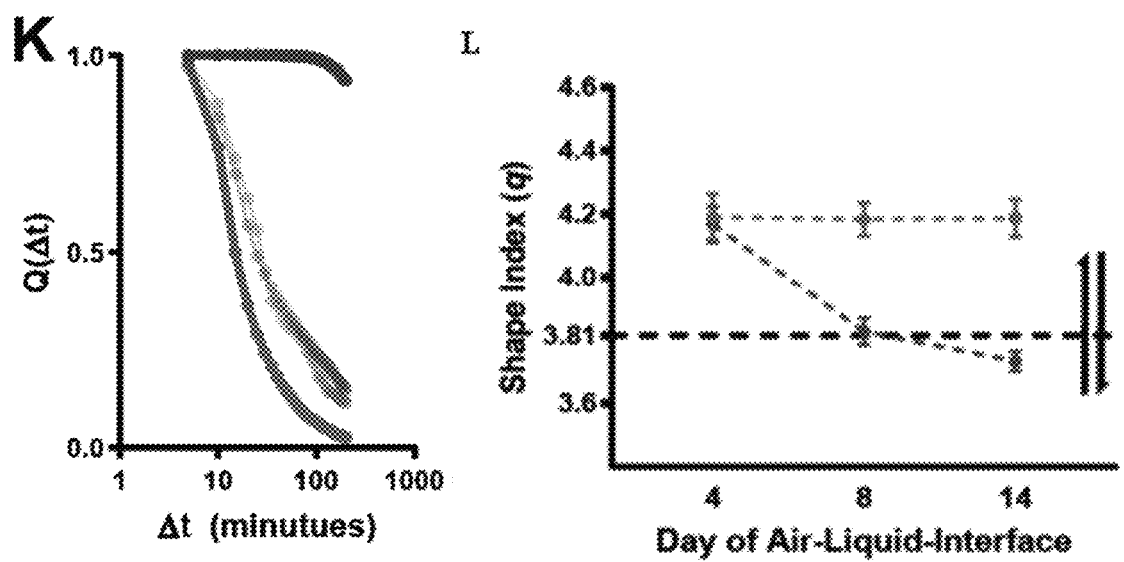
FIG. 1K-L
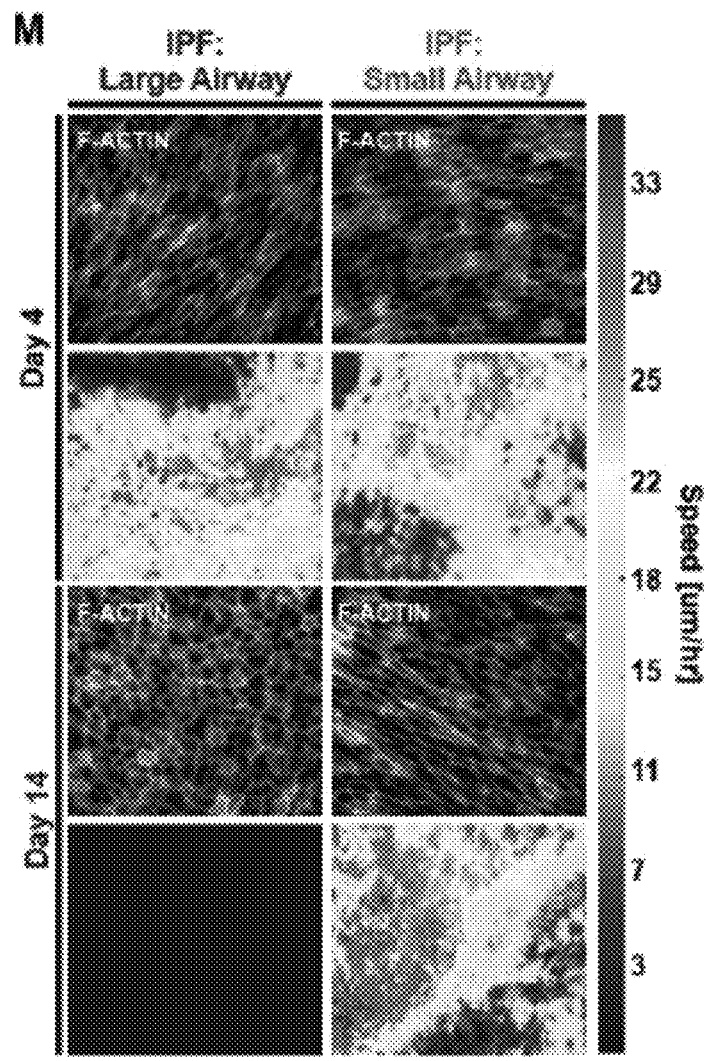
FIG. 1M

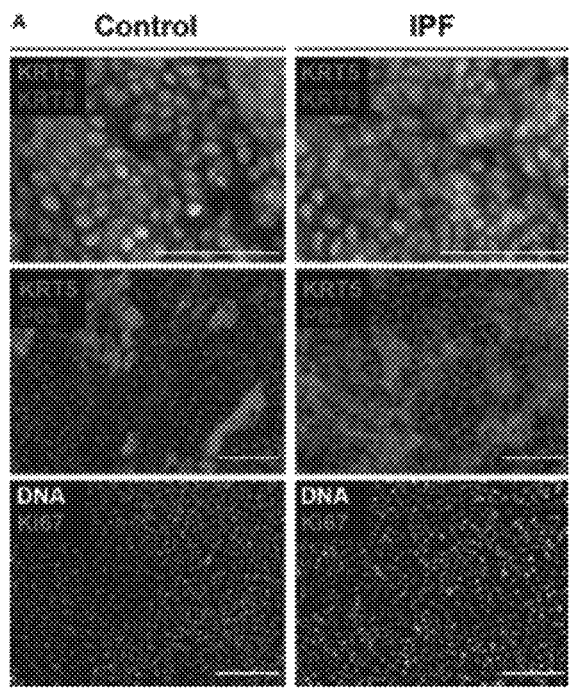
FIG. 2A
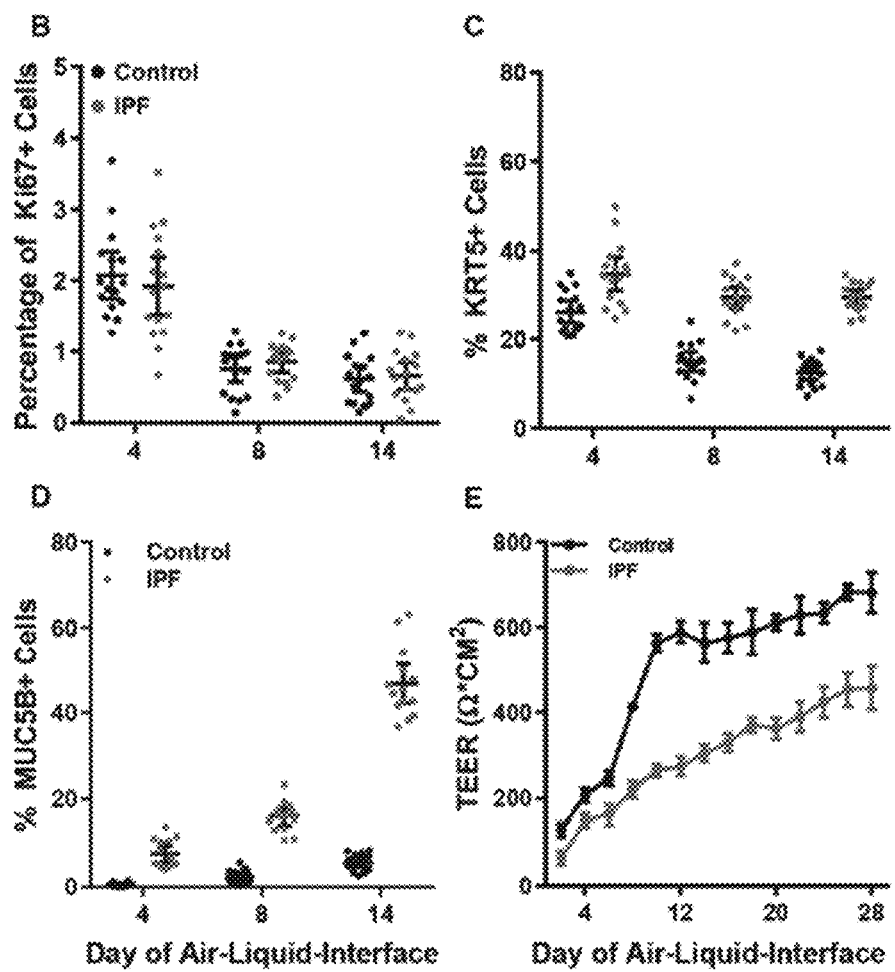
FIG. 2B-E

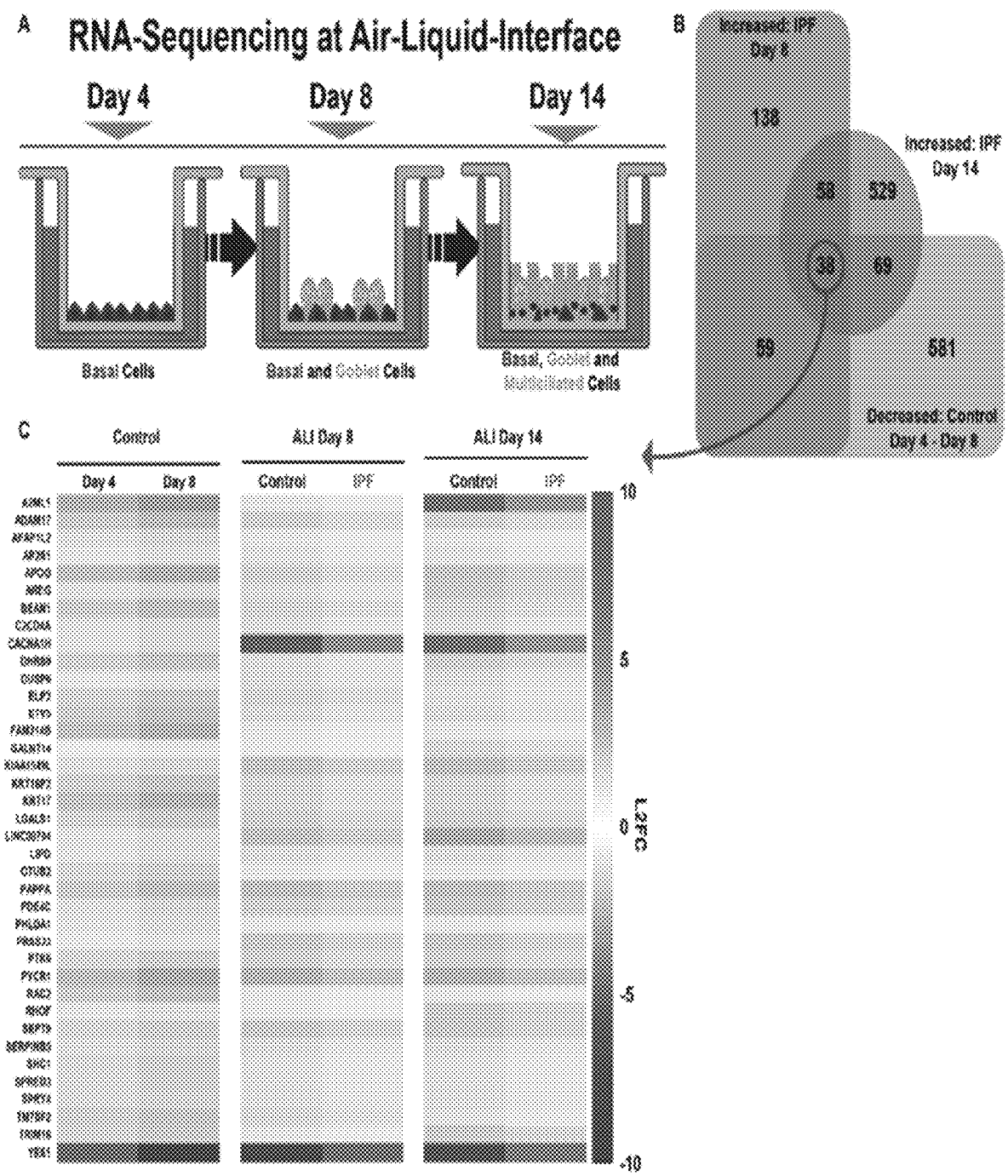
FIG. 3A-C

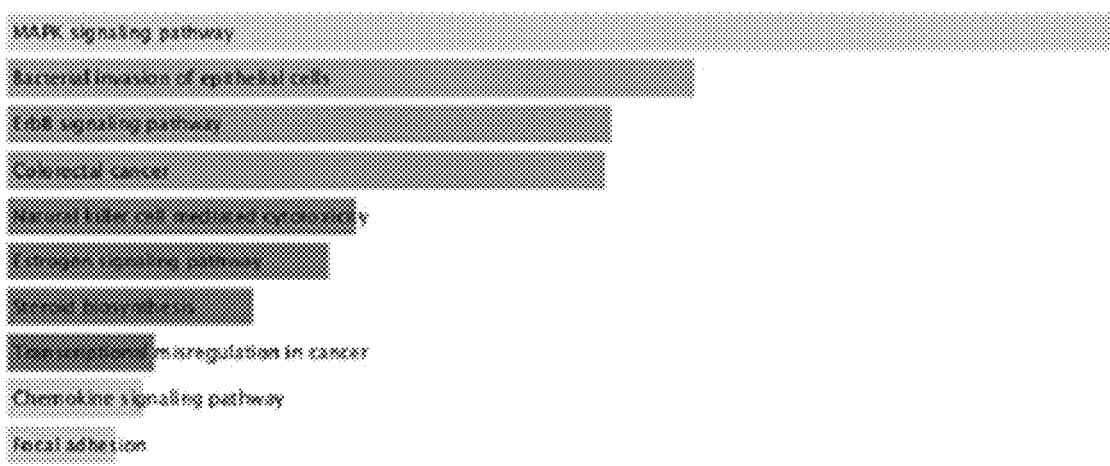
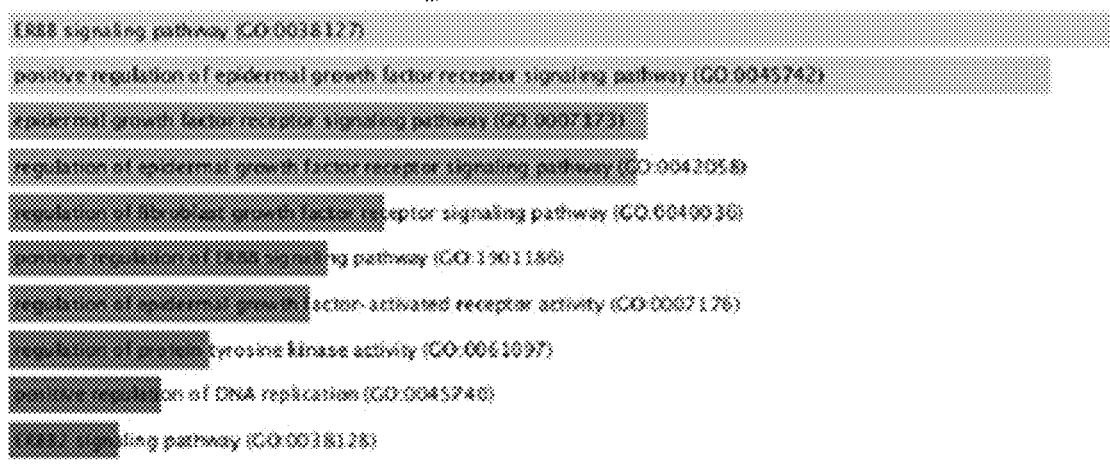
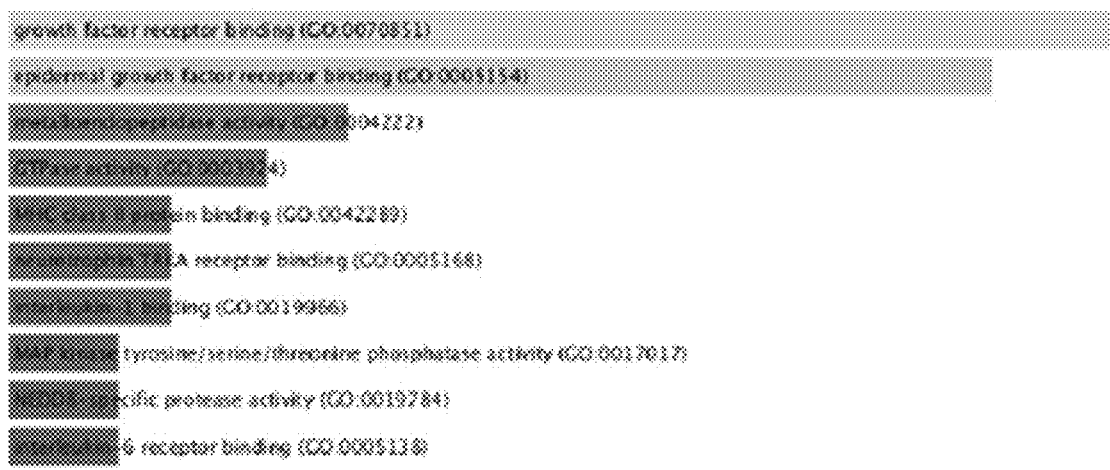
FIG. 3D

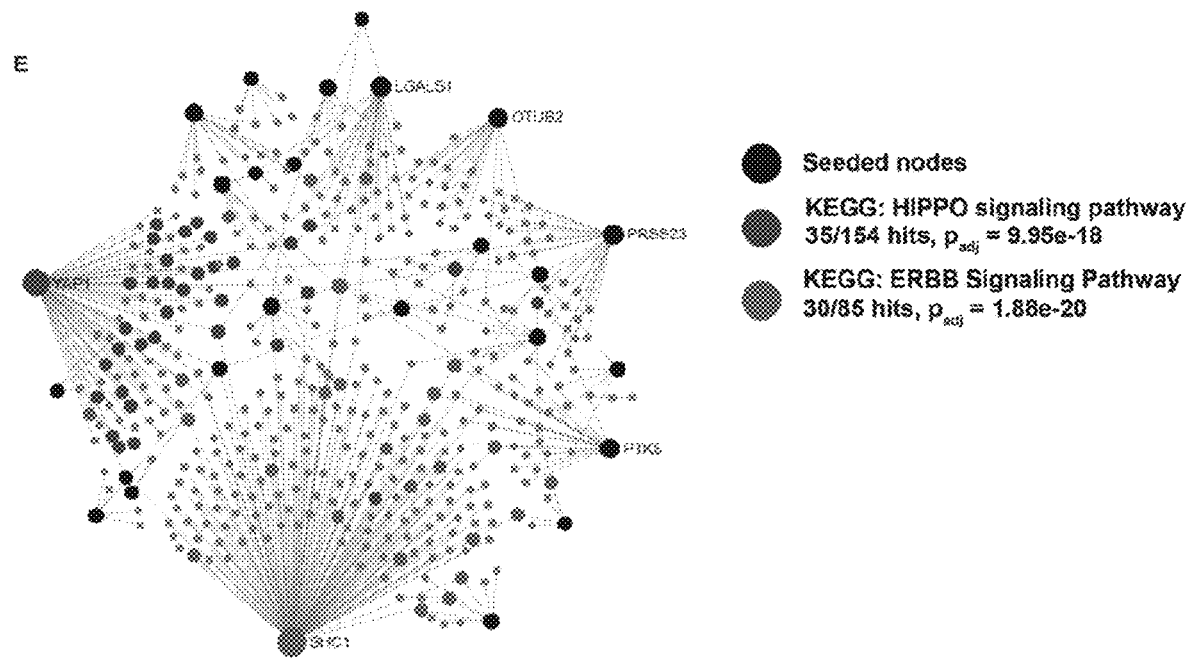
FIG. 3E
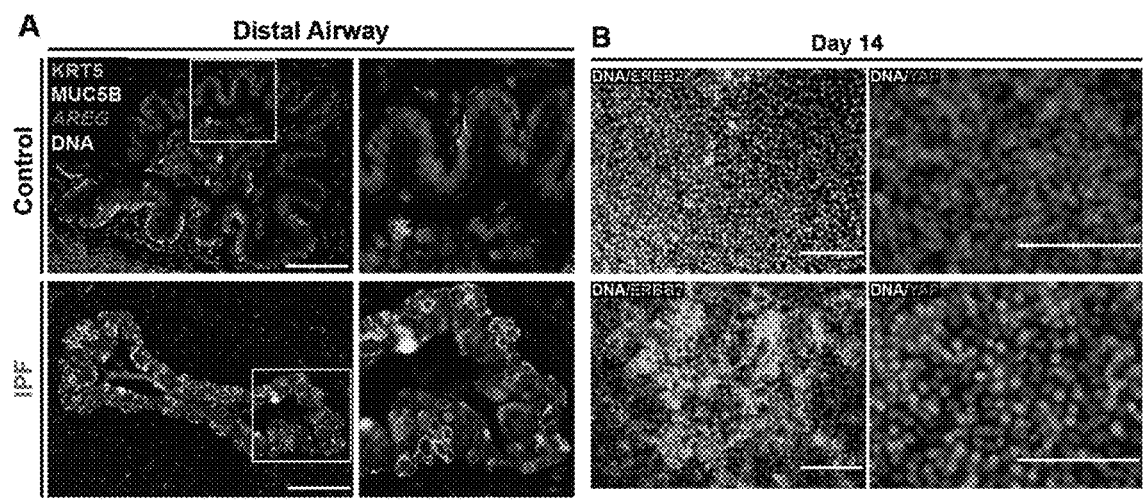
FIG. 4A-B

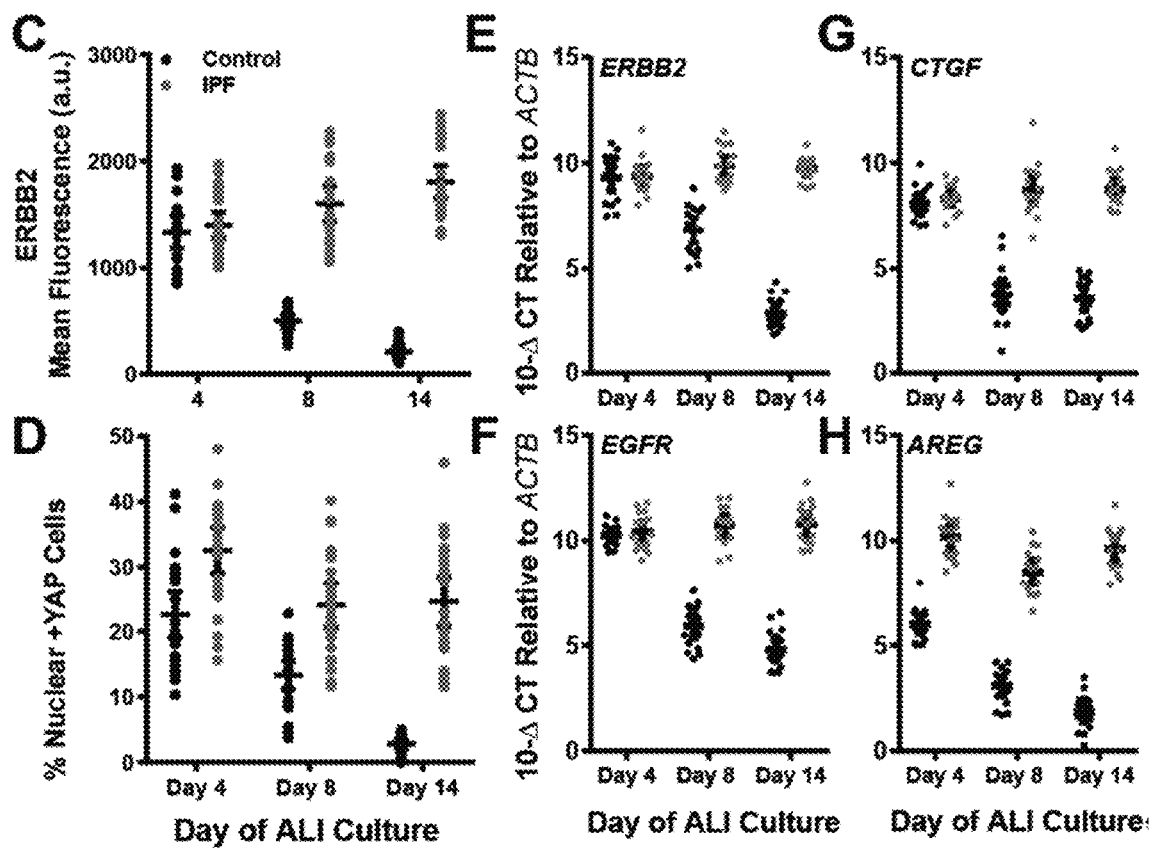
FIG. 4C-H
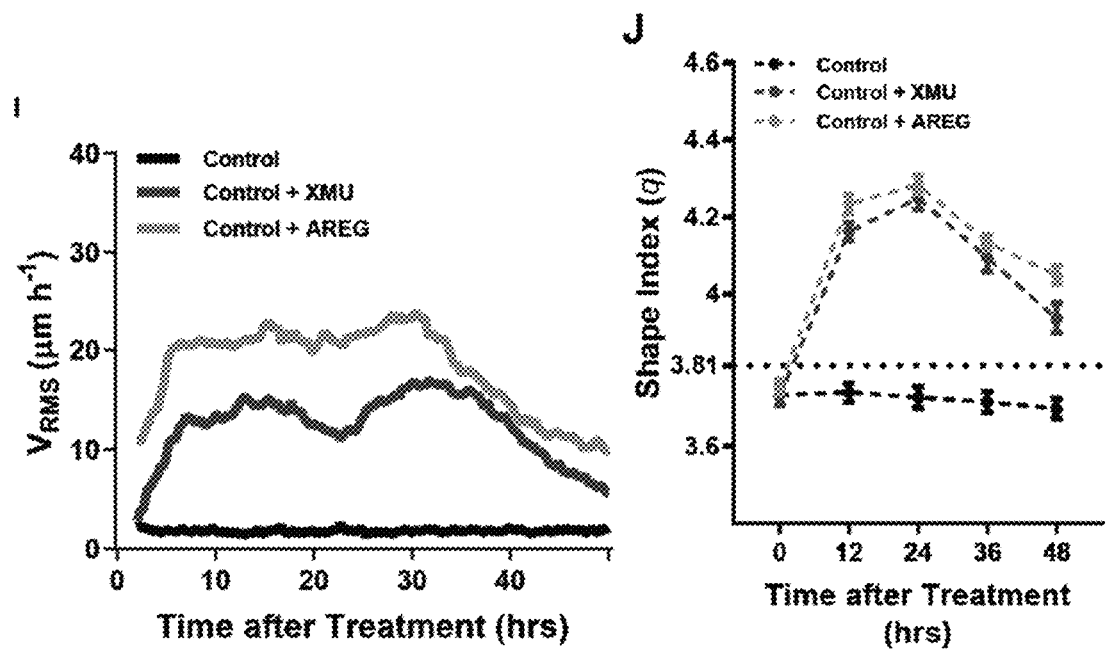
FIG. 4I-J

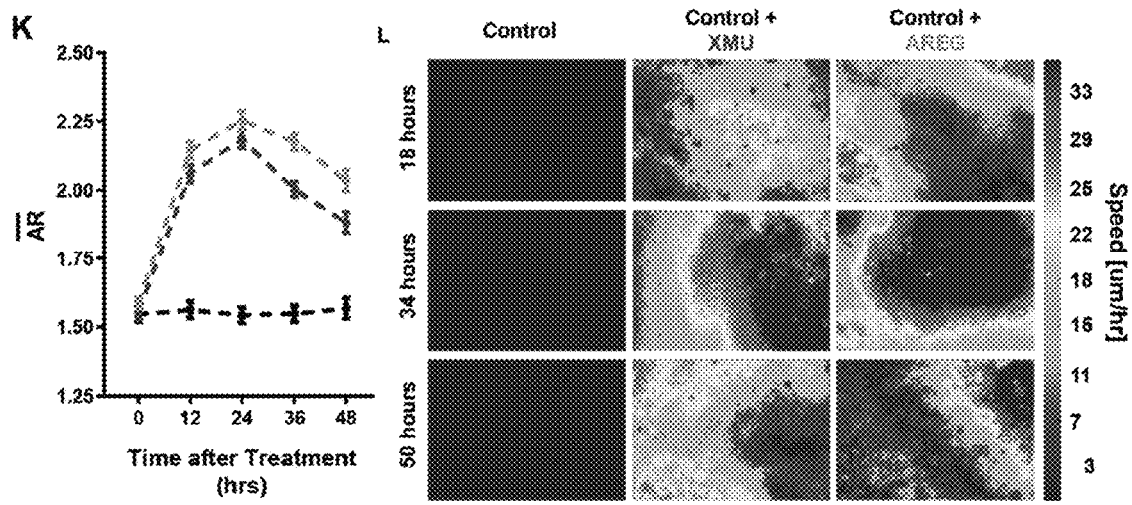
FIG. 4K-L
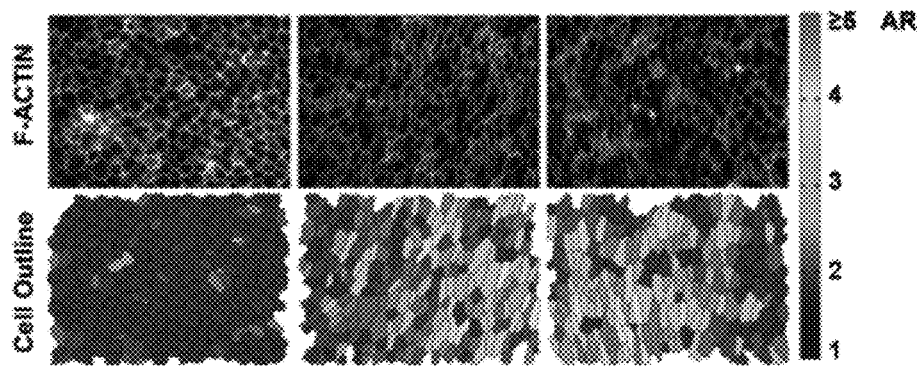
FIG. 4M
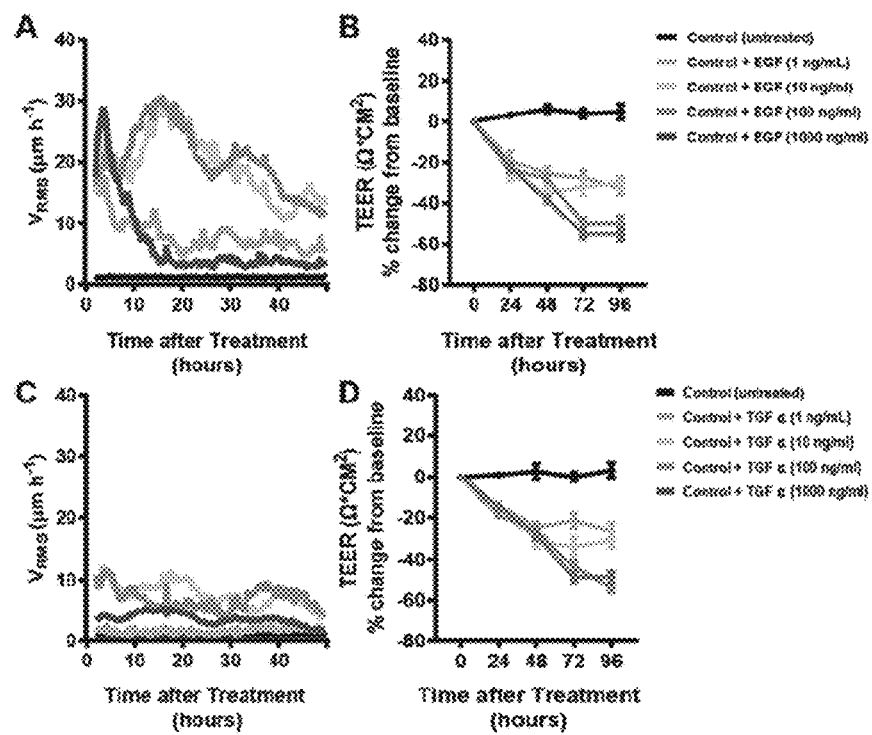
FIG. 5A-D

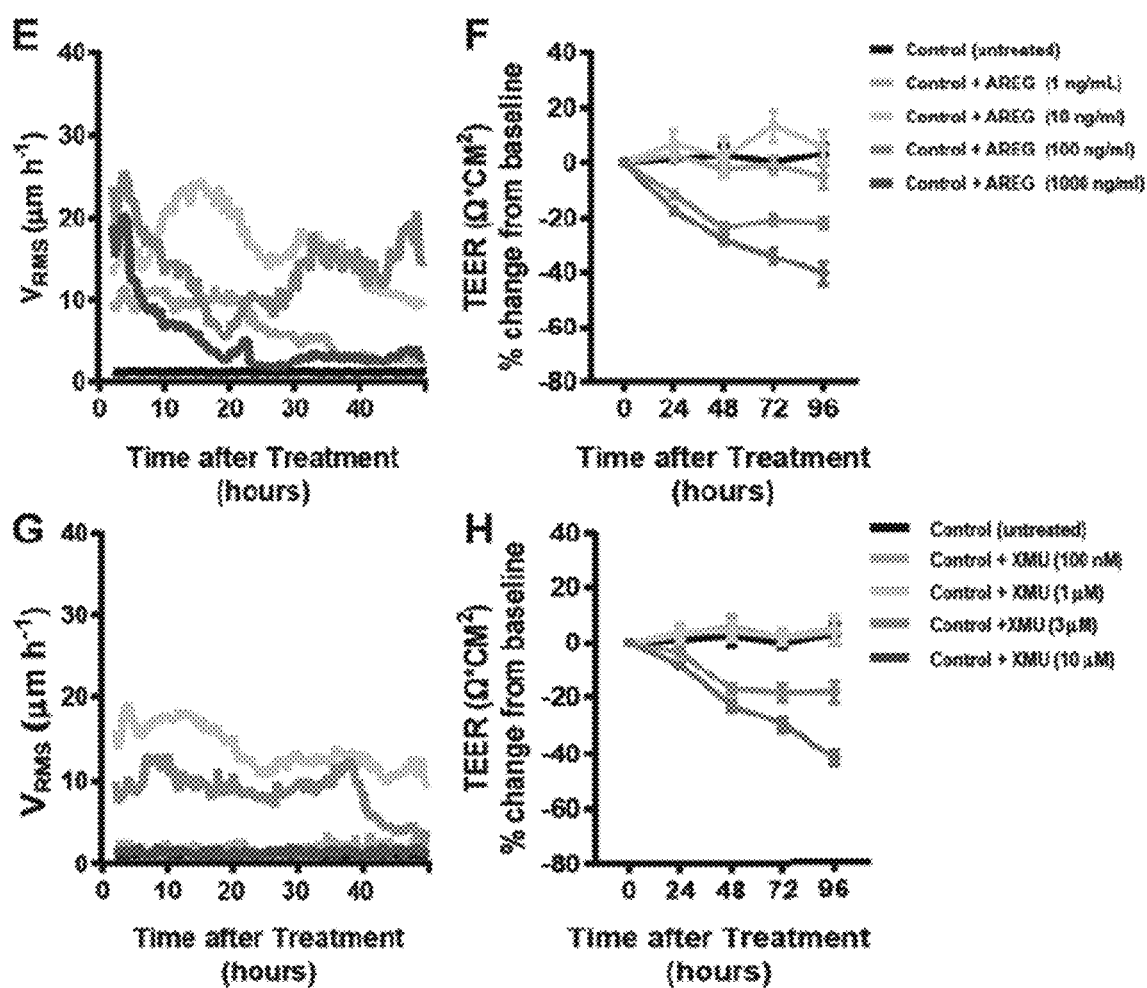
FIG. 5E-H

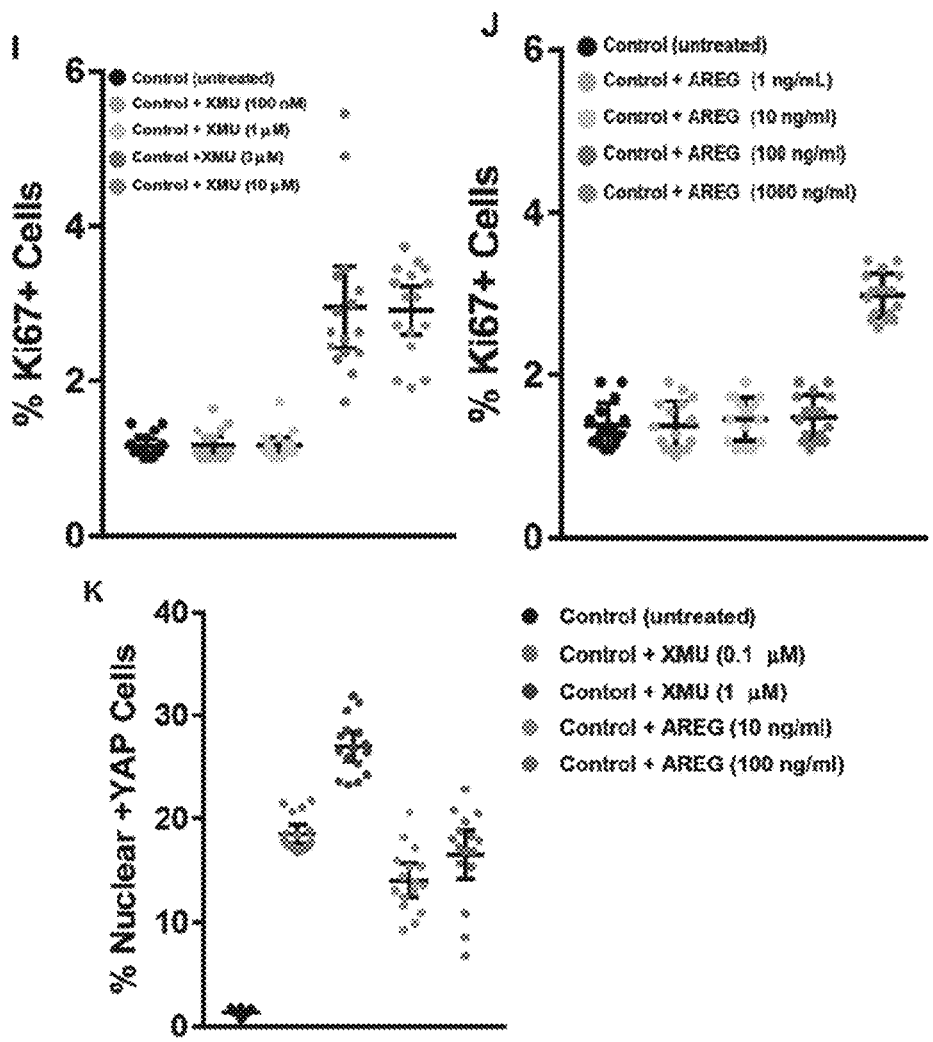
FIG. 5I-K
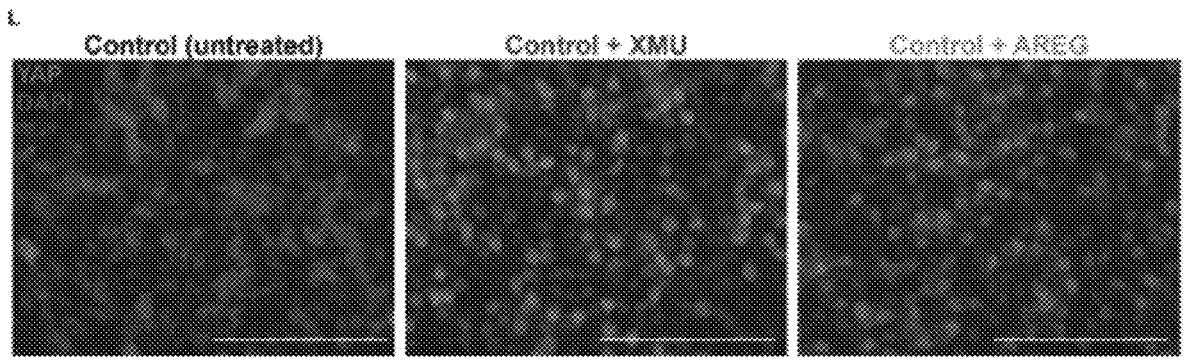
FIG. 5L

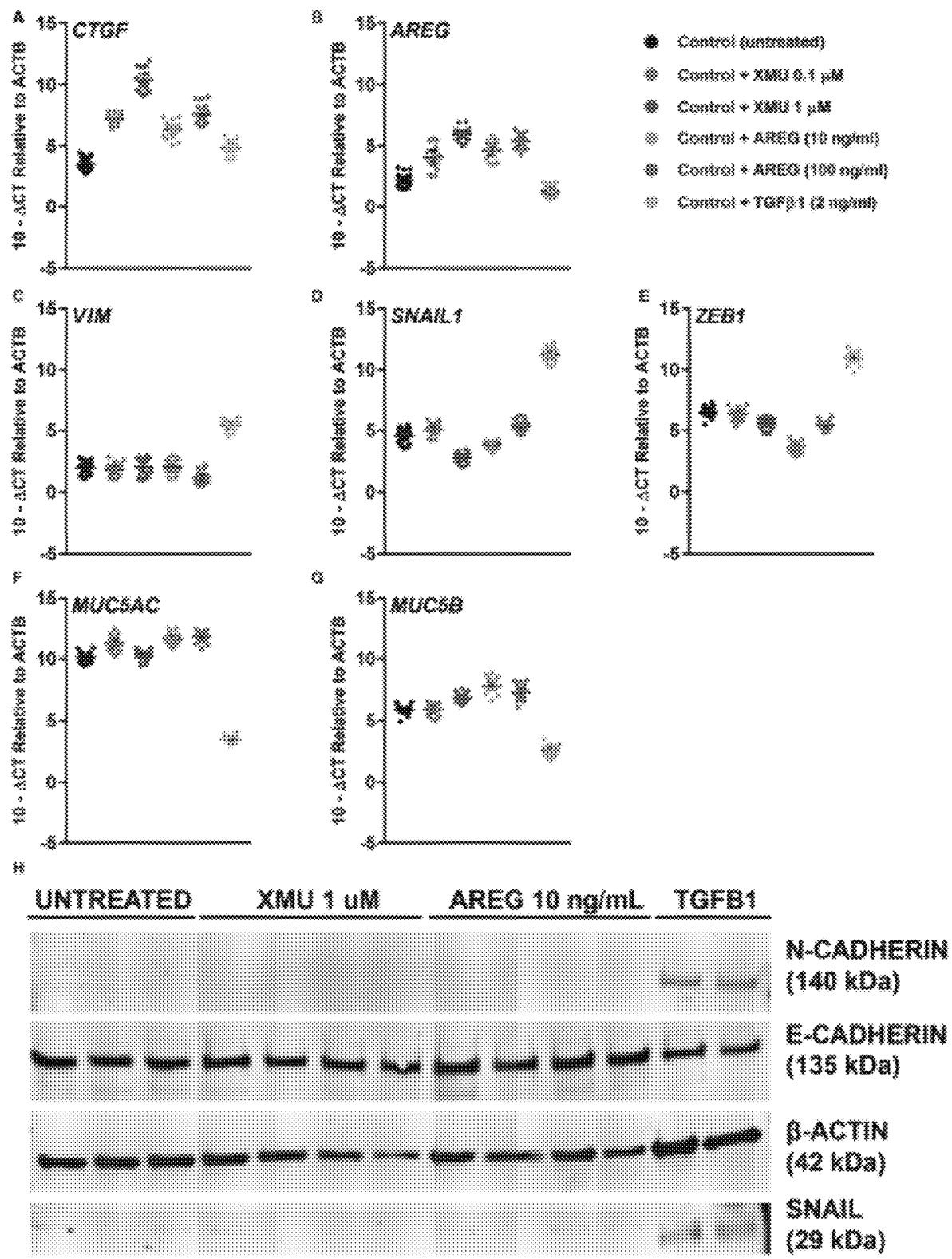
FIG. 6A-H

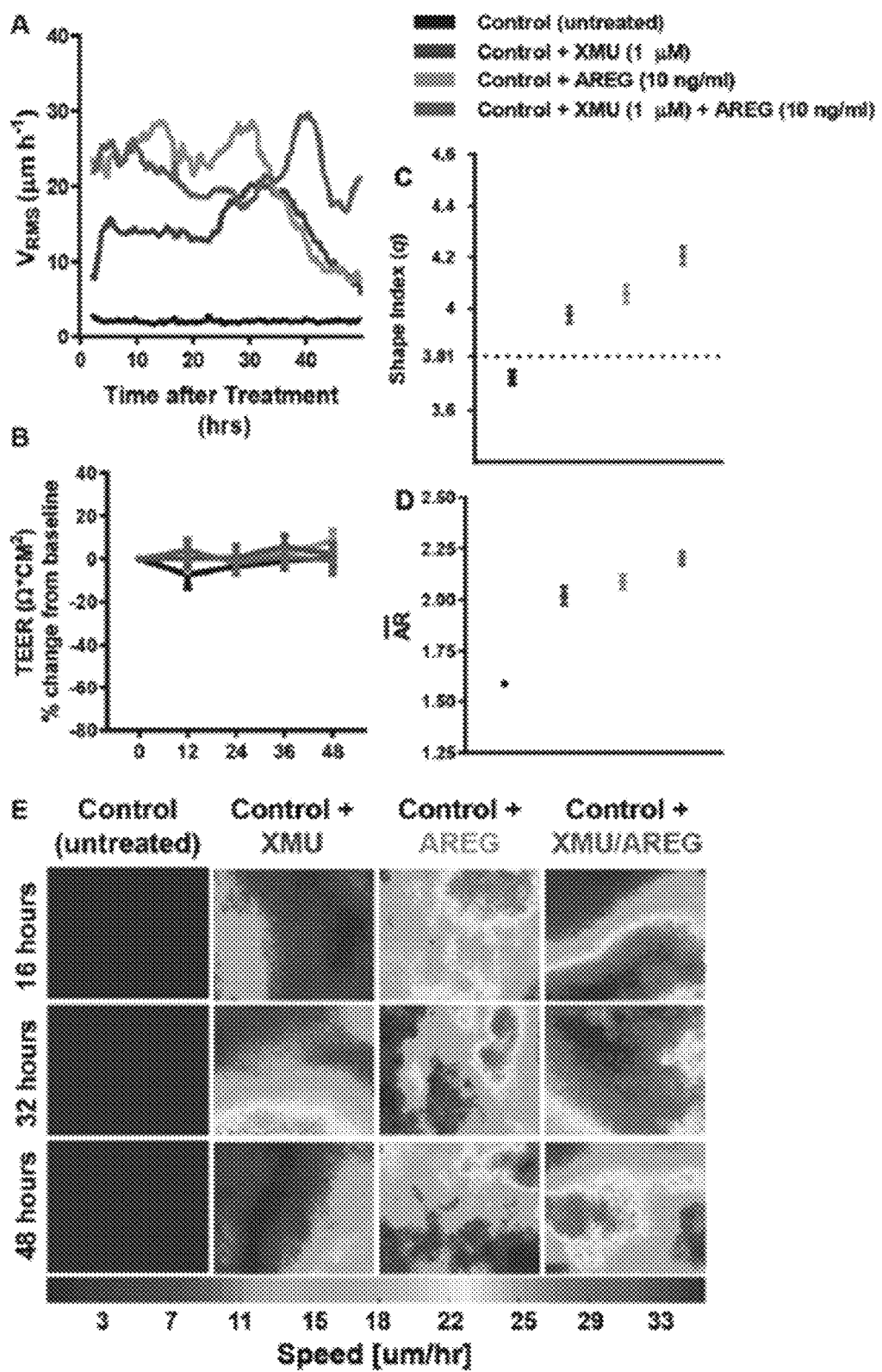
FIG. 7A-E

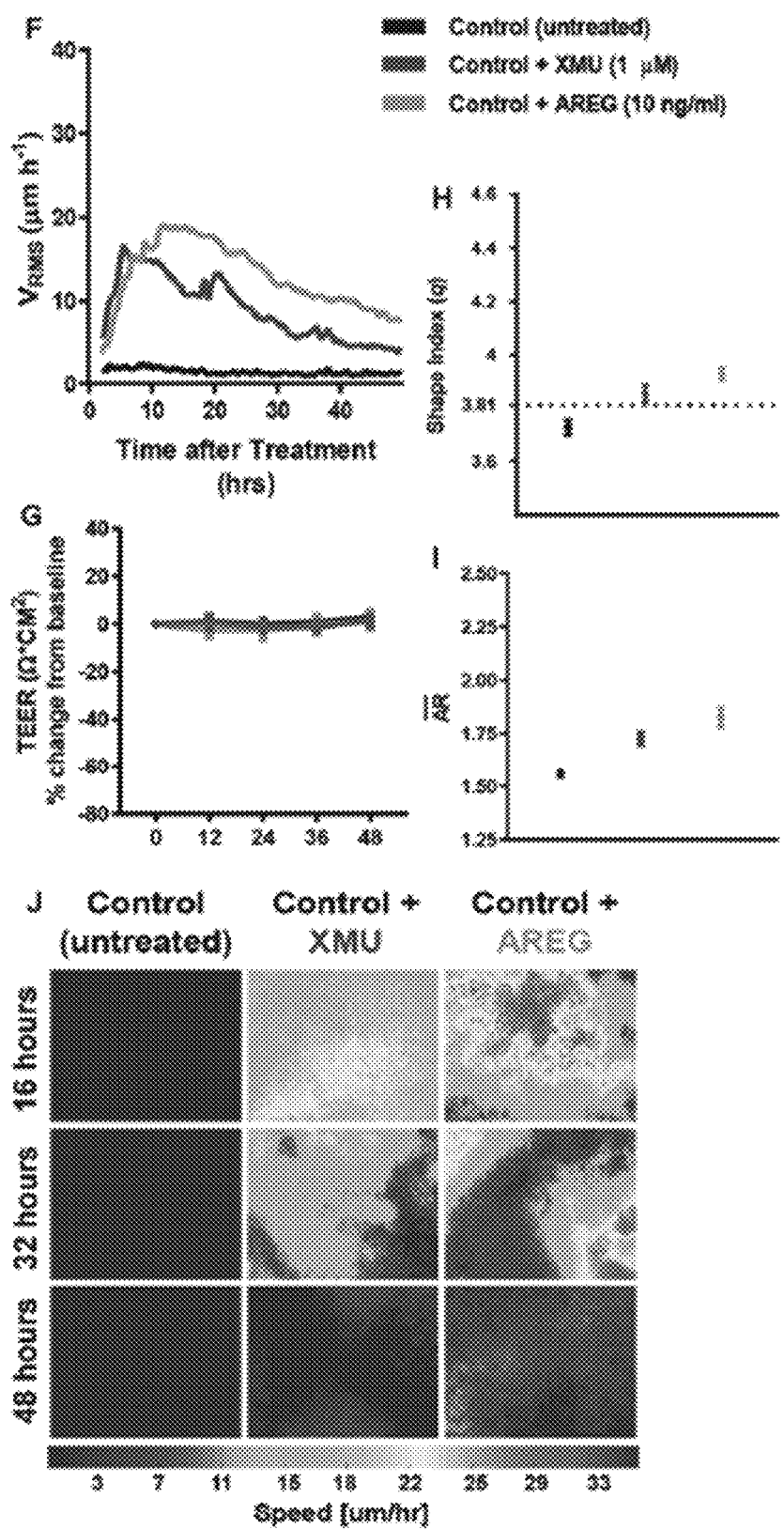
FIG. 7F-J

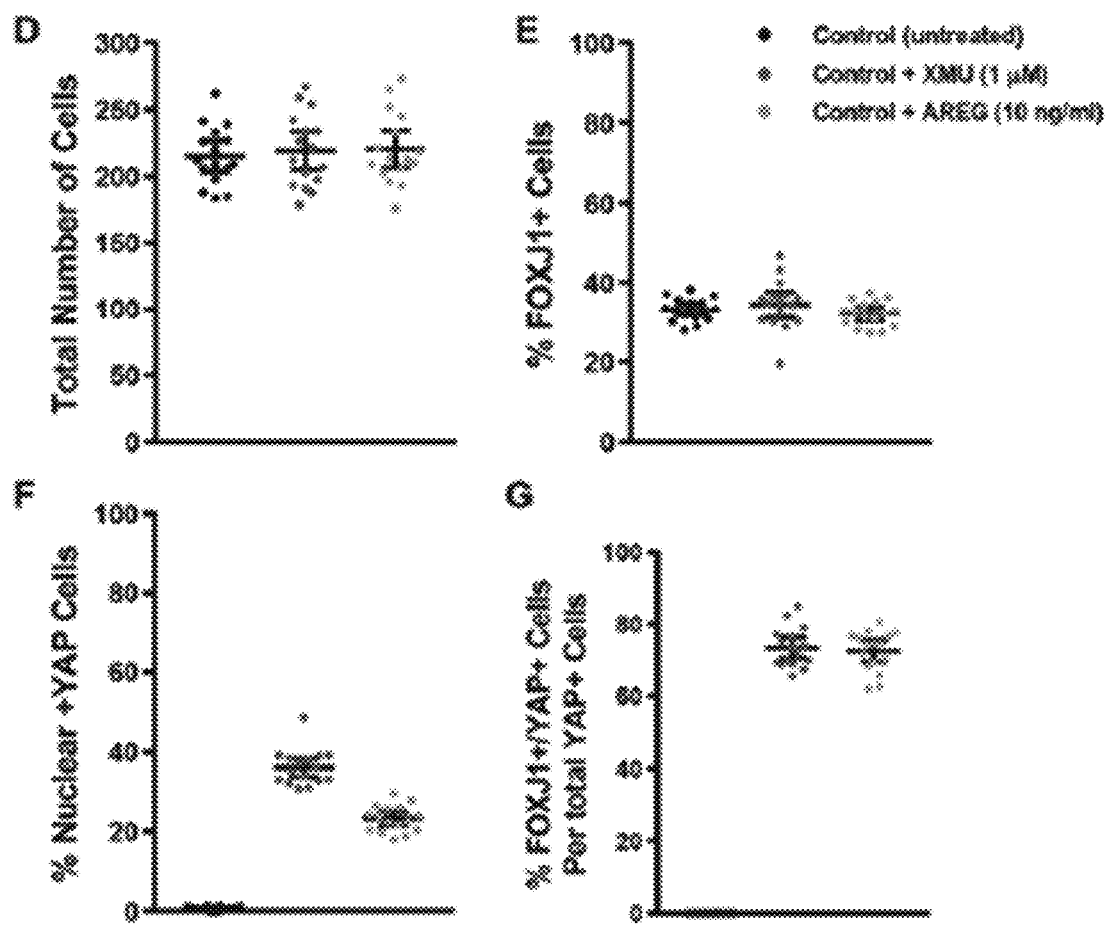
FIG. 8D-G
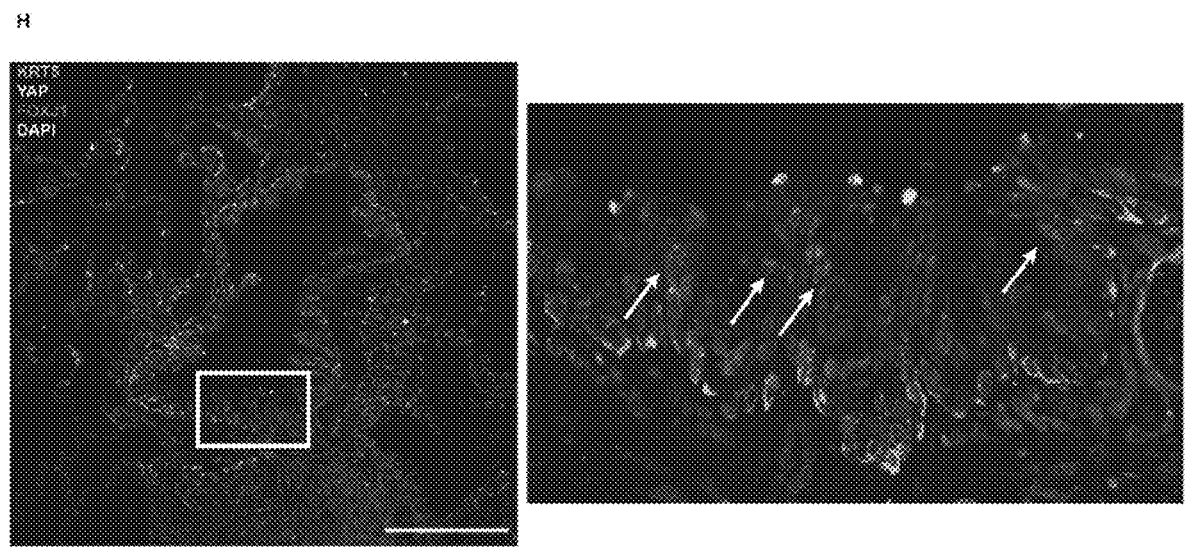
FIG. 8H

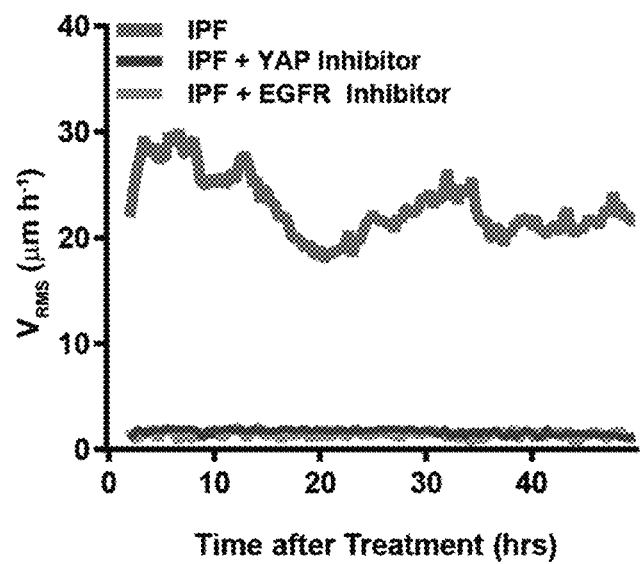
FIG. 9A
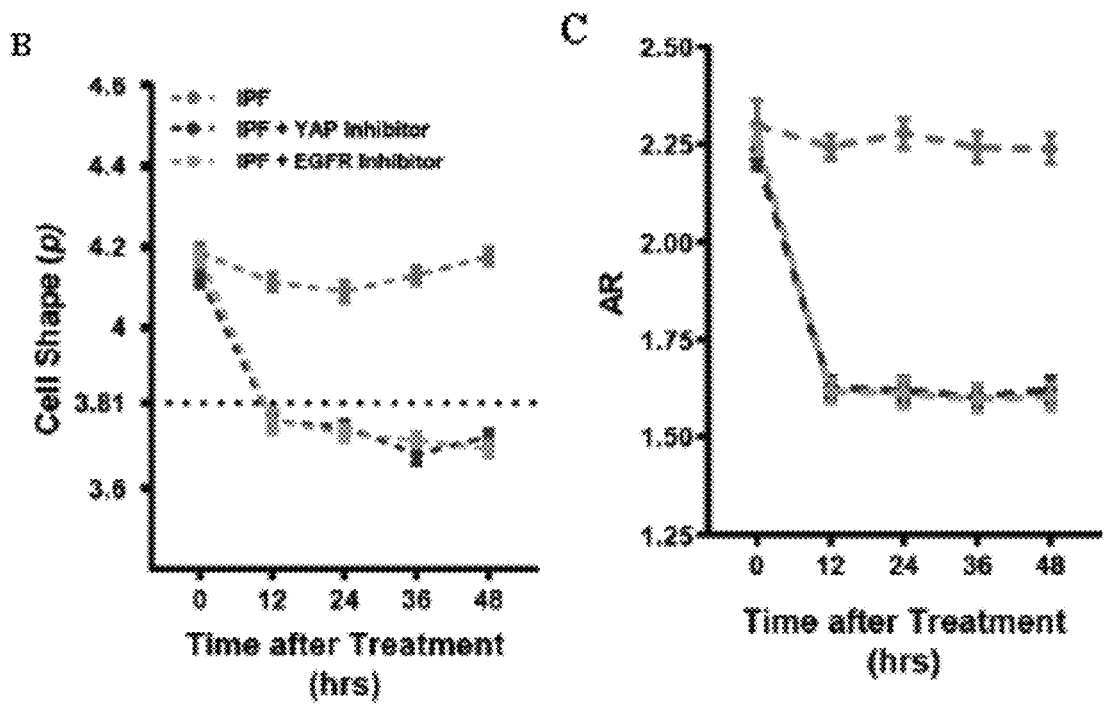
FIG. 9B-C

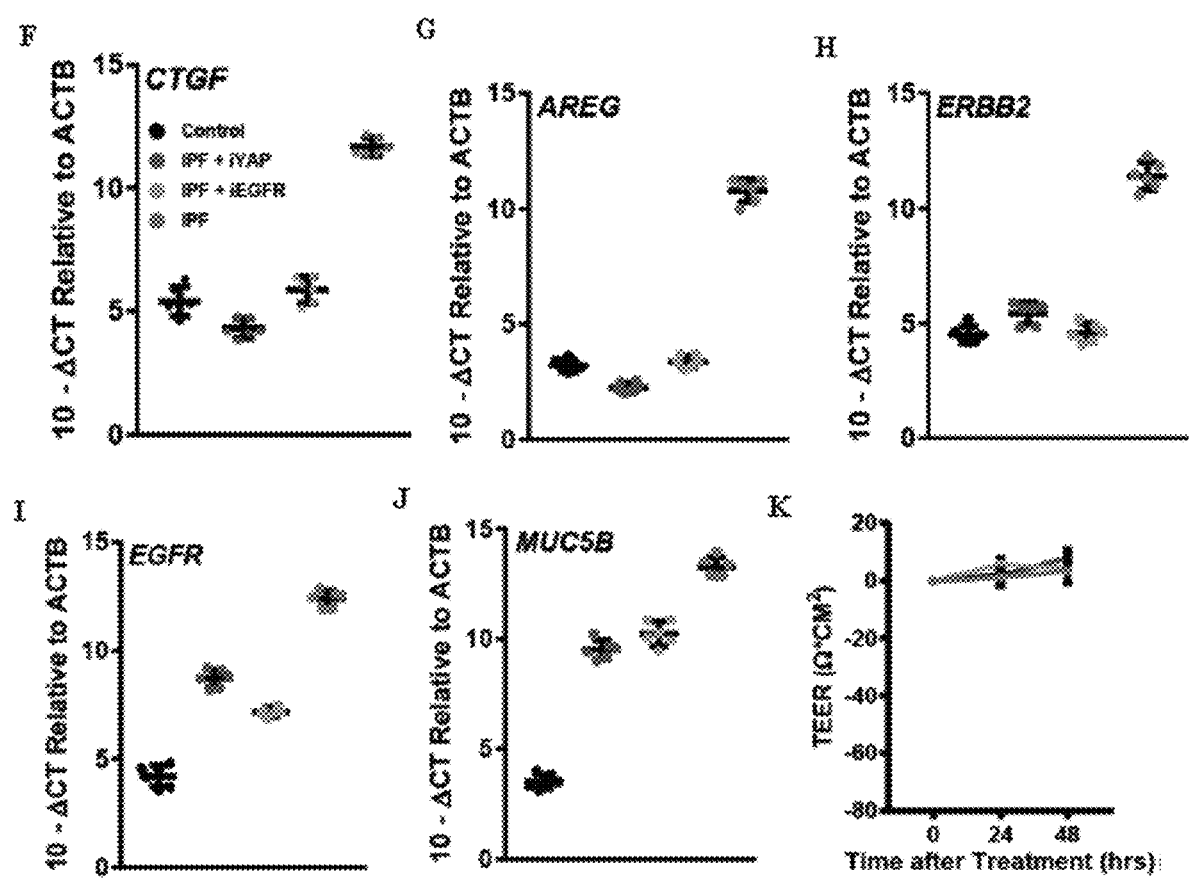
FIG. 9F-K

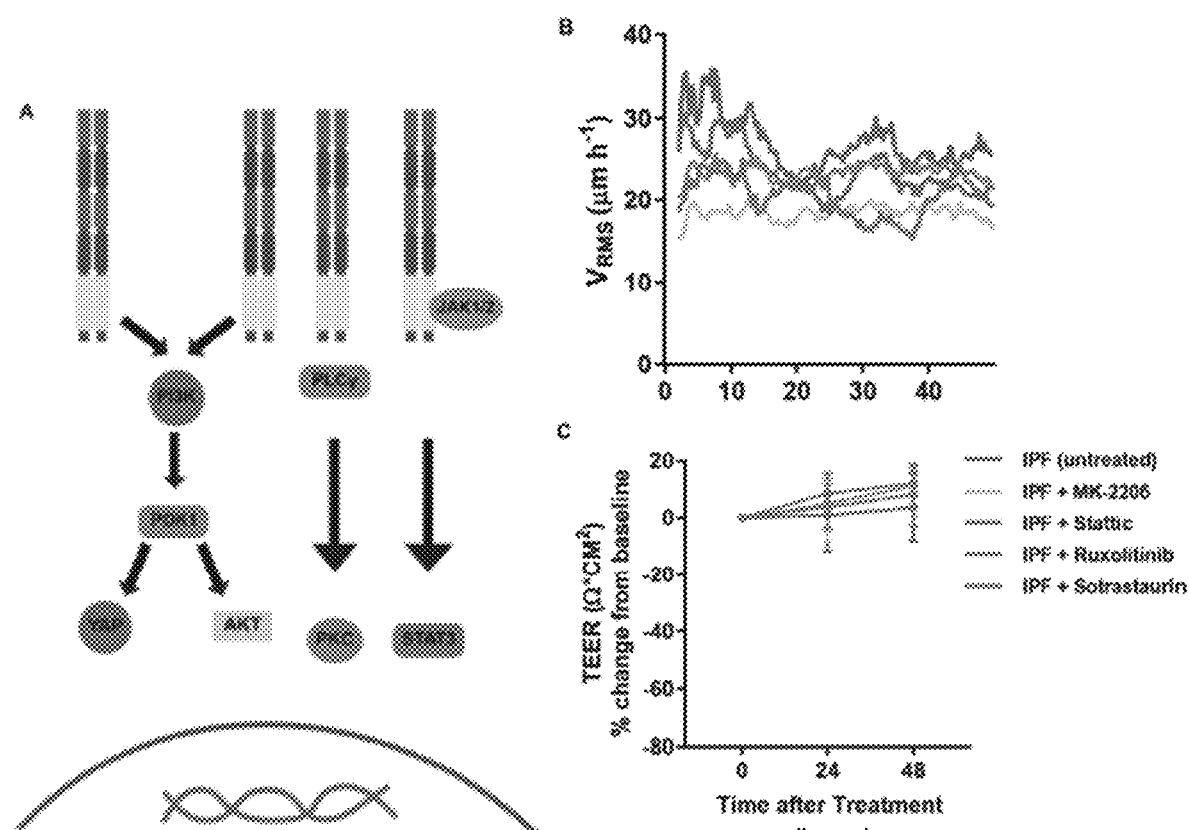
FIG. 10A-C

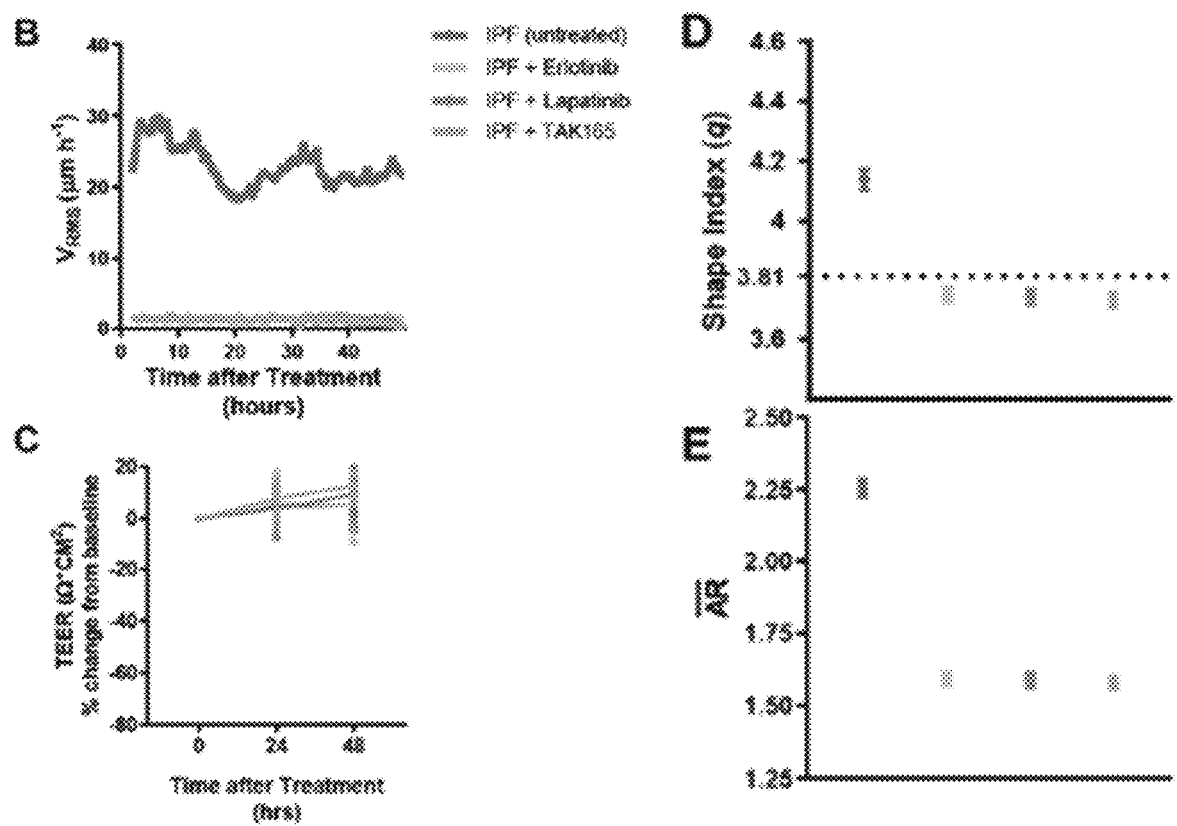
FIG. 11B-E
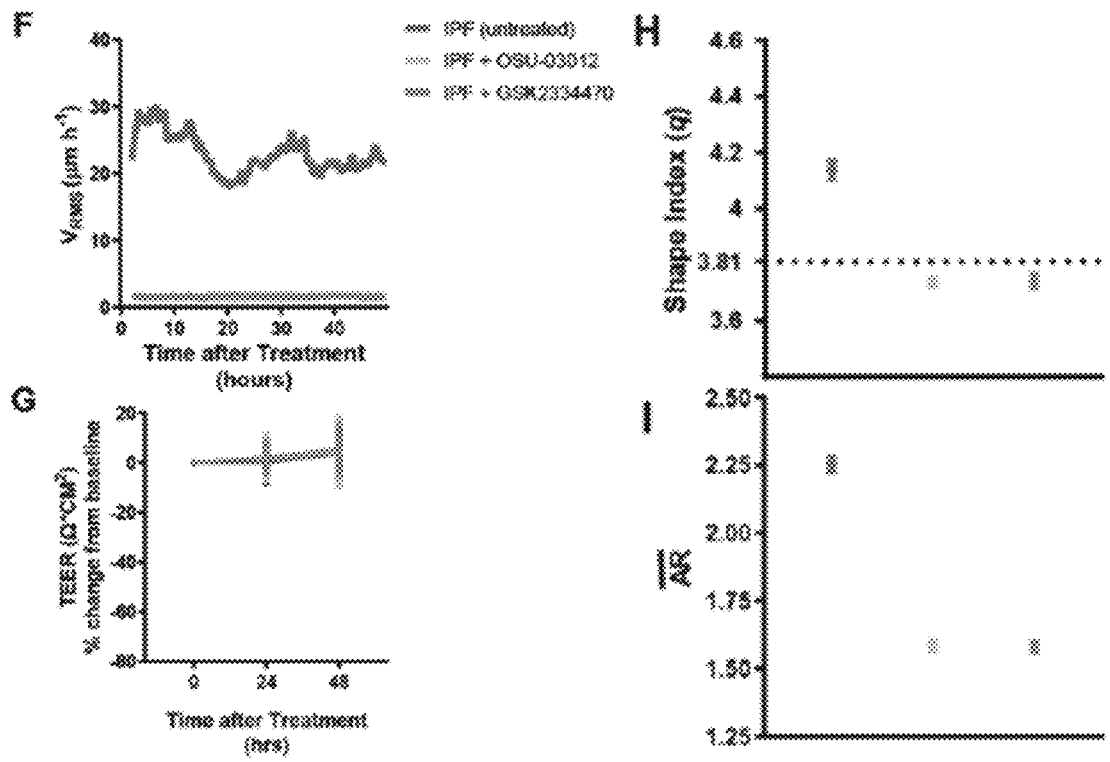
FIG. 11F-I

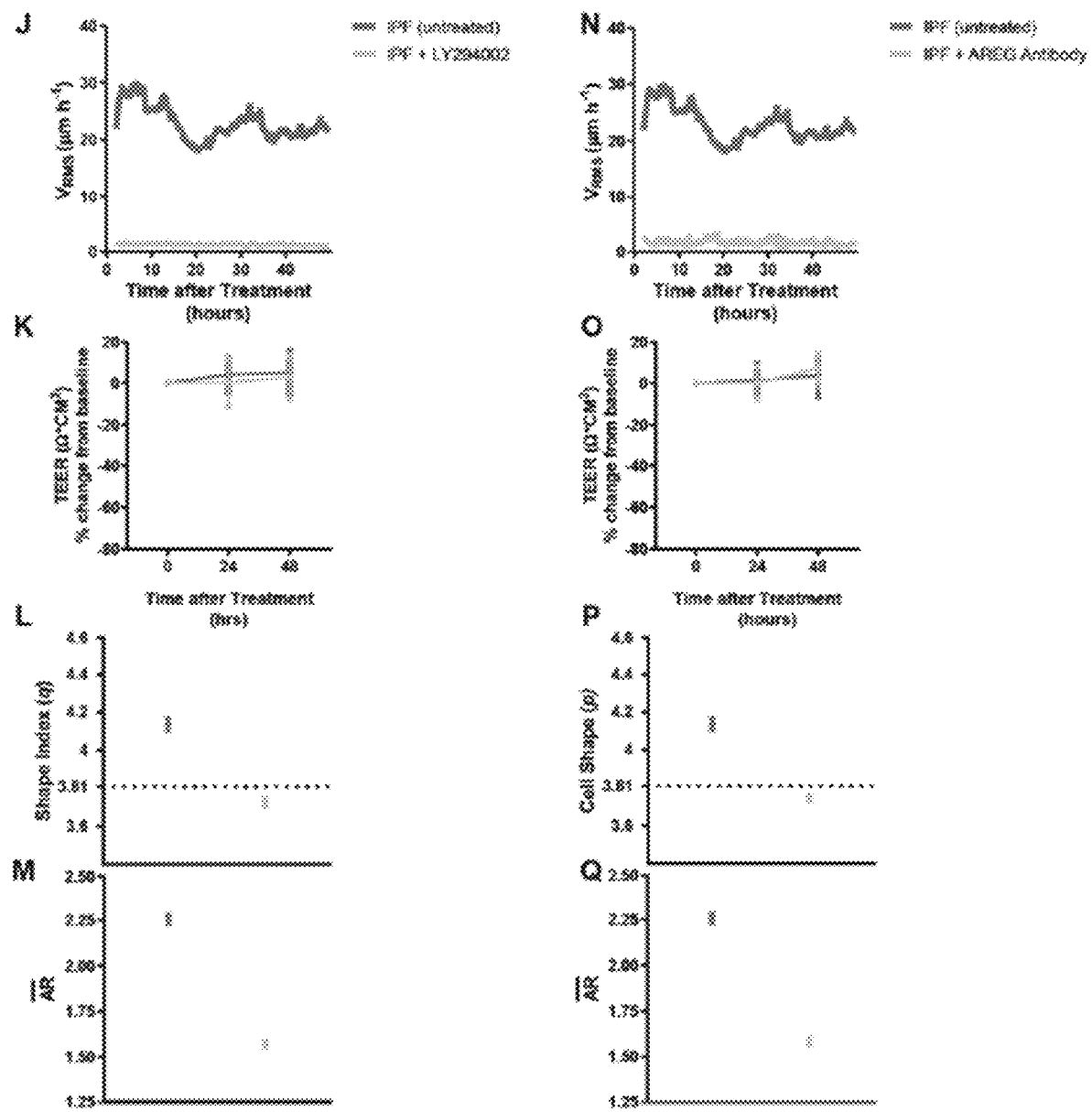
FIG. 11J-Q

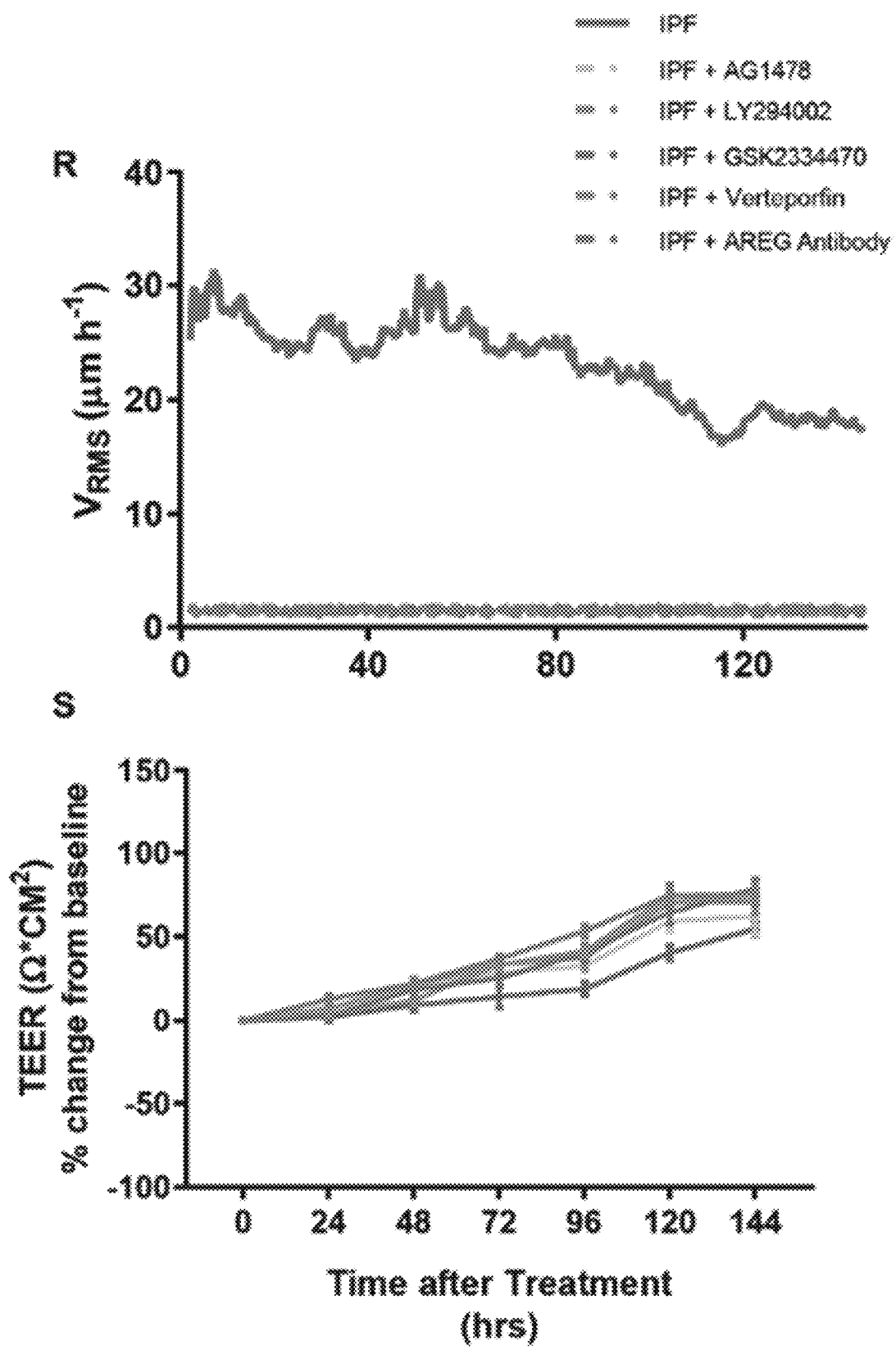
FIG. 11R-S

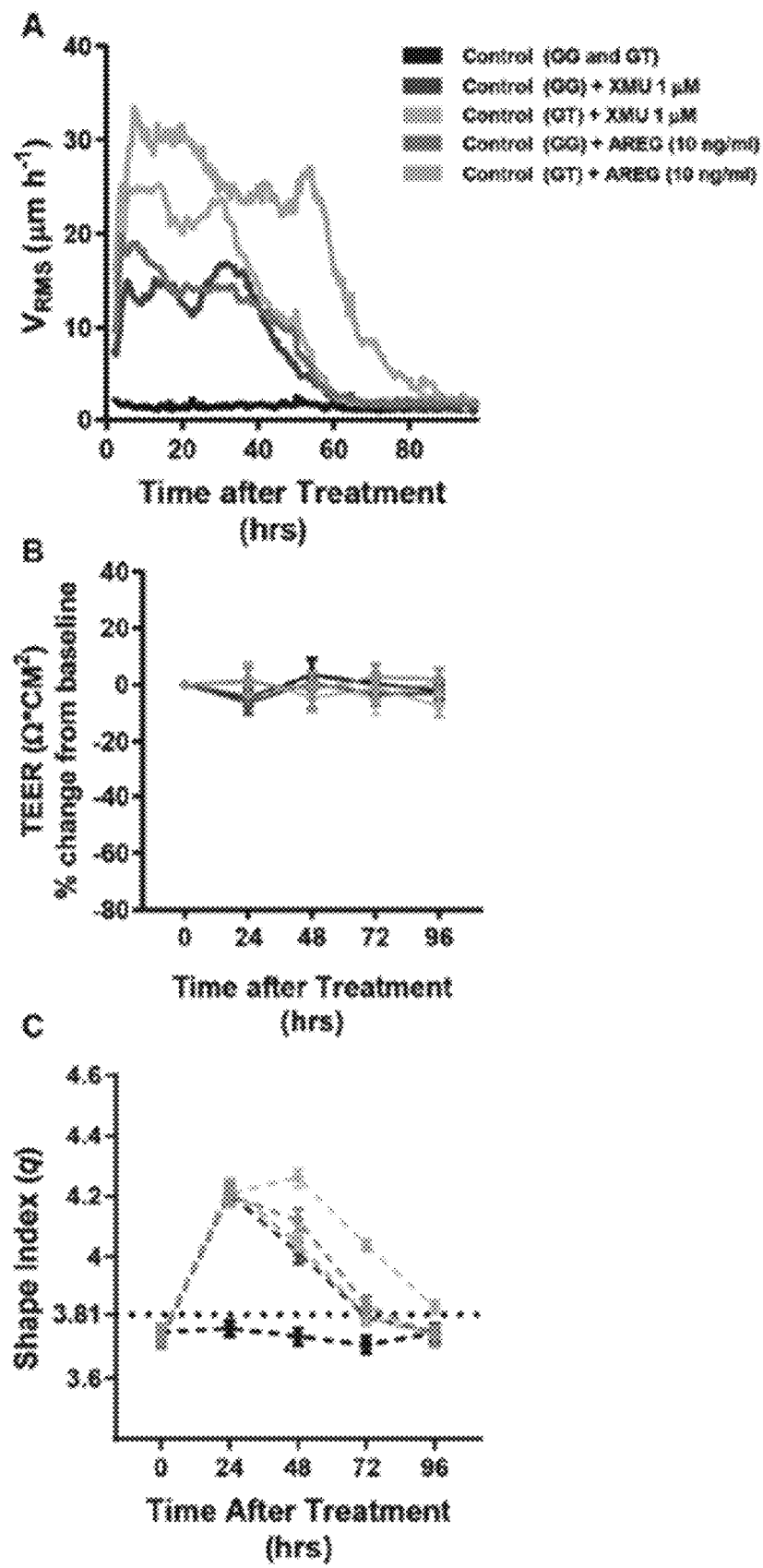
FIG. 14A-C

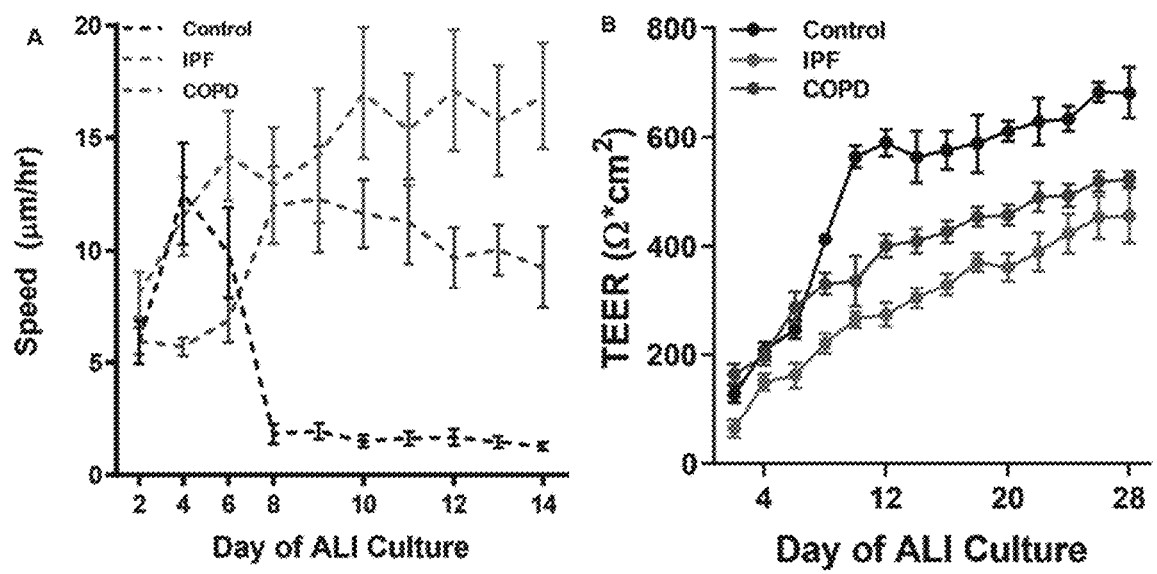
FIG. 15A-B
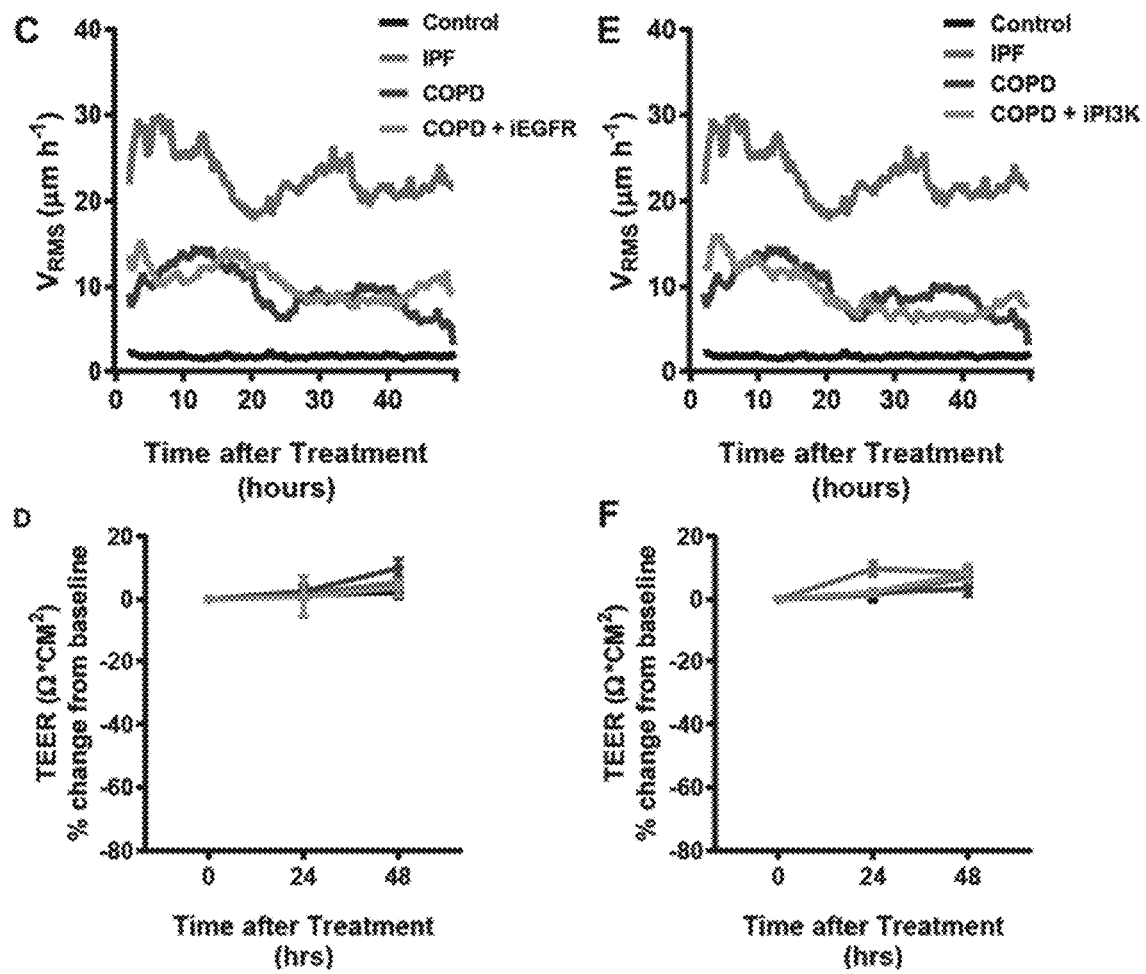
FIG. 15C-F

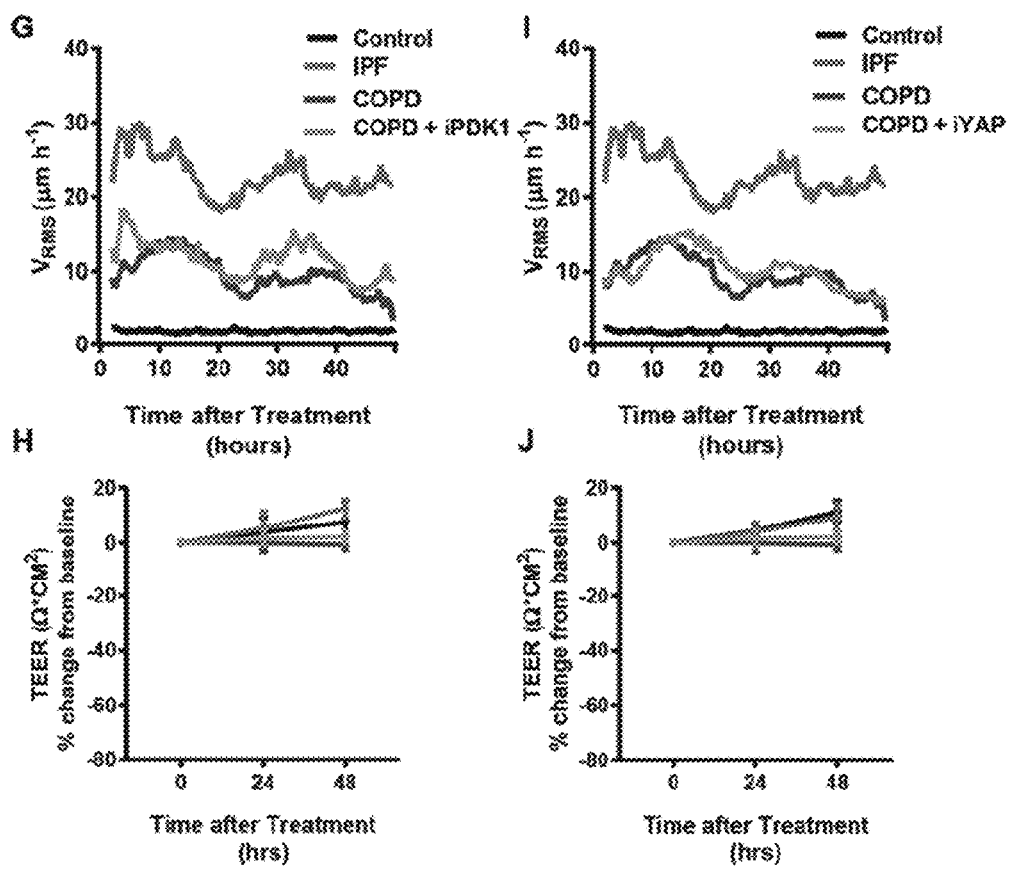
FIG. 15G-J
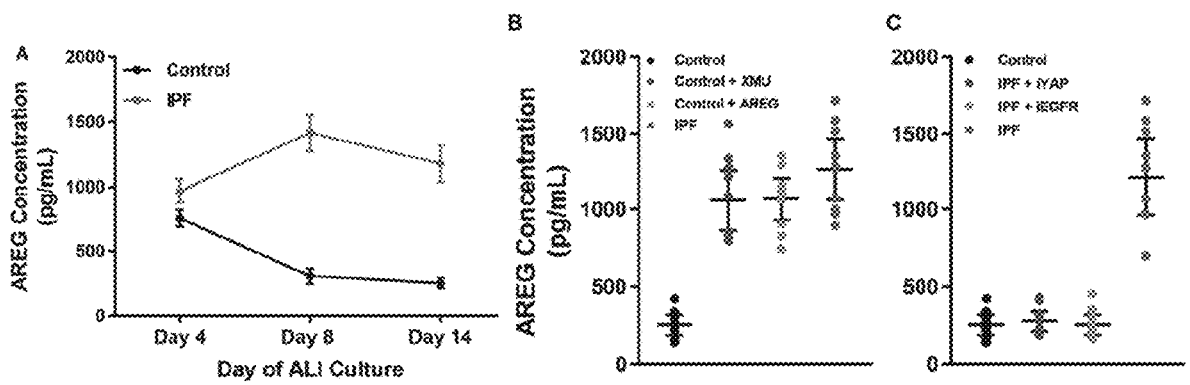
FIG. 16A-C

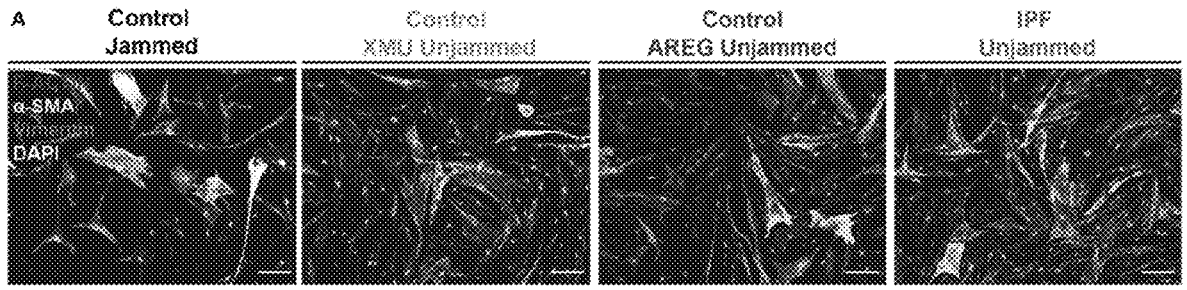
FIG. 17A
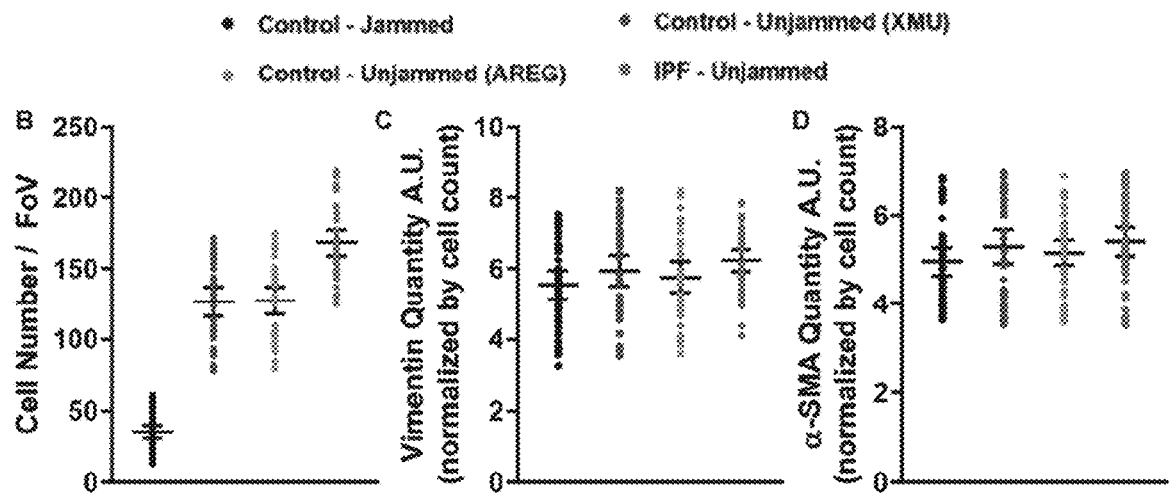
FIG. 17B-D
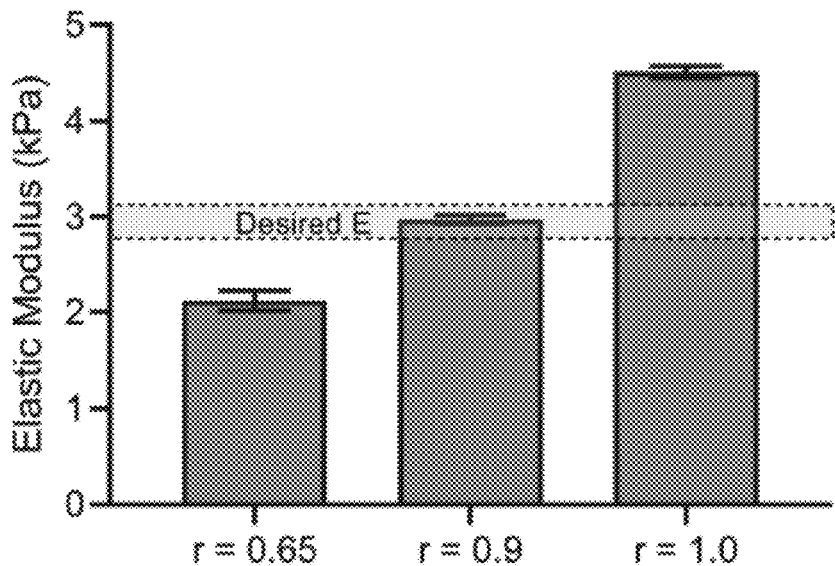
FIG. 18

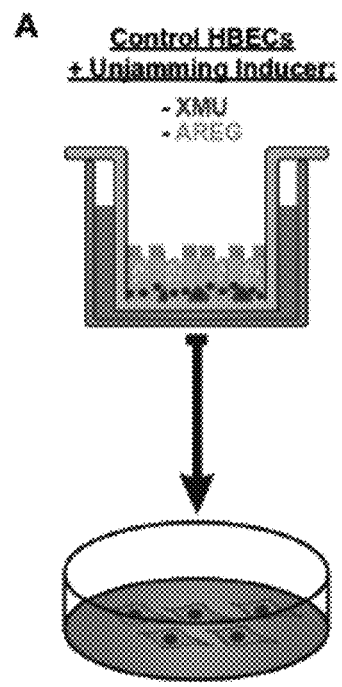
FIG. 19A
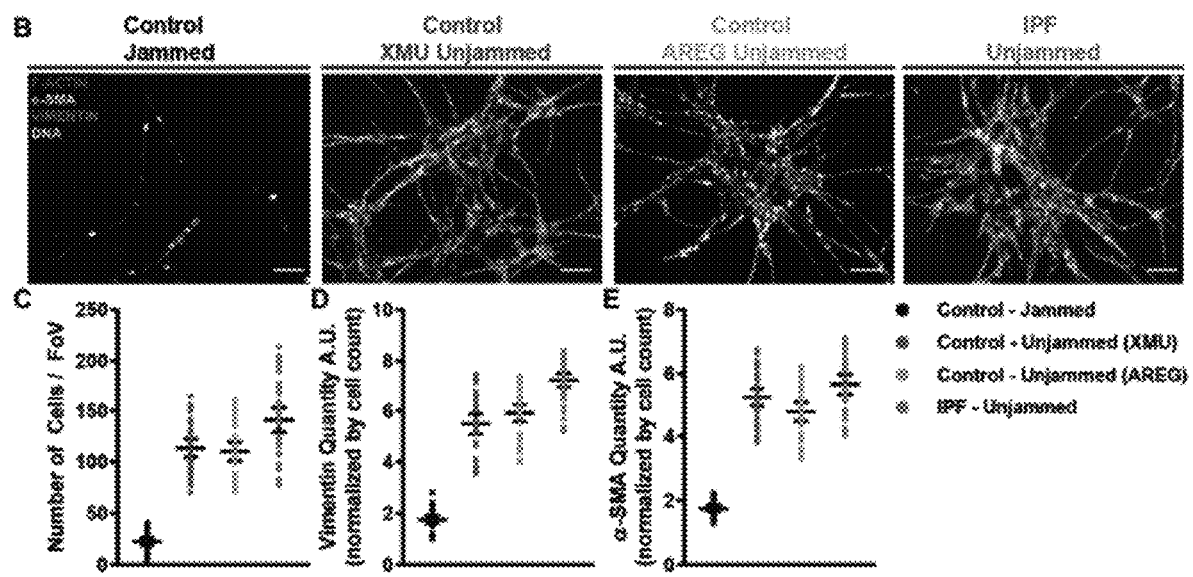
FIG. 19B-E

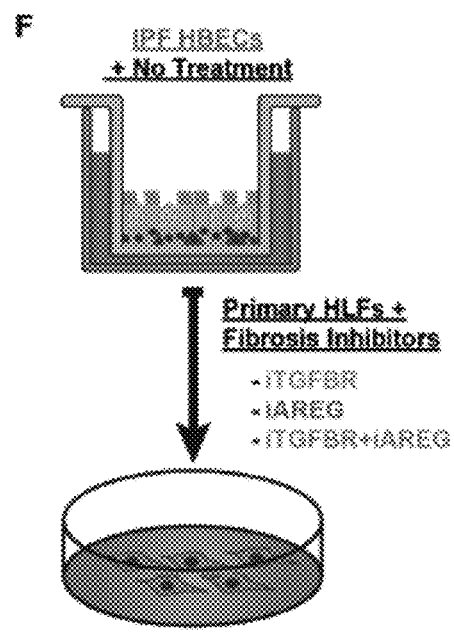
FIG. 19F
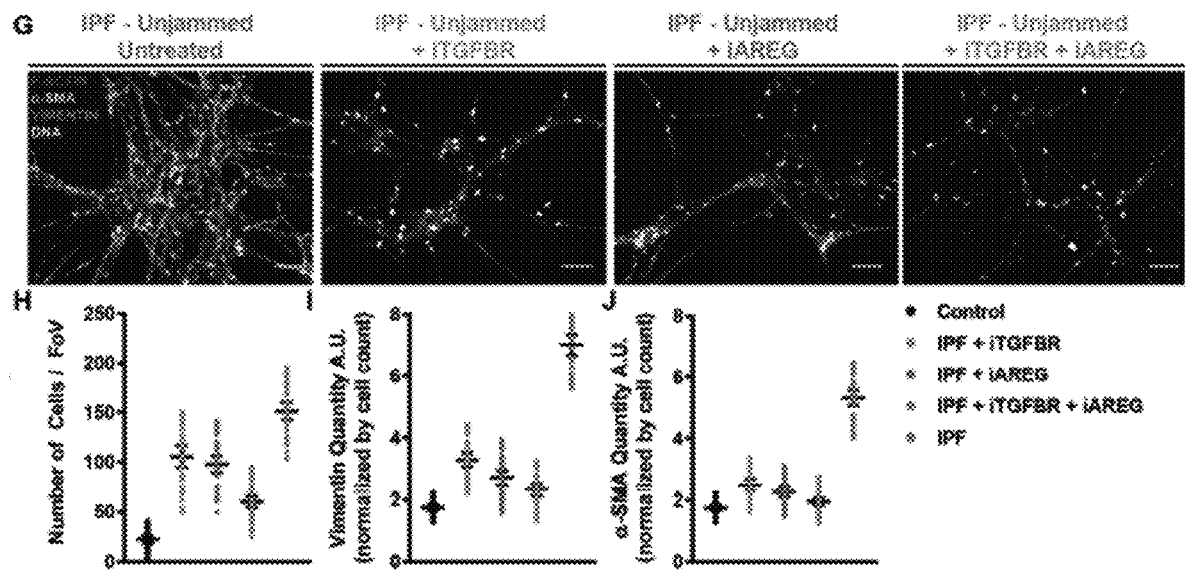
FIG. 19G-J

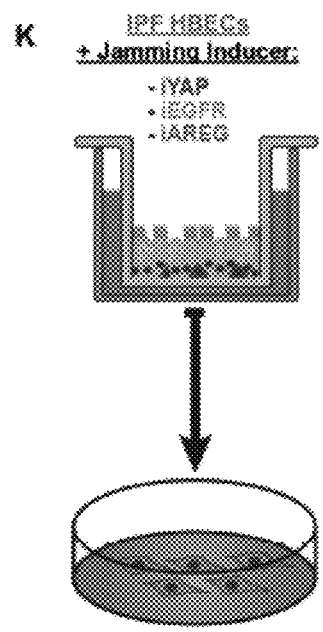
FIG. 19K
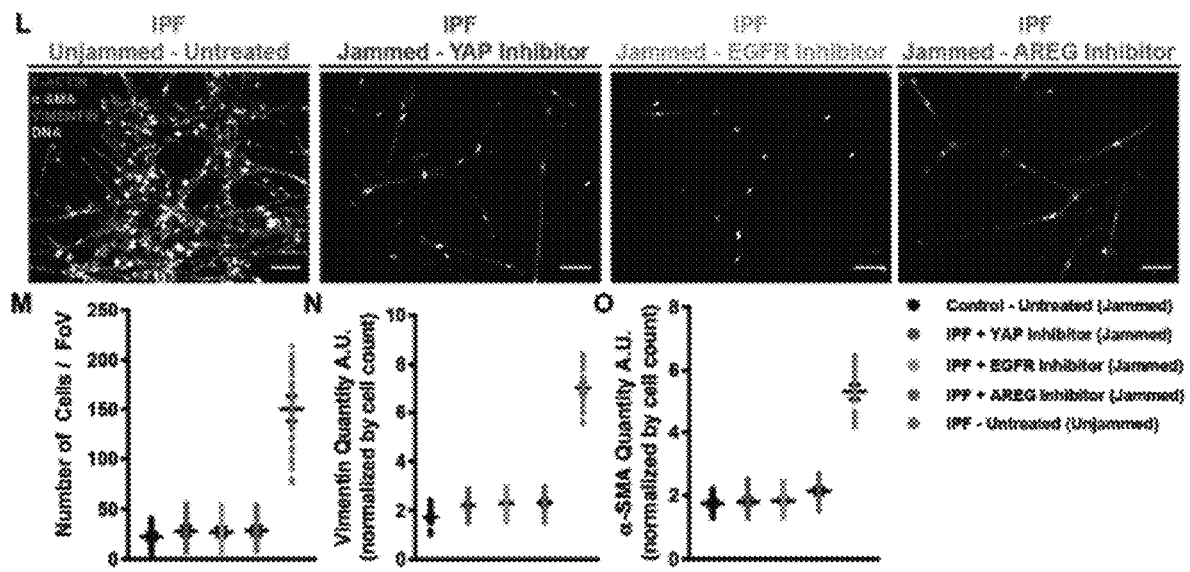
FIG. 19L-O

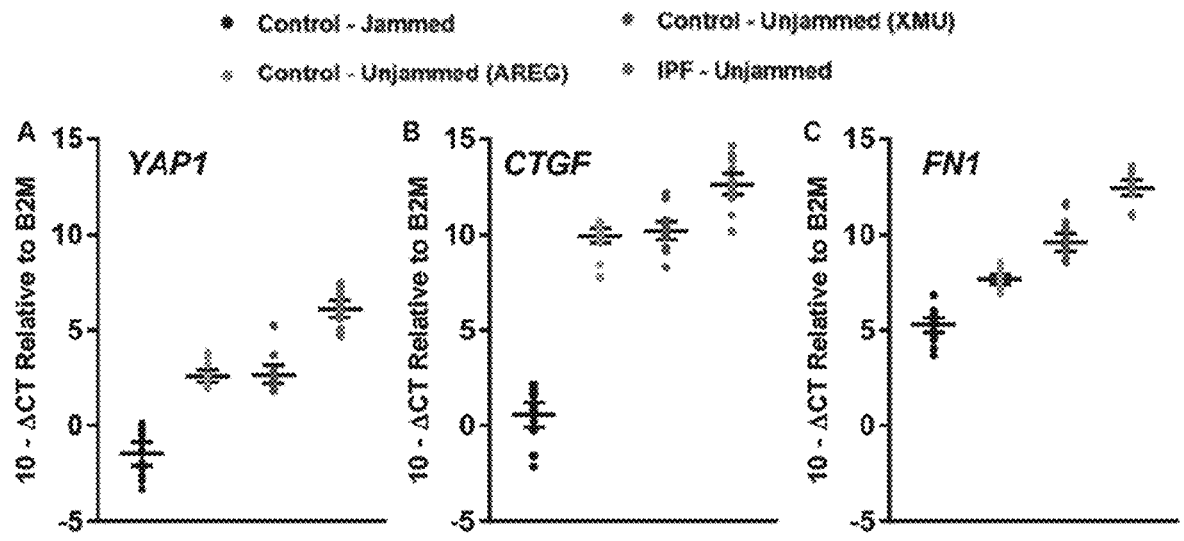
FIG. 20A-C
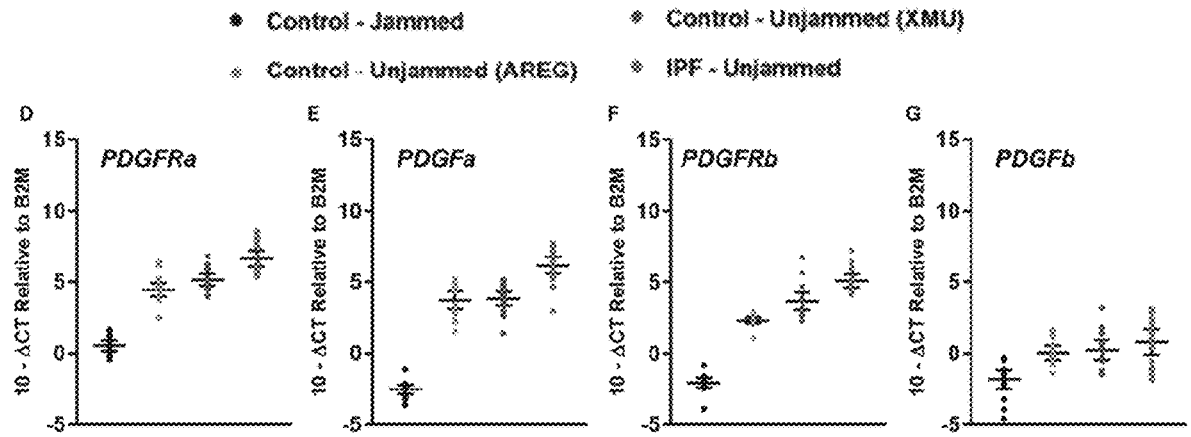
FIG. 20D-G
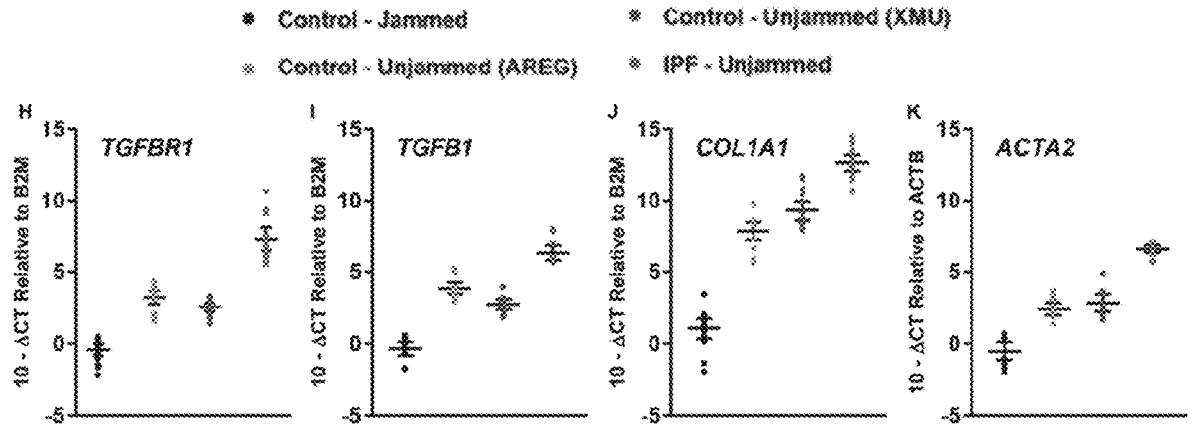
FIG. 20H-K

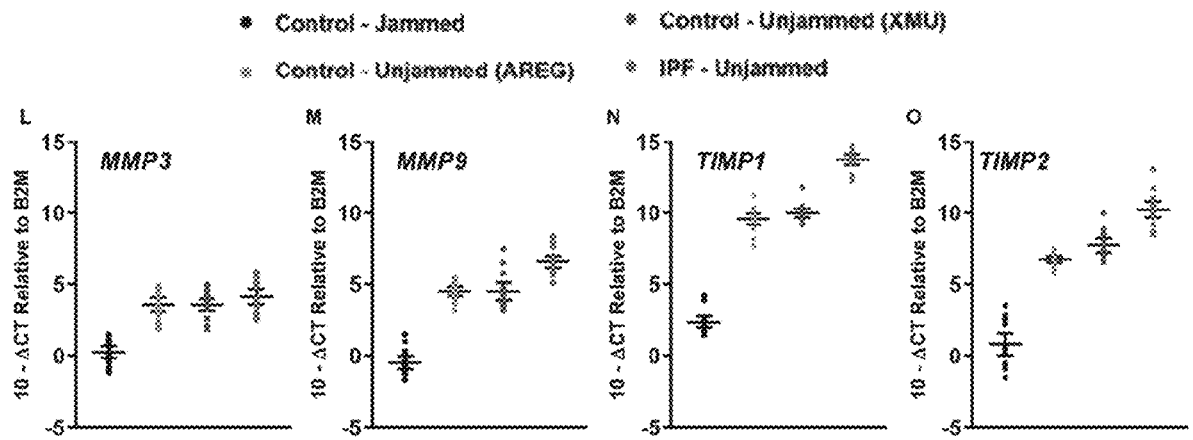
FIG. 20L-O
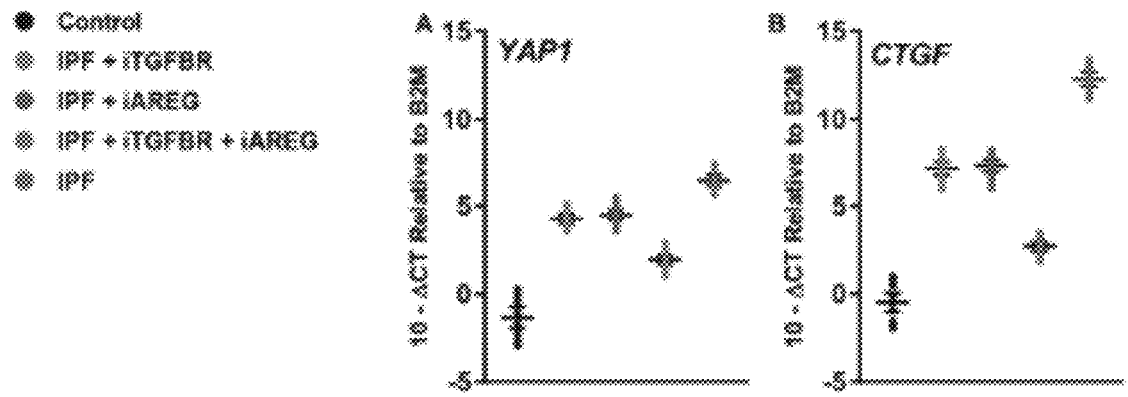
FIG. 21A-B
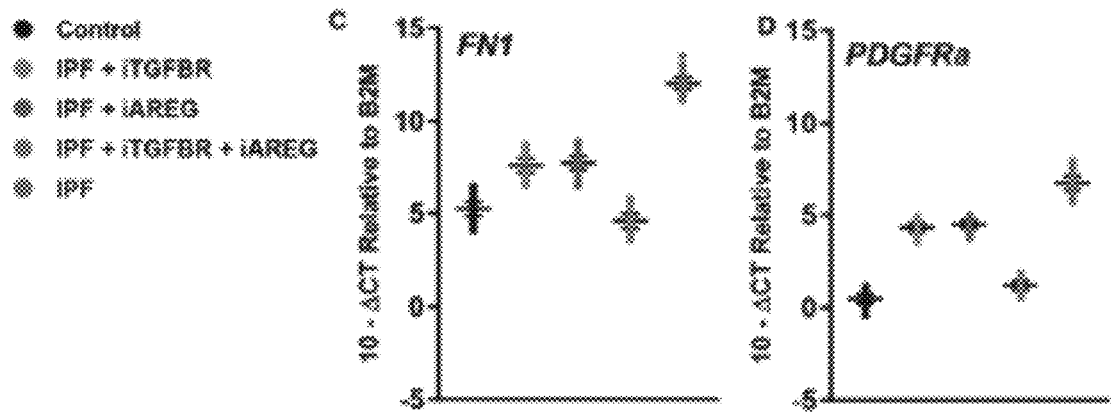
FIG. 21C-D

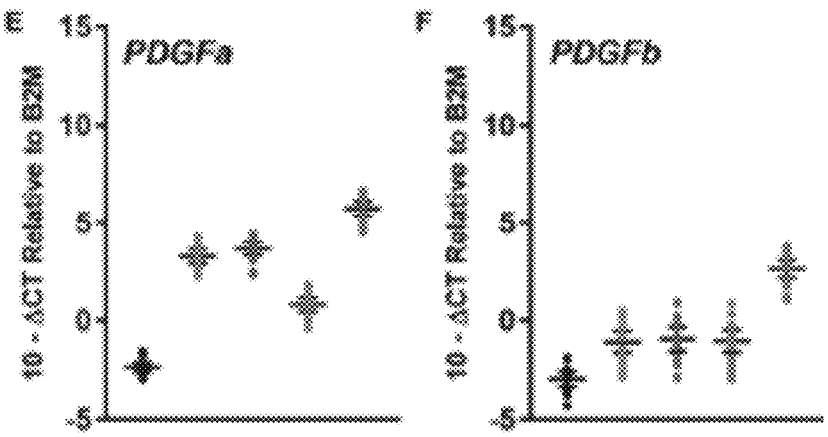
FIG. 21E-F
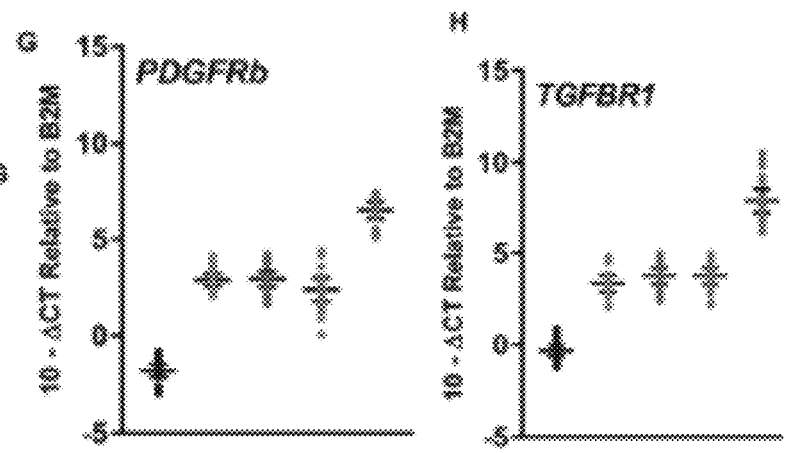
FIG. 21G-H
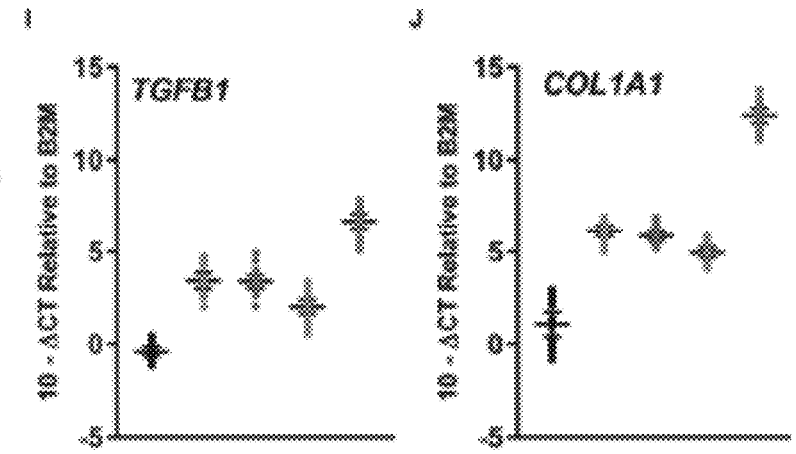
FIG. 21I-J

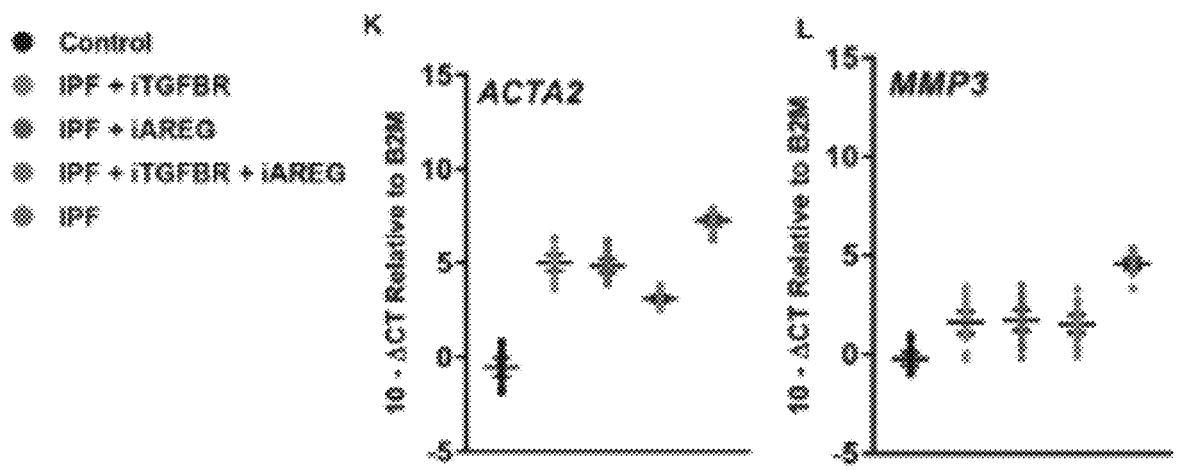
FIG. 21K-L
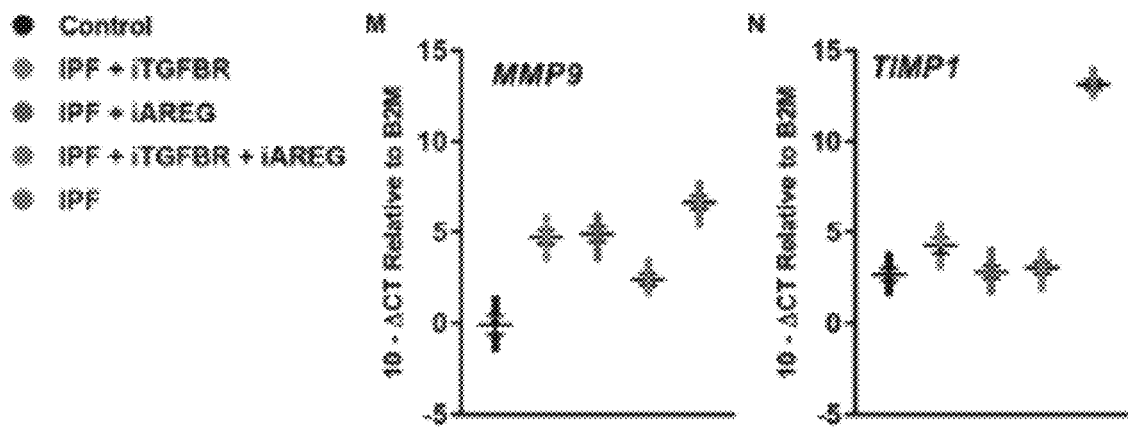
FIG. 21M-N
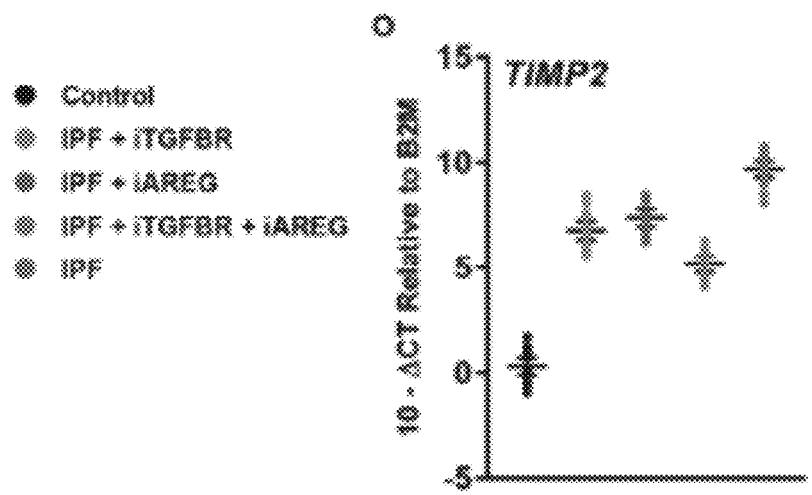
FIG. 21O

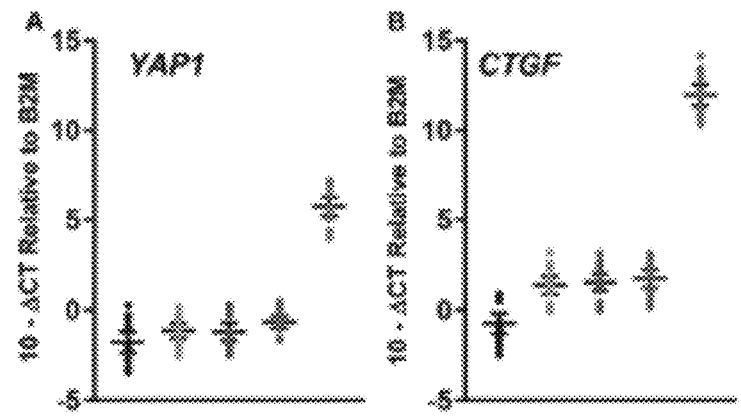
FIG. 22A-B
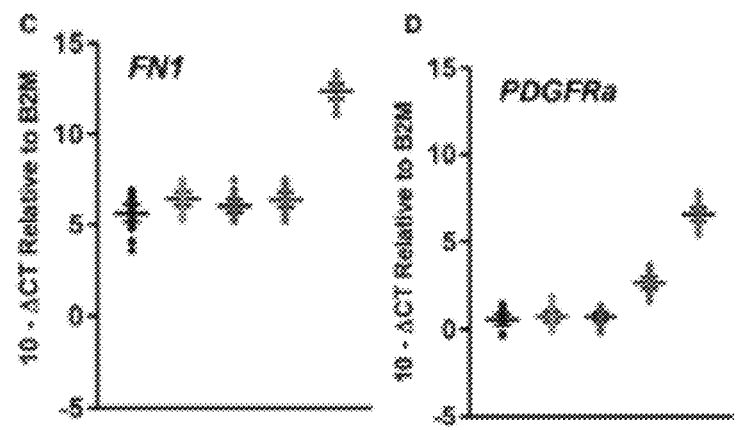
FIG. 22C-D
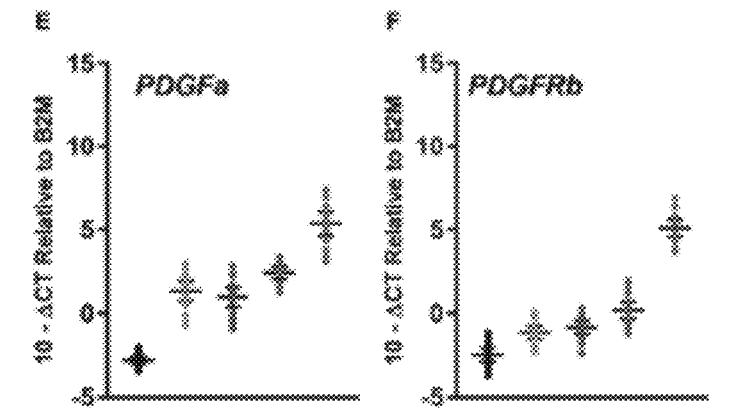
FIG. 22E-F

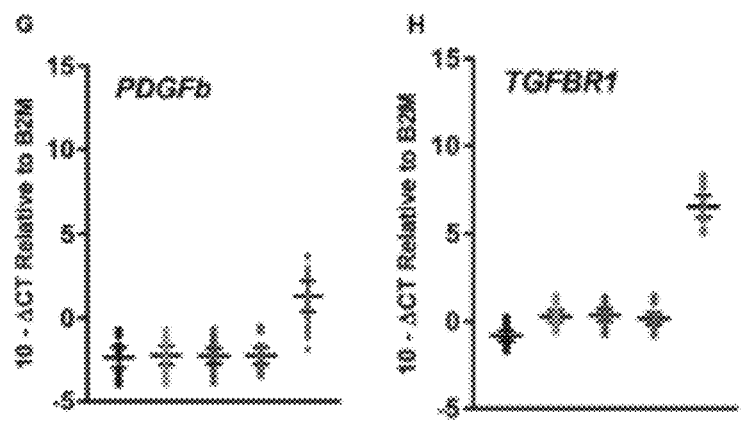
FIG. 22G-H
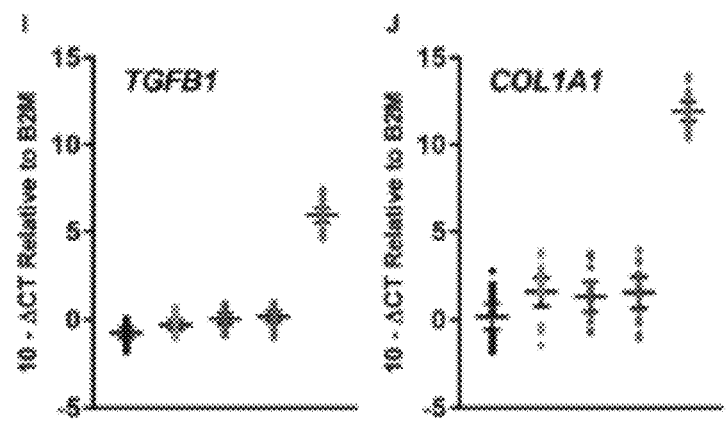
FIG. 22I-J
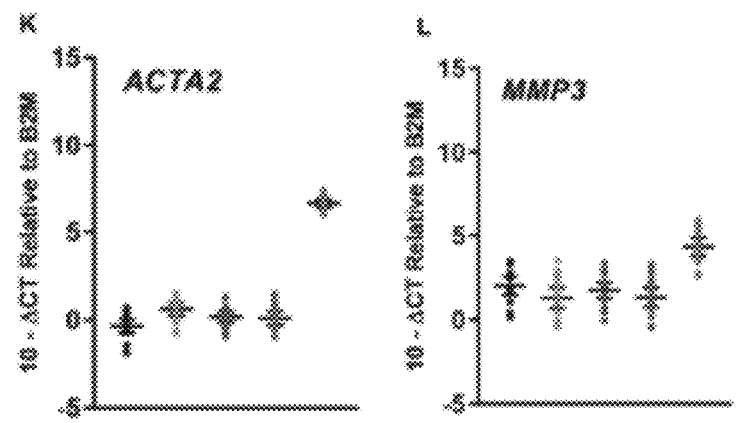
FIG. 22K-L

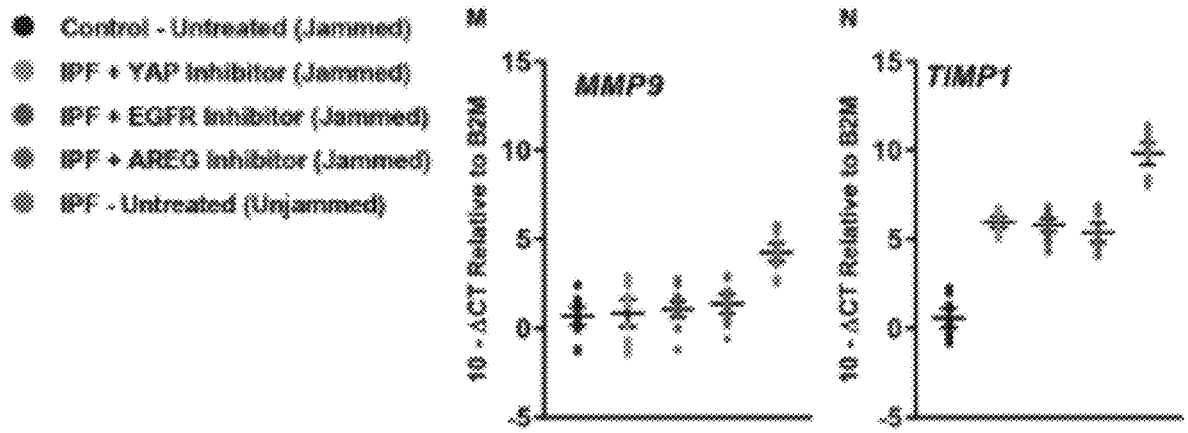
FIG. 22M-N
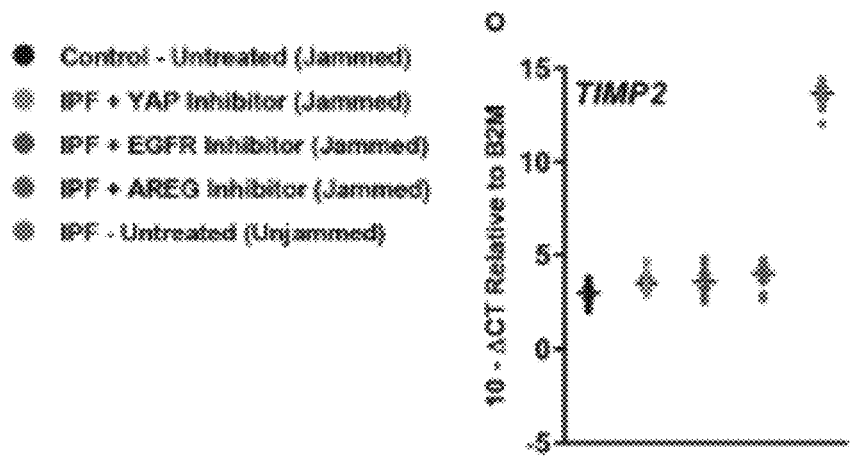
FIG. 22O

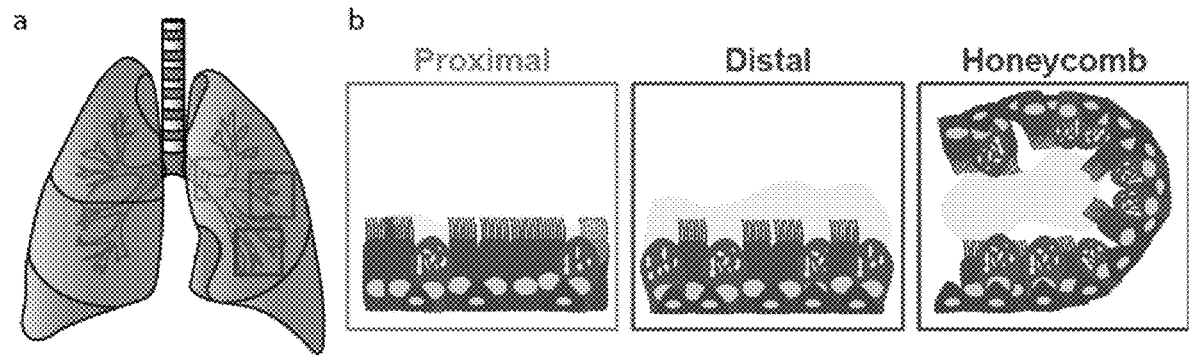
FIG. 23A-B
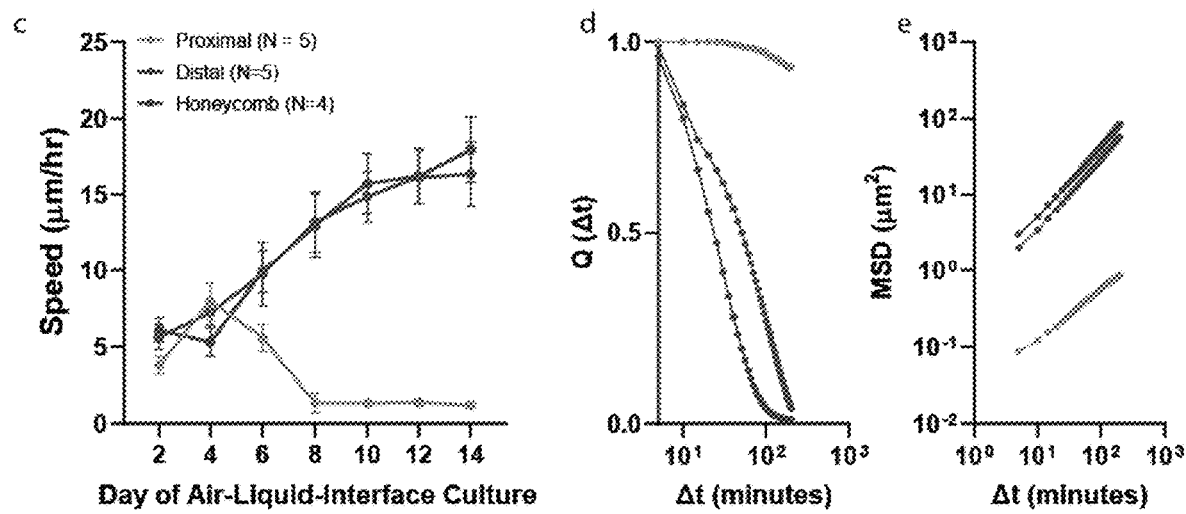
FIG. 23C-E
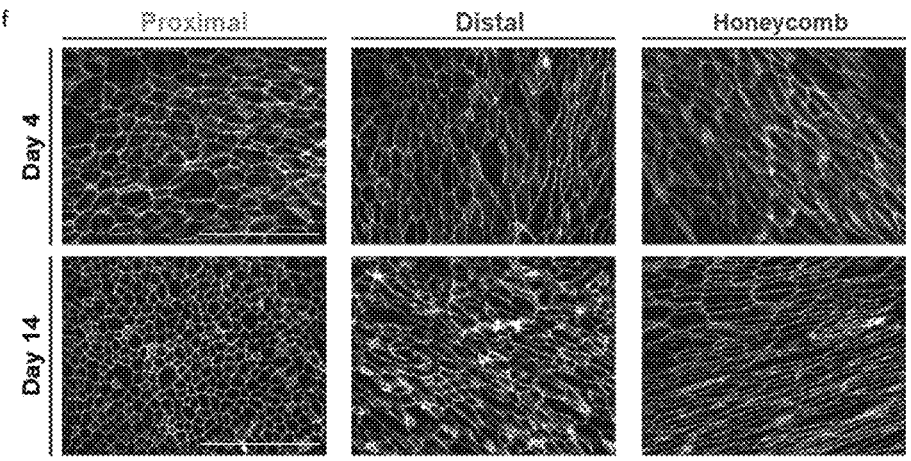
FIG. 23F

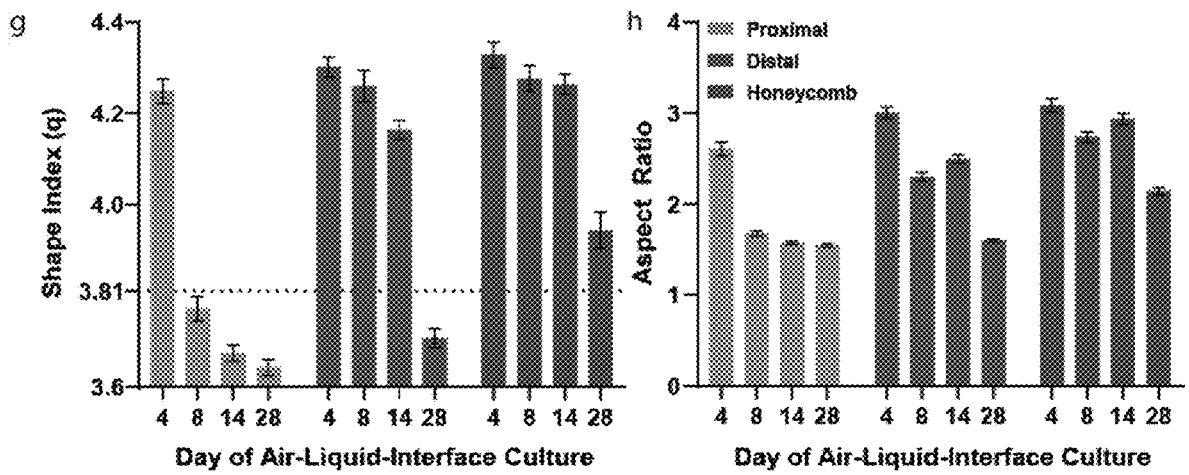
FIG. 23G-H
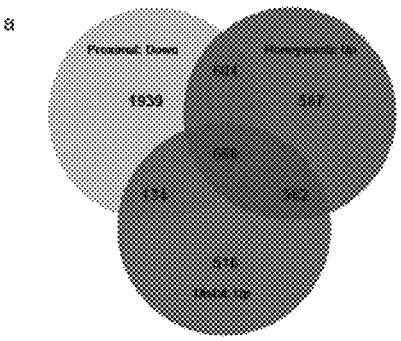
Fig. 24A
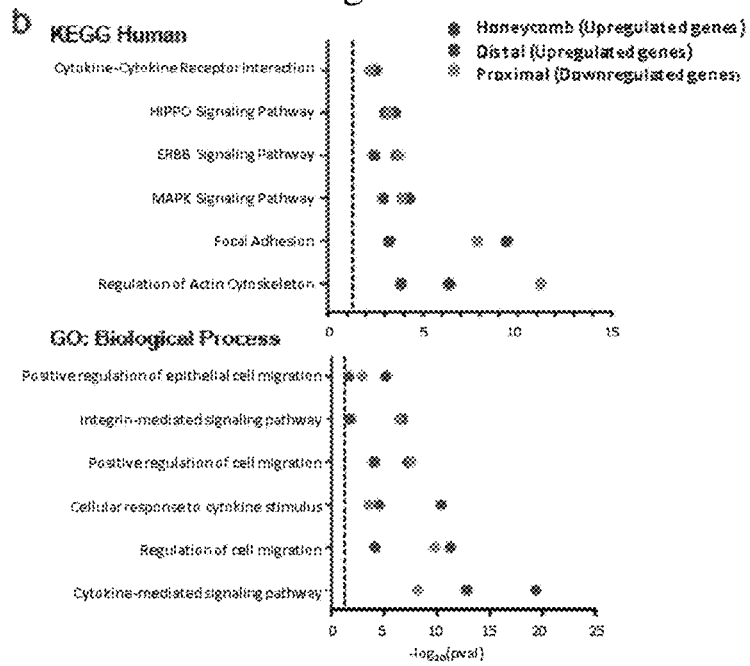
FIG. 24B

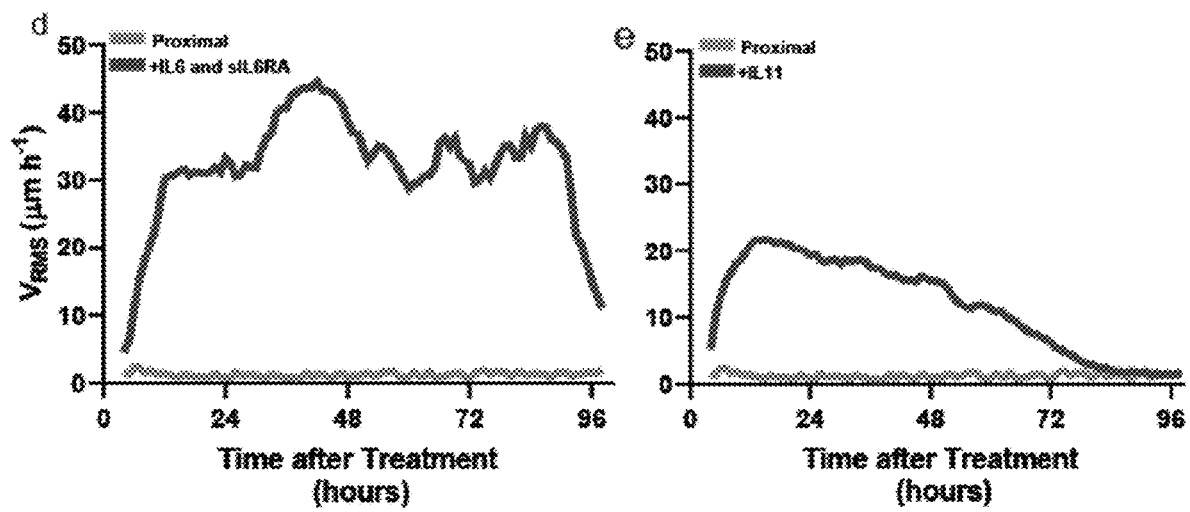
FIG. 24D-E
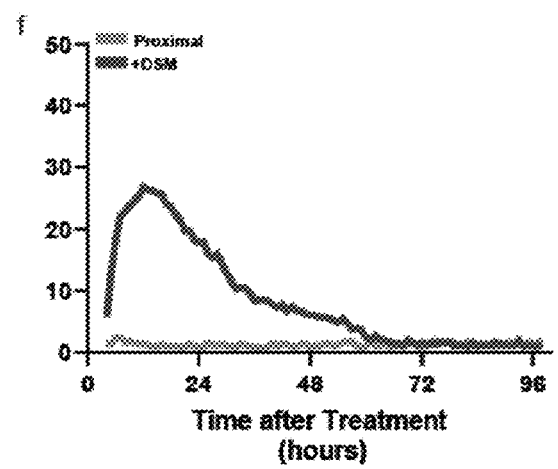
FIG. 24F

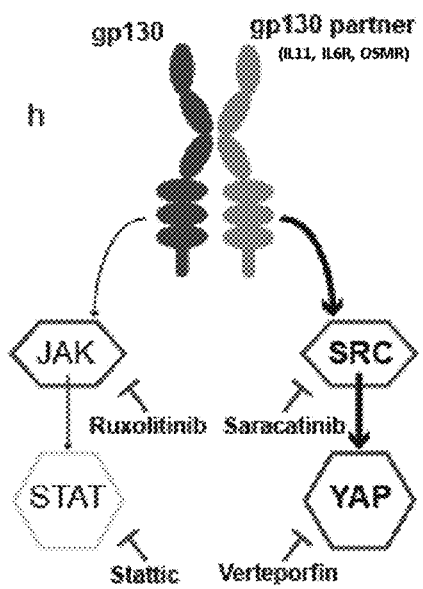
FIG. 24H
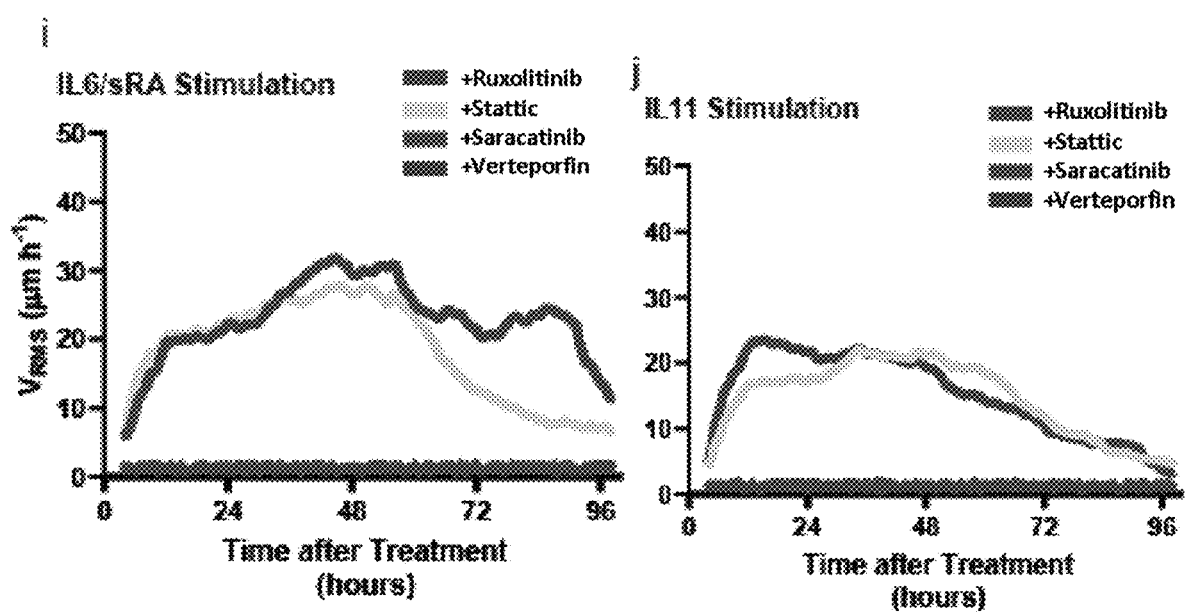
FIG. 24I-J

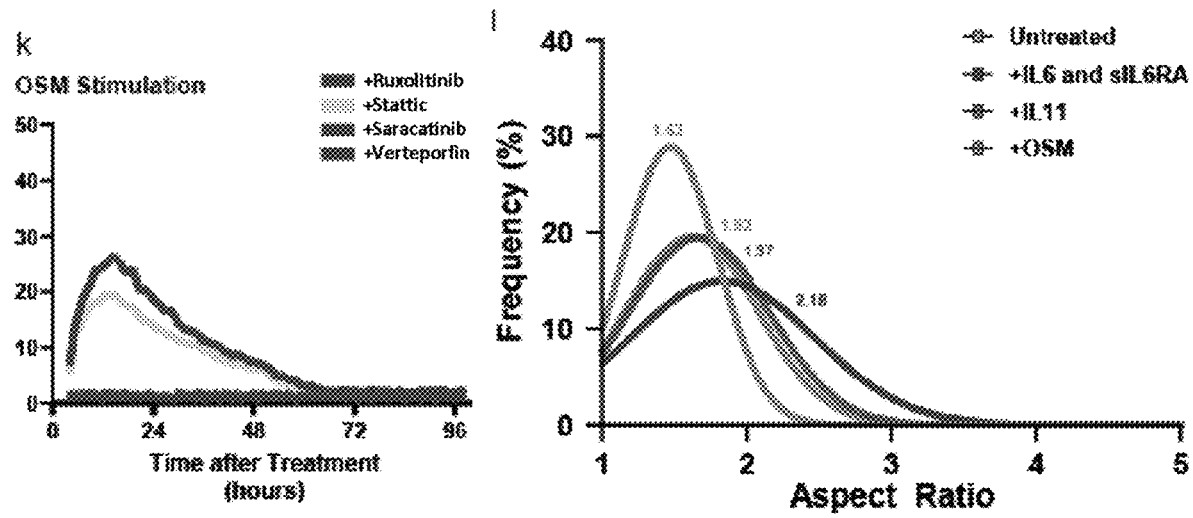
FIG. 24K-L
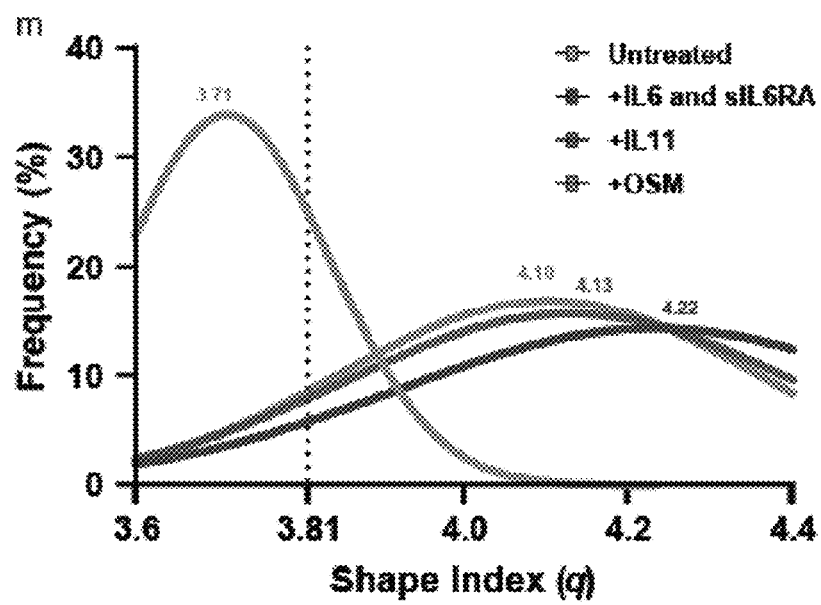
FIG. 24M

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Label
```

```
<400> SEQUENCE: 1

Cys Gly Arg Gly Asp Ser
1               5
```

FIBROSIS MODEL AND METHODS OF USE THEREOF

CROSS-REFERENCE TO RELATED APPLICATIONS

This application claims priority to U.S. Provisional Application 63/123,246 filed on Dec. 9, 2020, which is incorporated herein by reference in its entirety.

STATEMENT REGARDING FEDERALLY SPONSORED RESEARCH & DEVELOPMENT

This invention was made with government support under R01-HL097163, P01-HL092870, UH3-HL123442, and T32-AG000279 awarded by the National Institutes of Health, and W81XWH-17-1-0597 awarded by the department of Defense. The government has certain rights in the invention.

BACKGROUND

The airway epithelium serves as the interface between the host and the external environment. In many chronic lung diseases, the airway is the site of substantial remodeling after injury. Airway-specific hallmarks of idiopathic pulmonary fibrosis (IPF) include diminished mucociliary clearance, bronchiolization of the distal airspace with abnormal airway cell types and honeycomb cystic terminal airway-like structures, and loss of terminal bronchioles in regions of minimal fibrosis. While the dominant environmental (cigarette smoking) and genetic (gain of function MUC5B promoter variant) IPF risk factors target the distal airway epithelium, much attention has been focused on understanding alveolar and fibroblast contributions to progressive lung fibrosis. What is needed are models for the pathological distal airway phenotype in pulmonary fibrosis.

BRIEF SUMMARY

In an aspect, a method of screening a test compound, e.g., a fibrosis or IPF inhibitor, for induction of an unjammed-to-jammed transition (UJT) in fibrotic primary human bronchial epithelial cells (HBECs) isolated from a subject with a fibrotic lung disease comprises culturing the fibrotic primary HBECs at an air-liquid interface for a time sufficient to provide a differentiated pseudostratified epithelium; contacting the cultured cells with the test compound; and monitoring the motility of the cultured cells to identify the cultured cells as moving or stationary; wherein stationary cultured cells indicate that the test compound induces the UJT.

In another aspect, a method of identifying a lung fibrosis biomarker associated with induction of an unjammed-to-jammed transition (UJT) in fibrotic primary human bronchial epithelial cells (HBECs) isolated from a subject with a fibrotic lung disease comprises culturing the fibrotic primary HBECs at an air-liquid interface for a time sufficient to provide a differentiated pseudostratified epithelium; contacting the cultured cells with the biomarker or an expression vector for the biomarker; and monitoring the motility of the cultured cells to identify the cultured cells as moving or stationary; wherein stationary cultured cells indicate that the biomarker induces the UJT. In another aspect, a method for inducing jamming in airway epithelial cells comprising administering an IL-6 family cytokine, a SRC activator or a YAP activator in an amount to induce a jammed phase. Cells in a jammed phase remain virtually locked in place as if frozen and solid-like.

In another aspect, a method for inducing an unjammed phase in airway epithelial cells comprising administering inhibitor of EGFR, an inhibitor of YAP, or an inhibitor of SRC, in an amount to induce an unjammed phase. Cells in an unjammed phase are fluid and can migrate.

BRIEF DESCRIPTION OF THE DRAWINGS

FIG. 1A to M show IPF small airway epithelia recapitulate the in vivo condition and persist in the unjammed state. (1A) Large and small airway immunofluorescence of KRT5 and MUC5B in control and IPF patient lungs, scale bar represents 200 or 100 µm for large or small airways, respectively. (1B) Schematic of cell isolation and culture of primary HBECs. (1C) Immunofluorescence of KRT5 and MUC5B in control and IPF HBECs, scale bars represent 100 µm. (1D) Average speed (µm/hr) graphed as a function of time, error bars represent 95% confidence interval (CI). (1E) Mean-squared-displacement (MSD), (1F) overlap parameter, and (1G) cell shape index during air-liquid-interface (ALI) differentiation, error bars represent 95% CI. (1H) Representative cell shape (delineated by F-actin) and speed maps, scale bars represent 100 µm. (1I) Average speed (µm/hr) graphed as a function of time, error bars represent 95% CI. (1J) MSD, 1(K) overlap parameter, and (1L) cell shape index for large and small airways with 95% CI. (1M) Representative cell shape (delineated by F-actin) and speed maps for large and small airways, scale bars represent 100 µm.

FIG. 2A-E show similar basal cell populations in control and IPF with emergent differences after establishing air-liquid-interface. (2A) Immunofluorescence of KRT5/KRT8, KRT5/P63, and Ki67 at day 0 of ALI, scale bars represent 100 µm. (2B) Percentage of Ki67+ cells, (2C) percentage of KRT5+ cells, (2D) percentage of MUC5B+ cells at days 4, 8, and 14 of ALI, error bars represent 95% CI. (2E) Transepithelial electrical resistance across ALI, error bars represent standard error of the mean.

FIG. 3A-E show 38 genes enriched for ERBB-YAP are persistently upregulated in primary epithelia in the unjammed state. (3A) Schematic of timeline used for bulk RNA-sequence analysis for control and IPF cultures. (3B) Venn diagram of genes downregulated from day 4 and 8 in control cells and upregulated at days 8 and 14 in IPF cells. (3C) Heatmap of the 38 genes downregulated in control cells and persistently upregulated in IPF. (3D) KEGG and Gene ontology (biological process and molecular function) for the 38 genes associated with the unjammed state. (3E) Network analysis of 38 seeded genes, black nodes are seeded, dark grey nodes are associated with HIPPO signaling, and grey nodes are associated with ERBB signaling.

FIG. 4A-M show EGFR and YAP activation induce unjamming in airway epithelia. (4A) AREG staining in control and IPF distal airway epithelium with KRT5 and MUC5B co-stain, scale bar represents 100 µm. (4B) Control and IPF immunofluorescence at day 14 for ERBB2 and YAP, scale bars represent 100 µm. (4C) ERBB2 mean fluorescence, (4D) percentage of monolayer with nuclear positive YAP staining, error bars represent 95% CI. (4E-4H) Gene expression of ERBB receptors (EGFR, ERBB2) and YAP target genes (CTGF, AREG) in control and IPF day 14 HBECs, error bars represent 95% CI. (4I Root-mean-squared-velocity (VRMS), (4J) shape index, and (4K) aspect ratio of control, control+XMU, and control+AREG after treatment, error bars represent 95% C.I. (4L) Representative speed map of control, XMU, and AREG every 16 hours after treatment initiation. (4M) Cell shape 48 hours after treatment for control, XMU, and AREG 621 delineated by F actin and color-coded by aspect ratio, scale bars represent 100 μm.

FIGS. 5A-L show AREG and YAP are sufficient to drive unjamming, but not EGF or TGFα. (5A) Root mean squared velocity (VRMS), (5B) TEER of control HBECs treated EGF. (5C) VRMS, (5D) TEER of control HBECs treated with TGFα. (5E) VRMS, (5F) TEER of control HBECs treated with AREG. (5G) VRMS, (5H) TEER of control HBECs treated with XMU-MP-1. (5I) Percentage of Ki67+ HBECs 48 hours after treatment with XMU-MP-1, or (5J) 48 hours after treatment with AREG. (5K) Percentage of YAP nuclear positive HBECs 48 hours after treatment with XMU-MP-1 or AREG. (5L) Representative images of YAP nuclear localization 48 hours after XMU-MP-1 or AREG.

FIG. 6A-H show EGFR-YAP induced unjamming does not induce a partial epithelial-to mesenchymal transition. (6A-G) Gene expression of YAP target genes (CTGF, AREG), EMT associated genes (VIM, SNAIL1, ZEB1), and airway mucin genes (MUC5AC, MUC5B) 96 hours after chronic treatment with XMU (0.1 or 1 μM) AREG (10 or 100 ng/ml) or TGFβ1 (2 ng/ml), error bars represent 95% CI. (6H) Western blot for N-Cadherin, E-Cadherin, B-Actin, or Snail in control HBECs 96 hours after chronic treatment with XMU (0.1 or 1 μM) AREG (10 or 100 ng/ml) or TGFβ1 (2 ng/ml).

FIG. 7A-J show combined AREG+YAP treatment potentiates the unjammed state and EGFR-YAP driven unjamming occurs regardless of monolayer maturity. (7A) Root mean squared velocity (VRMS) and (7B) Transepithelial electrical resistance (TEER) of control HBECs treated with XMU, AREG or XMU and AREG, error bars represent standard error of the mean (SEM). (7C) Shape index and (7D) aspect ratio (AR) for control HBECs 48 hours after treatment with XMU, AREG or XMU and AREG, error bars represent 95% CI. (7E) Representative heatmap of control HBECs every 16 hours after treatment. (7F) VRMS and (7G) TEER of control HBECs at day 28 treated with XMU or AREG, error bars represent SEM. (7H) Shape index and (7I) AR of control HBECs at day 28 treated with XMU or AREG, error bars represent 95% CI. (7J) Representative heatmap of control HBECs at day 28 every 16 hours after treatment.

FIG. 8A-H show EGFR-YAP activation leads to YAP nuclear localization in FOXJ1+ cells in vitro and are present in IPF in areas of minimal fibrosis in vivo. (8A-C) Control HBECs untreated or treated with XMU or AREG, stained for YAP and club (CC10), goblet (MUC5AC), or ciliated (FOXJ1) cell markers, scale bars represent 100 μm. 8(D) Total 704 number of, (8E) percentage of FOXJ1 positive cells, (8F) percentage of YAP positive cells, and (8G) percentage of FOXJ1/YAP co-positive cells per field of view, error bars represent 95% CI. (8H) Human lung sections from an IPF patient stained for KRT5, FOXJ1, and YAP, scale bars represent 100 μm.

FIG. 9A-K show inhibition of EGFR and YAP induce the UJT in IPF epithelia. (9A) Root mean squared velocity, (9B) shape index, and (9C) aspect ratio of IPF, IPF+ Verteporfin, and IPF+ AG1478 after treatment, error bars represent 95% C.I. (9D) Representative speed maps of IPF HBECs every 16 hours after treatment. (9E) Cell shape 48 hours after treatment of IPF HBECs delineated by F-actin and color-coded by aspect ratio, scale bars represent 100 μm. (9F-J) Gene expression of ERBB receptors (EGFR, ERBB2), YAP target genes (CTGF, AREG), and MUC5B after IPF HBEC inhibition, 95% CI represented by error bars. (9K) Transepithelial electrical resistance of IPF HBECs every 24 hours after the initiation of treatment, error bars represent standard error of the mean.

FIG. 10A-C show in IPF epithelia, inhibition of AKT, JAK, STAT, or PKC does not induce jamming. (10A) Schematic of downstream ERBB-YAP signaling. (10B) Root mean squared velocity and (10C) Transepithelial electrical resistance of IPF HBECs treated with MK2206, Stattic, Ruxolitinib, or Sotrastaurin, error bars represent standard error of the mean.

FIG. 11A-S show inhibition of the ERBB-YAP axis induces jamming in IPF epithelia. (11A) Schematic of the ERBB-YAP signaling cascade. (11B) Root mean square velocity (VRMS), (11C) Transepithelial electrical resistance (TEER), (11D) shape index, and (11E) aspect ratio (AR) of IPF HBECs 48 hours after treatment with Erlotinib, Lapatinib, Mubritinib (EGFR/ERBB inhibitors), error bars represent 95% CI. (11F) VRMS, (11G) TEER, (11H) shape index, and (11I) AR of IPF HBECs 48 hours after treatment with OSU03012 or GSK2334470 (PDK1 inhibitors), error bars represent 95% CI. (11J) VRMS, (11K) TEER, (11L) shape index, and (11M) AR of IPF HBECs 48 hours after treatment with LY294002 (PI3K inhibitor) error bars represent 95% CI. (11N) VRMS, (11O) TEER, (11P) shape index and, (11Q) AR of IPF HBECs 48 hours after treatment with Amphiregulin neutralizing antibody, error bars represent 95% CI. (11R) VRMS and (11S) TEER of IPF HBECs followed for 144 hours after a single treatment with AG1478, LY294002, GSK2334470, Verteporfin, or Amphiregulin neutralizing antibody, error bars represent 95% CI.

FIG. 14A-E show rs35705950 potentiates EGFR-driven unjamming in healthy epithelia. (14A) Root mean squared velocity, (14B) transepithelial electrical resistance, and (14C) shape index of control HBECs segregated by their rs35705950 promoter variant status for 96 hours after treatment, error bars represent 95% confidence intervals. (14D) Table of peak speed and length of time in a migratory state for control HBECs after treatment segregated by their rs35705950 promoter variant status. (14E) Representative heatmaps of control HBECs every 16 hours after treatment.

FIG. 15A-J show the unjammed state in COPD is not responsive to ERBB-YAP inhibition. (15A) Average speed (μm/hr) and (15B) transepithelial electrical resistance (TEER) of control, IPF and COPD HBECs, error bars represent 95% CI. (15C) Root mean square velocity (VRMS) and (15D) TEER of COPD HBECs after AG1478 treatment, error bars represent SEM. (15E) VRMS and (15F) TEER of COPD HBECs after LY294002 treatment, error bars represent SEM. (15G) VRMS and (15H) TEER of COPD HBECs after OSU03012 treatment, error bars represent SEM. (15I) VRMS and (15J) TEER of COPD HBECs after Verteporfin treatment, error bars represent SEM.

FIG. 16A-C shows AREG secretion is modulated by altering the physical state of the epithelia. (16A) Control and IPF HBEC AREG concentration throughout ALI. (16B) AREG concentration after control HBEC induced unjamming. (16C) AREG concentration after IPF HBEC induced jamming.

FIG. 17A-D show human lung fibroblasts on plastic fail to demonstrate robust treatment differences. (17A) Immunofluorescence of primary human lung fibroblast (HLF) seeded on tissue culture plastic 72 hours after treatment with control-jammed, control-YAP unjammed, control-AREG unjammed, or IPF-unjammed HBEC media, scale bar represents 100 μm. (17B) Cell number, (17C) vimentin, and (17D) alpha-SMA mean fluorescence of treated HLF, error bars represent 95% CI.

FIG. 18 shows synthesized hydrogel stiffness is 3 kPa. Elastic modulus of synthesized hydrogel, r represents the ratio of macromer end groups that are crosslinked. A hydrogel with a r of 0.9 has 90% of end groups crosslinked, which allows for the remaining, un-crosslinked groups, to be conjugated with adhesive peptides.

FIG. 19A-O show the signaling and biophysical state of epithelia direct fibroblast activation. (19A) Schematic of HLF treatment with conditioned media from control HBECs in an induced unjammed state. (19B) Immunofluorescence for vimentin, alpha-SMA, and F-actin (markers of fibroblast activation). (19C) Number of cells per field of view, (19D) vimentin mean fluorescence, and (19E) alpha-SMA mean fluorescence, all error bars represent 95% C.I. (19F) Schematic of HLF treatment with conditioned media from untreated IPF HBECs supplemented with inhibitors targeted for HLFs (19G) Immunofluorescence of markers of fibroblast activation. (19H) Number of cells per field of view, (19I) vimentin mean fluorescence, and (19J) α-SMA mean fluorescence. (19K) Schematic of HLF treatment with conditioned media from induced-jammed IPF HBECs. (19L) Immunofluorescence of markers of fibroblast activation. (19M) Number of cells per field of view, (19N) vimentin mean fluorescence. (19O) alpha-SMA mean fluorescence.

FIG. 20A-O show the unjammed state induces pro-fibrotic gene expression in primary human lung fibroblasts. (20A-O) Gene expression 72 hours after treatment with HBEC media, error bars represent 95% confidence interval.

FIG. 21A-O show direct inhibition of human lung fibroblast attenuates unjammed induced profibrotic gene expression. (21A-O) Gene expression 72 hours after treatment with HBEC media, error bars represent 95% confidence interval.

FIG. 22A-O show induced jamming in IPF epithelia media rescues pro-fibrotic gene expression in human lung fibroblasts. (22A-O) Gene expression 72 hours after treatment with HBEC media, error bars represent 95% confidence interval.

FIG. 23A-H show proximal cultures from epithelial cells behave most similarly to healthy patient samples. (23A-B) Schematic of dissections of the airway tree from a patient, with cells from the proximal (cartilaginous airways), distal (respiratory airways), and honeycomb cyst epithelia (regions with microscopic honeycombing). Canonical dynamic measurements: (23C-E) and cell-structure (23F-H) confirmed the airway epithelial dysfunction was potentiated along the proximal-distal axis in IPF patients.

Figure 8A:
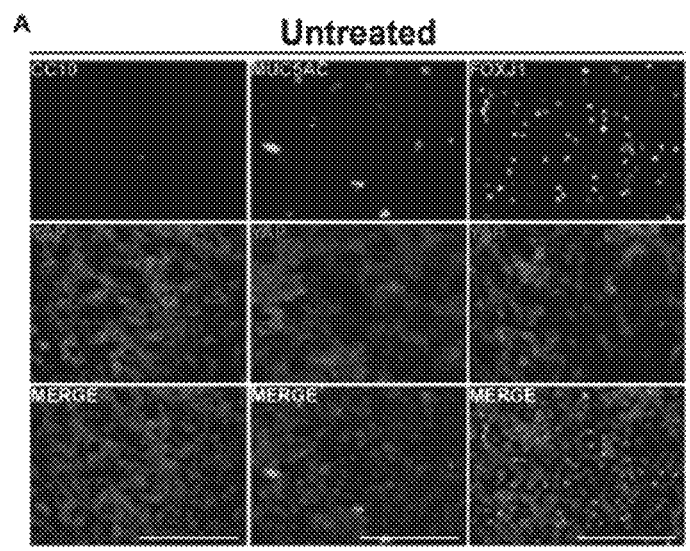
Figure 8B:
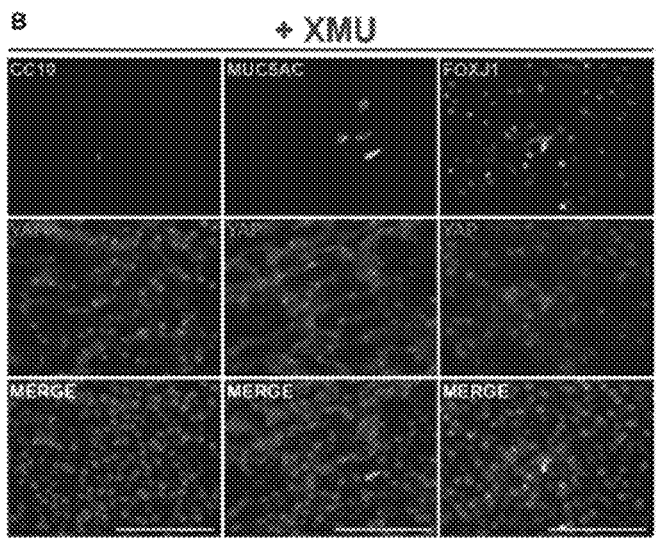
Figure 8C:
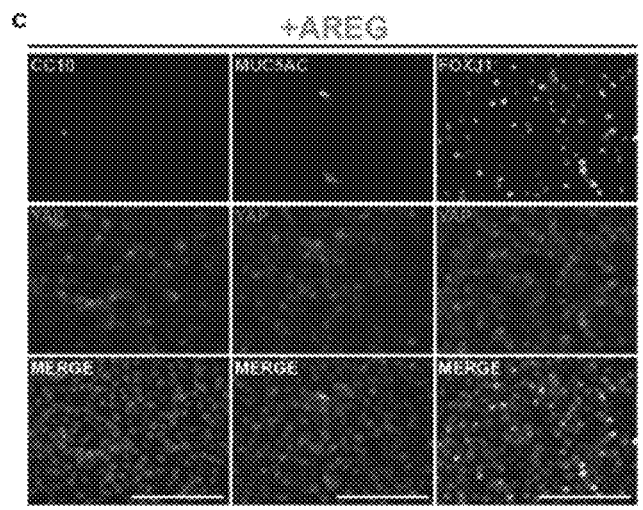
Figure 9D:
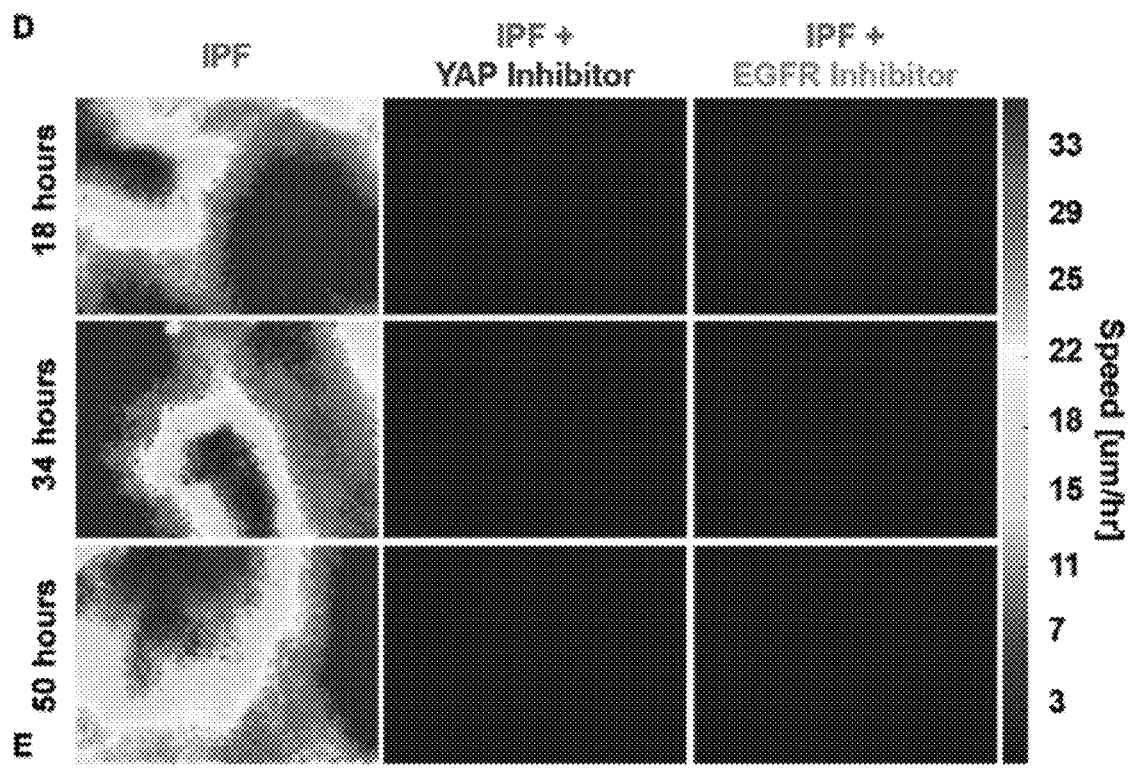
Figure 9E:
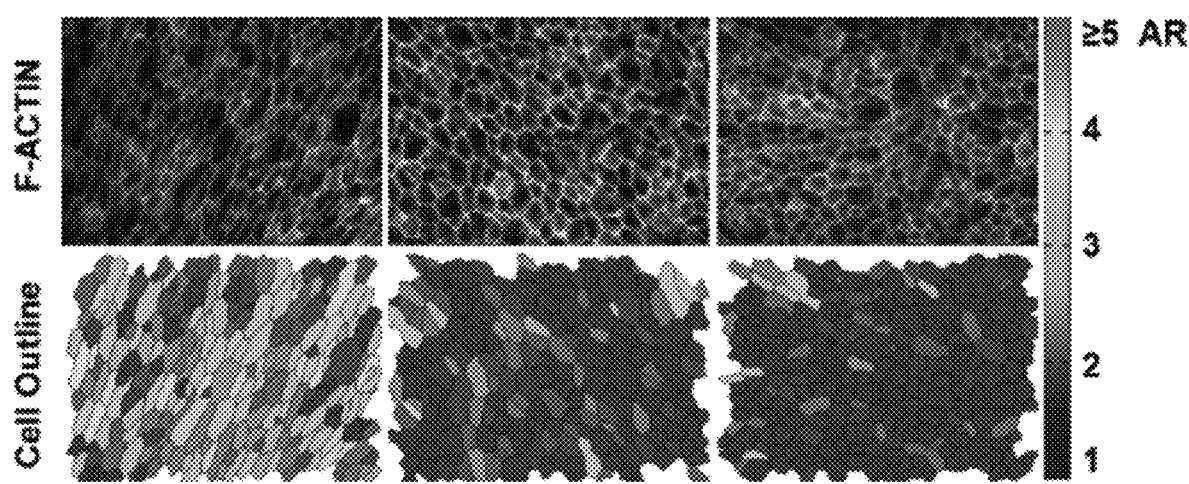

The above-described and other features will be appreciated and understood by those skilled in the art from the following detailed description, drawings, and appended claims.

DETAILED DESCRIPTION

Described herein are methods of screening test compounds expected to be useful for treatment of fibrotic lung diseases such as IPF and methods of identifying lung fibrosis biomarkers. The methods are based on the unexpected discovery that healthy and IPF airway epithelia are biophysically distinct, and the induction of an unjammed-to-jammed transition (UJT) in fibrotic primary human bronchial epithelial cells (HBECs) can be used to screen test compounds and identify biomarkers. The airway epithelium serves as the interface between the host and external environment. In many chronic lung diseases, the airway is the site of substantial remodeling after injury. While, idiopathic pulmonary fibrosis (IPF) has traditionally been considered a disease of the alveolus and lung matrix, the dominant environmental (cigarette smoking) and genetic (gain of function MUC5B promoter variant) risk factor primarily affect the distal airway epithelium. Moreover, airway-specific pathogenic features of IPF include bronchiolization of the distal airspace with abnormal airway cell-types and honeycomb cystic terminal airway-like structures with concurrent loss of terminal bronchioles in regions of minimal fibrosis. However, the pathogenic role of the airway epithelium in IPF is unknown. Combining biophysical, genetic, and signaling analyses of primary airway epithelial cells, we demonstrate that healthy and IPF airway epithelia are biophysically distinct, identifying pathologic activation of the ERBB-YAP axis as a specific and modifiable driver of prolongation of the unjammed-to-jammed transition in IPF epithelia. Furthermore, it is demonstrated that this biophysical state and signaling axis can direct epithelial-driven activation of the underlying mesenchyme. Molecular modulators of the unjammed-to-jammed (UTJ) transition are identified. The UTJ transition is a tissue-wide transition from a fluid-like (motile) to solid-like (non-motile) state that has been implicated in vertebrate body-axis elongation, metastasis, and asthma pathogenesis. This transition from a motile to non-motile state occurs without epithelial dedifferentiation or loss of cellular density. By pretreating proximal cultures with a SRC family kinase inhibitor (SFK), e.g. Saracatinib, or a YAP inhibitor, e.g. Verteporfin, our data revealed that SRC and YAP signaling are regulators of unjamming across multiple models of induced-epithelial dysfunction without compromising epithelial barrier function and that IL-6 family cytokine signaling converges on SRC/YAP activation to achieve epithelial fluidization in proximal jammed epithelia.

The data illustrate the active mechanisms regulating airway epithelial-driven fibrosis, highlighting a previously underappreciated tissue in disease pathogenesis and identifying targets to modulate disease progression. In an aspect, a method of screening a test compound for induction of an unjammed-to-jammed transition (UJT) in fibrotic primary human bronchial epithelial cells (HBECs) isolated from a subject with a fibrotic lung disease comprises culturing the fibrotic primary HBECs at an air-liquid interface (ALI) for a time sufficient to provide a differentiated pseudostratified epithelium; contacting the cultured cells with the test compound; and monitoring the motility of the cultured cells to identify the cultured cells as moving or stationary; wherein stationary cultured cells indicate that the test compound induces the UJT. ALI refers to the air liquid interface generated by removing the fluid from cultured epithelial cells to induce differentiation of basal epithelial cells into an organotypic culture closely resembling the epithelial layer of human airways. Well-differentiated primary human bronchial epithelia grown in an ALI culture model system are known to recapitulate the cellular constituency and architecture of intact human airway epithelia.

Exemplary test compounds antibodies, small molecule inhibitors, drugs, natural or synthetic mucosal protective agents, cytokines, growth factors, antioxidants, and the like. Libraries of test compounds may be screened. The test compound may be added to the ALI culture at any time during culture. In an aspect, either before or after screening, the test compounds are assessed for the ability to decrease expression of MUC5B. Increased expression of MUC5B is a risk factor for fibrotic disease progression of the distal airway epithelium.

In another aspect, a method of identifying a lung fibrosis biomarker associated with induction of an unjammed-to-jammed transition (UJT) in fibrotic primary human bronchial epithelial cells (HBECs) isolated from a subject with a fibrotic lung disease comprises culturing the fibrotic primary HBECs at an air-liquid interface for a time sufficient to provide a differentiated pseudostratified epithelium; contacting the cultured cells with the biomarker or an expression vector for the biomarker; and monitoring the motility of the cultured cells to identify the cultured cells as moving or stationary; wherein stationary cultured cells indicate that the biomarker induces the UJT.

In an aspect, the fibrotic primary HBECs are isolated from a subject with idiopathic pulmonary fibrosis (IPF), rheumatoid arthritis-associated interstitial lung disease (RA-ILD), chronic hypersensitivity pneumonitis, autoimmune related pulmonary fibrosis, drug-induced pulmonary fibrosis, radiation-induced pulmonary fibrosis, environmental pulmonary fibrosis (hypersensitivity pneumonitis), or occupational fibrosis (caused by exposure to asbestos, coal, etc.). In a preferred aspect, the fibrotic primary HBECs are isolated from a subject with idiopathic pulmonary fibrosis (IPF).

In an aspect, the HBECs are from less than 2 mm diameter airways.

Methods for culturing cells such as HBECs at an air-liquid interface are known in the art. HBECs can be seeded directly onto a porous support selected for ALI culturing, e.g., a collagen I coated transwell culture insert. Porous membrane inserts may be used which may be either precoated or may be coated with collagen I. The porous support will then be taken to the air-liquid interface for air-liquid interface culturing to promote cell differentiation and epithelium formation. By culturing HBECs at an air-liquid interface, the cells can be caused to differentiate to provide a fully differentiated epithelium resembling airway epithelium in vivo.

In an aspect, the time to culture the HBECs at an air-liquid interface to provide a fully differentiated pseudostratified epithelium is at least 14 days. Shorter times are possible to provide a particular cell type (i.e. basal or goblet/secretory), for example airway epithelial cells seeded as basal cells differentiate into goblet/secretory cells at 5-9 days, and differentiate into multiciliated cells at 12-16 days.

The cultured cells are then contacted with the test compound or the biomarker or an expression vector for the biomarker for a time sufficient to induce a UJT in the cells. Exemplary time periods include hours (i.e., 2 hours with ligand treatment) in all systems assessed.

Monitoring the motility of the cultured cells to identify the cultured cells as moving or stationary can comprise microscopy, time-lapse imaging microscopy, fluorescence microscopy, multi-photon microscopy, quantitative phase microscopy, surface enhanced Raman spectroscopy, videography, manual visual analysis, automated visual analysis, traction force microscopy, and combinations thereof. Automated time-lapse microscopy of live cells in vitro is a well-established method for spatiotemporal recording of cells and biomolecules, and tracking multi-cellular interactions. In some aspects, the monitoring occurs manually. In some aspects, the monitoring occurs automatically. In some aspects, the monitoring occurs automatically through the use of algorithms. For instance, in some aspects, the monitoring occurs through the use of automated quantification of cell movement through automated algorithms that measure the onset time, duration, frequency, and extent of the dynamic behavior.

In an aspect, determining if the cultured cells are moving or stationary comprises quantifying acellular mean-squared displacement (MSD) and an overlap parameter (Q). These physical parameters are inherent to the epithelium, or all motile systems and have characteristic values indicating the physical state.

In an aspect, the cultured fibrotic primary HBECs are cultured in a multi-well plate, and a plurality of test compounds or biomarkers are screened or identified, for example in medium or high-throughput screening. Exemplary plates include 2, 6, 12, 24, 48, 96, 384, or 1536 individual wells.

In another aspect, the multi-well plate is in communication with a microfluidic system for inflow and outflow of reagents.

In another aspect, a method for inducing UJT transition in HBECs using IL-6 cytokine modulators, direct inhibition of IL-6 or IL-6 family cytokines, i.e., interleukin-6, interleukin-11, oncostatin-M, and/or inhibition of downstream targets such as YAP and SRC.

IL-6, or interleukin 6, is a soluble cytokine that has an effect on inflammation, immune response, hematopoiesis, and differentiation or proliferation of several nonimmune cells. It is also known as BSF-2, HSF, HGF, or IFN-β2. IL-6 receptor, IL-6R, is a unique binding-receptor for IL-6, however IL-6 also forms a ligand-receptor complex with soluble isoforms of the IL-6R (sIL-6R) which are generated by alternative splicing or by limited proteolysis. The sIL-6R ligand-receptor complex with IL-6 is capable of stimulating a variety of cellular responses including proliferation, differentiation and activation of inflammatory processes. Glycoprotein 130, gp130, a type I cytokine receptor, is a signal-transducing chain shared by members of the IL-6 family of cytokines, that is, leukemia inhibitory factor, oncostatin M, ciliary neurotrophic factor, IL-11, cardiotrophin 1, cadiotrophin-like cytokine, IL-27, and IL35. Although these cytokines bind to their specific binding receptors, they use the same gp130 for their signals. Activation of gp130 in turn triggers activation of downstream signaling molecules such as JAK, STAT3, MAPK, YAP, SRC.

Surprisingly, it was discovered that IL-6 cytokine stimulation of proximal epithelial cells is able to induce epithelial fluidization without compromising epithelial barrier function. The alveolar epithelium barrier of the lung maintains a surface for gas transfer while being continuously exposed to potentially hazardous environmental stimuli, both infectious and noninfectious, and is known to be central to lung diseases including IPF. The data also showed that SRC and YAP are essential for the acquisition of the fluid-like phenotype, where a jammed state can be induced by administering a composition comprising an inhibitor of YAP and/or an inhibitor of SRC activity.

As used herein, an 'inhibitor of YAP' is any compound that inhibits the activity of YAP (Yes-associated protein). The compound may reduce the binding or expression of the ligand AREG, reduce or inhibit phosphorylation of YAP, or reduce or inhibit, or interfere with transcriptional gene activation by YAP, or compounds that target proteins that are transcriptionally upregulated by YAP. Such compounds can include, but are not limited to, Lasaran dihydrexidine, DAPT Dibenzaepine, RGD Cilengitide, BHA 2.1, AIIB2, Forskolin, IBMX Rolipram, Wortmannin, Trametinib, temsirolimus pazopanib, metformin, Phenformin, Panobinostat, Quisinostat, Verteporfin, Fenamates benzisothiazole dioxides, Alkylthio-triazoles, Cyclic peptides, Celexoxib, Navitoclax, Thiostrepton, and others known in the art, As used herein, an 'inhibitor of SRC' is any compound that inhibits the activity of SRC (SRC proto-oncogene). The compound may block downstream IL-6 activation of SRC family proteins with SRC family kinase inhibitor (SFK). Such compounds can include but are not limited to, e.g., Saracatinib, Dasatinib, Ponatinib, PP1, PP2, Bosutinib, Masitinib, Rebastinib, Src Inhibitor 1, Pelitinib, SU6656, AZD0530 and SKI-1, CH6953755, and others known in the art.

The term 'respiratory' refers to the process by which oxygen is taken into the body and carbon dioxide is discharged, through the bodily system including the nose, throat, larynx, trachea, bronchi and lungs.

The term 'respiratory disease' or 'respiratory condition' refers to any one of several ailments that involve inflammation and affect a component of the respiratory system including the upper (including the nasal cavity, pharynx and larynx) and lower respiratory tract (including trachea, bronchi and lungs). Such ailments include pulmonary fibrosis (interstitial lung diseases), rhino sinusitis, influenza, sarcoidosis, bronchial carcinoma, silicosis, pneumoconiosis, ventilation-induced lung injury, congenital emphysema, bronchiectasis, nasal polyps, asbestosis, mesothelioma, pulmonary eosinophilia, diffuse pulmonary haemorrhage syndromes, bronchiolitis obliterans, alveolar proteinosis, collagen and vascular disorders affecting the lung, cough. Preferably pulmonary diseases involving inflammation including cystic fibrosis, pigeon fancier's disease, farmer's lung, acute respiratory distress syndrome, pneumonia, aspiration or inhalation injury, fat embolism in the lung, acidosis inflammation of the lung, acute pulmonary edema, acute mountain sickness, post-cardiac surgery, acute pulmonary hypertension, persistent pulmonary hypertension of the newborn, perinatal aspiration syndrome, hyaline membrane disease, acute pulmonary thromboembolism, heparin-protamine reactions, sepsis, status asthmaticus and hypoxia. The inflammation in the upper and lower respiratory tract may be associated with or caused by viral infection or an allergen.

The respiratory disease or condition may be associated with or caused by an allergen, such as house dust mite. The present invention finds particular application to allergic disease of the airway or lung and exacerbations of that disease, such as exacerbations resulting from viral infection (e.g. RSV infection).

A symptom of respiratory disease may include cough, excess sputum production, a sense of breathlessness or chest tightness with audible wheeze. Exercise capacity may be quite limited. In asthma the FEV1.0 (forced expiratory volume in one second) as a percentage of that predicted nomographically based on weight, height and age, may be decreased as may the peak expiratory flow rate in a forced expiration. In COPD the FEV1.0 as a ratio of the FVC is typically reduced to less than 0.7. In IPF there is a progressive fall in FVC. The impact of each of these conditions may also be measured by days of lost work/school, disturbed sleep, requirement for bronchodilator drugs, requirement for glucocorticoids including oral glucocorticoids.

The phrase 'a condition of the airway or lung involving fibrosis' or 'a condition of the airway or lung having a fibrotic component' includes any disease or condition where there is the formation or development of excess fibrous connective tissue (fibrosis) in the airway or lung thereby resulting in the development of scarred (fibrotic) tissue. This includes pulmonary fibrosis, lung fibrosis or Idiopathic pulmonary fibrosis (IPF). More precisely, pulmonary fibrosis is a chronic disease that causes swelling and scarring of the alveoli and interstitial tissues of the lungs. The scar tissue replaces healthy tissue and causes inflammation. This damage to the lung tissue causes stiffness of the lungs which subsequently makes breathing more and more difficult.

'Idiopathic pulmonary fibrosis (IPF)' is a specific manifestation of idiopathic interstitial pneumonia (IIP), a type of interstitial lung disease. Interstitial lung disease, also known as diffuse parenchymal lung disease (DPLD), refers to a group of lung diseases affecting the interstitium. Microscopically, lung tissue from IPF patients shows a characteristic set of histological features known as usual interstitial pneumonia (UIP). UIP is therefore the pathologic presentation of IPF.

Other diseases in which tissue or organs are associated with fibrosis due to excessive fibrosis of connective tissue include cirrhosis, myelofibrosis, myocardial fibrosis, and renal fibrosis.

The invention is further illustrated by the following non-limiting examples.

EXAMPLES

Materials and Methods

Antibodies: For immunofluorescence, the following antibodies were used: rabbit monoclonal anti-ERBB2 (Cell Signaling® Danvers, Massachusetts, 2165, 1:250), chicken polyclonal anti-KRT5 (BioLegend®, San Diego, California, 905901, 1:500), mouse monoclonal anti-Ki67 (Cell Signaling® Danvers, Massachusetts, 9449, 1:500), mouse monoclonal anti-MUC5B (Novus Biologics®, Littleton, Colorado, NBP2-50390, 1:5000), rabbit monoclonal anti-Vimentin (Cell Signaling® Danvers, Massachusetts, 5741, 1:100), rabbit monoclonal anti-YAP (Cell Signaling® Danvers, Massachusetts, 14074, 1:250), mouse monoclonal anti-FOXJ1 (Invitrogen, Waltham, Massachusetts, 14-9965-82, 1:500), goat polyclonal anti-FOXJ1 (R&D Systems®, Minneapolis, Minnesota, AF3619, 1:500), mouse monoclonal anti-MUC5AC (Invitrogen, Waltham, Massachusetts, MA5-12178, 1:200), rat monoclonal anti-SCGB1A1 (R&D Systems®, Minneapolis, Minnesota, MAB4218, 1:500), rabbit monoclonal anti-KRT8 (Abcam, ab53280, 1:100), rabbit monoclonal P-63 a (Cell Signaling®, Danvers, Massachusetts, 13109, 1:500), mouse monoclonal anti-alpha smooth muscle actin (Abcam, Cambridge, UK, ab7817, 1:500), Phalloidin-iFluor™ (Abcam, Cambridge, UK, ab176753, 1:2000). All secondary antibodies were purchased from ThermoFisher Scientific™ (Waltham, Massachusetts) and used at a concentration of 1:500. For western blotting, we used the following antibodies: rabbit monoclonal anti-E-cadherin (Cell Signaling®, Danvers, Massachusetts, 3195, 1:1000), rabbit monoclonal anti-N-cadherin (Cell Signaling®, Danvers, Massachusetts, 13116, 1:1000), rabbit monoclonal anti-Snail (Cell Signaling®, Danvers, Massachusetts, 3879, 1:1000, and goat polyclonal anti-beta-actin (Abcam, Cambridge, Massachusetts, ab8229, 1:500). All secondary antibodies were purchased from LI-COR®, Lincoln, Nebraska and used at a concentration of 1:10,000.

Immunofluorescence staining: Cells were fixed with 4% paraformaldehyde in PBS with calcium and magnesium for 30 minutes at room temperature. Cells were then washed with PBS and subsequently permeabilized (Triton™-X, at 0.1%) and blocked with 5% bovine serum albumin in PBS for 1 hour at room temperature. Cells were then incubated for >16 hours at 4 degrees with primary antibodies. Primary antibodies were aspirated, and cells were washed with PBS+0.1% Tween-20 at room temperature. Cells were then incubated for 1 hour at room temperature with secondary antibodies (1:500) and/or Phalloidin-iFluor™ 488 1:2000. Cells were stained with 4',6-diamidino-2-phenylindole at 1:20000 (BioLegend®, San Diego, California, 422801). Subsequently, transwell membranes, or hydrogels, were removed from the well and mounted on glass slides with Fluoromount-G® (SouthernBiotech™, Birmingham, Alabama, 0100-01). Slides were then visualized using an Olympus BX63 microscope (Olympus, Tokyo, Japan).

Epithelial Cell Culture: Primary human bronchial epithelial cells (HBECs) were obtained from two sources (1) provided by Dr. Hong Wei Chu at National Jewish Health, or (2) lung transplant collection at the University of Colorado Hospital (IRB protocol: 11-1664 or 18-0572). Epithelial cells from bronchial brushes or CT-guided dissection were expanded to passage 2 before being cultured at air liquid interface (ALI). Control (N=11), IPF (N=6), and COPD (N=3) were age matched and controls had no history of chronic lung disease (Table 1). Cells were seeded on 24-Transwell plates (Corning, Corning, New York, 3470) coated with type I collagen (Corning, Corning, New York, 354236) and maintained under submerged conditions for five to seven days until the cells reached confluence. Culture media was a 1:1 mixture of DMEM and BEBM (Lonza, Basel, Switzerland, CC170) supplemented with retinoic acid (Sigma-Aldrich, Germany, R-2625) nystatin (Sigma-Aldrich, Germany N1638), and bovine serum albumin (FisherSci, Thermo Fisher Scientific, Waltham, Massachusetts BP9703100). Once confluent, apical media was removed and maintained at ALI. HBECs began recapitulating the in vivo airway, with production of mucus (6-9 days after establishing ALI) and development of a pseudostratified epithelium. Cells were switched to a starvation media (lacking supplemental epidermal growth factor, hydrocortisone, and bovine pituitary extract) 24 hours prior to experimentation.

Inhibitors used and HBEC inhibitor treatment: The following compounds were utilized to assess modulation of cellular speed: Tyrphostin AG-1478 (Millipore Sigma, Burlington, MAT4182-5MG, 100 nM) and Erlotinib (Selleckchem, Houston, Texas, 57786, 100 nM) selective EGFR inhibitors; Mubritinib (Selleckchem, S2216, 100 nM) a selective ERBB2 inhibitor; Lapatinib (Selleckchem, Houston, Texas, S2111, 100 nM) an EGFR/ERBB2 dual inhibitor; OSU-03012 (Selleckchem, Houston, Texas, S1106, 1 μM) and GSK2334470 (Selleckchem, Houston, Texas, S7087, 1 μM) selective PDK1 inhibitor; LY294002 (Selleckchem, Houston, Texas, S1105, 5 μM) a selective PI3K inhibitor; MK-2206 (Selleckchem, Houston, Texas, S1078, 1 μM) a selective ATK1/2/3 inhibitor; Staltic (Selleckchem, Houston, Texas, S7024, 5 μM) a selective STAT3 inhibitor; Ruxolitinib (Selleckchem, Houston, Texas, S1378, 5 μM) a selective JAK1/2 inhibitor; Sotrastaurin (Selleckchem, Houston, Texas, S2791, 1 μM) a selective PKC inhibitor; Verteporfin (Tocris Bioscience, Bristol, UK, 5305, 1 μM) a selective YAP inhibitor; XMU-MP-1 (Tocris Bioscience, Bristol, UK, 6482, 1 μM) a selective MST1/2 inhibitor; SB431542 (Tocris Bioscience, Bristol, UK, 1614, 5 μM) a selective TGFBRI inhibitor; Amphiregulin neutralizing antibody (R&D Systems®, Minneapolis, Minnesota, MAB262, 30 μg/ml), Recombinant AREG (R&D Systems®, Minneapolis, Minnesota 262-AR), EGF (R&D Systems®, Minneapolis, Minnesota 263-EG), and TGF-α (R&D Systems®, Minneapolis, Minnesota, 239-A-100) EGFR agonists. For inhibitor, activator, and ligand treatments HBECs were cultured in a starvation media in the absence of EGF, hydrocortisone, and bovine pituitary extract for 24 hours prior to treatment initiation. Cells were then treated for 2-4 hours (with exception of AREG neutralizing antibody which was maintained in the culture media), media was aspirated, the wells were washed with warm PBS and then replaced with fresh starvation media without inhibitor/activator/ligand present, and subsequently imaged. For experiments that required subsequent media changes (96 hour) cells fresh starvation media was changed 48 hours afterwards.

Culture and treatment of HLFs: Primary human lung fibroblasts (HLFs) were obtained from control lungs not suitable for transplantation at National Jewish Health. Briefly, pieces of tissue were placed into a tissue-culture dish and weighed down by a coverslip. Cells were cultured in DMEM (Corning, Corning, New York, 10-013-cv) supplemented with L-glutamine (25-005-cl), penicillin/streptomycin (Corning, Corning, New York, 30-002-c1), and 10% fetal bovine serum (ATCC®, Manassas, Virginia, 30-2020). These fibroblasts were then sub-cultured in t-75 flasks. All HLFs used in this study (N=4) were seeded at passage 3. Experimentally, fibroblasts were seeded onto 3 kilopascal (kPa) hydrogels at a density of 7,500 cells/cm2 and cultured for 24 hours in DMEM supplemented with L-glutamine, P/S, and 10% FBS. Fibroblasts were then synchronized in DMEM supplemented with L-glutamine, P/S, and 0.1% FBS for 24 hours. Fibroblasts were then treated with HBEC starvation media from jammed non-IPF, unjammed non-IPF, or unjammed IPF cells for 72 hours. Conditioned basal media was changed every 24 hours. In the case of direct fibroblast inhibition (via SB431541, AREG neutralizing antibody, or a combination of the two inhibitors), HLFs were treated with starvation media from IPF HBECs supplemented with the appropriate inhibitor combination and was changed every 24 hours in accordance with the experimental design.

Quantitative RT-PCR Analysis: Total RNA was extracted using RNeasy® Mini kit (Qiagen, Hilden, Germany) and quantified by NanoDrop™ (ThermoFisher Scientific™, Waltham, Massachusetts).Reverse transcription was completed using the High Capacity cDNA Reverse Transcription Kit (Applied Biosystems™, Thermo Fisher Scientific™, Waltham, Massachusetts). Gene expression was analyzed by using TaqMan® Advanced Master Mix (Thermo Fisher Scientific™, Waltham, Massachusetts and TaqMan® assays. They were subsequently run in triplicate on the ViiA™ 7 Real-Time machine (Thermo Fisher Scientific™, Waltham, Massachusetts). Primer IDs were: β-ACTIN, Hs01060665_g1; MUC5B, Hs00861595_m1; MUC5AC, Hs01365616_m1; EGFR, Hs0176090_m1; ERBB2, Hs01001580_m1; ZEB1, Hs00232783_m1; SNAI1, Hs00195591_m1; VIM, Hs00185584_m1; CTGF, Hs00170014_m1; AREG, Hs00950669_m1; FN1, Hs01549976_m1; PDGFRA, Hs00998018_m1; PDGFA, Hs00234994_m1; PDGFRB, Hs01019589_m1; PDGFB, Hs00966522_m1; TGFBRI, Hs00610320_m1; TGFBI, Hs00998133_m1; COL1A1, Hs00164004_m1; ACTA2, Hs00426835; MMP3, Hs00968305_m1; MMP9, Hs00957562_m1; TIMP1, Hs01092512_g1; and TIMP2, Hs00234278_m1.

Immunoblotting: Cells were lysed in 2×Laemmli Sample Buffer (Bio-Rad™, Hercules, California, 1610737) supplemented with 5% β-mercaptoethanol, and 1×Halt Phosphatase Inhibitor Cocktail (ThermoFisher Scientific™, Waltham, Massachusetts, 78426) and boiled for 10 minutes. Protein quantification was completed using BCA assay and 30 μg of protein was added per lane to a 10% or 4-20% sodium dodecyl sulfate polyacrylamide gel (Bio-Rad™, Hercules, California) and transferred to a polyvinylidene difluoride (PVDF) membrane (MilliporeSigma™, Burlington, Massachusetts, IPVH00010). Membranes were then blocked for 1 hour at room temperature in Intercept™ Blocking Buffer (LI-COR™, Lincoln, Nebraska, 927-60001). Membranes were incubated overnight at 4° C. with primary antibody and subsequently incubated with secondary antibodies for 1 hour at room temperature. Band visualization was completed using the LI-COR Odysessy® CLx system (LI-COR™, Lincoln, Nebraska).

Barrier function measurements: The transepithelial electrical resistance (TEER) was assessed utilizing the Millicell® ERS-2 Voltohmeter (MilliporeSigma™, Burlington, Massachusetts, MERS00002). Briefly, cells were incubated with PBS with calcium and magnesium (at 37 degrees for 20 minutes prior to barrier measurement). The probe was inserted, and the resultant ohm reading was recorded. The final value was calculated by:

This value was subtracted by 100 (the resistance of a blank well) and multiplied by 0.33 (the surface area of a single well in a 24 well plate). A minimum of 3 wells were recorded per donor per treatment condition. These values were subsequently averaged per treatment and graphed.

In Situ Hybridization: RNAScope® detection mRNA was used to perform in situ hybridization according the manufacturer's protocol (Advanced Cell Diagnostics™, Hayward, California). Briefly, formalin-fixed paraffin embedded human lungs were cut into 5 μm thick tissue sections. Slides were deparaffinized in xylene, followed by rehydration in a series of ethanol washes. Following citrate buffer (Advanced Cell Diagnostics™) antigen retrieval, slides were treated with protease plus (Advanced Cell Diagnostics™) at 40° C. for 30 min in a HybEZ™ hybridization oven (Advanced Cell Diagnostics™). Probes directed against AREG mRNA and control probes were applied at 40° C. in the following order: target probes, preamplifier, amplifier; and label probe for 10 minutes. After each hybridization step, slides were washed two times at room temperature. mRNA detection was followed by immunofluorescent staining for basal cells (keratin 5 positive) and MUC5B protein. Slides were blocked in 5% BSA buffer for 1 hr at room temperature, incubated with primary antibodies over night at +4° C., stained with appropriate fluorescently labelled secondary antibodies and counterstained with 4',6-diamidino-2-phenylindole (DAPI) at 1:20000 (BioLegend™, San Diego, California 422801). Staining was visualized using an Aperio™ Vectra 8 whole slide scanner using a 20× lens (Leica™, Buffalo Grove, Illinois). For Keratin 5 and MUC5B detection in human lungs tissues were deparaffinized in xylene, followed by rehydration in a series of ethanol washes. Following citrate buffer antigen retrieval, slides were blocked in 5% BSA buffer for 1 hr at room temperature, incubated with primary antibodies over night at +4° C., stained with appropriate fluorescently labelled secondaries antibodies and counterstained with 4',6-diamidino-2-phenylindole (DAPI) at 1:20000 (BioLegend™, 422801). Staining was visualized using Zeiss 780 laser-scanning confocal/multiphoton-excitation fluorescence microscope with a 34-channel GaAsP QUASAR detection unit and nondescanned detectors for two-photon fluorescence (Zeiss™, Thornwood, New York).

AREG Protein Detection: Secreted AREG by the HBECs was determine by a Human Amphiregulin Quantikine ELISA kit DAR00 from R&D Systems™ (Minneapolis, Minnesota) following manufacturer instructions. Media from control (n=4) and IPF (n=4) HBECs were collected at various days of differentiation as well as after treatment with inhibitors/activators. Three independent wells were per donor were used to determine concentration.

Immunofluorescence and cell number quantification for HBEC experiments: For total fluorescence quantification (i.e., ERBB2), all images were processed in the same manner with the same microscopy settings. To determine mean fluorescence the channel of interest was separated in ImageJ, and the mean gray value was measured for the field of view and normalized by the total number of cells. Cell counting was achieved by taking 40×images and manually counting all nuclei in a field of view (approximately 200-300). The number of cells also expressing the marker of interested were then counted and normalized by the total number of cells per field. For each experiment a biological n≥3 was used with at least 5 fields of view per well and at least 2 wells being counted in total per donor.

Immunofluorescence and cell number quantification for HLF experiments: For fluorescence quantification, (i.e., vimentin or alpha-SMA) images were all processed using the same settings. Fluorescence intensity was determined by channel separation and measurement of mean gray value for the field and normalized to total cell number. Cell number was determined by automated counting in ImageJ. For each experiment a biological n=4 was used with at least 10 fields of view per hydrogel and 3 hydrogels counted per donor.

Live Cell Imaging and Dynamics Measurement: To assess cellular dynamics, time-lapse microscopy and subsequent analysis were completed. Two imaging schemes were utilized: (1) images were taken every 5 minutes for 200 minutes during HBEC differentiation; (2) images were taken every 20 minutes for 48, 96, or 144 hours after HBEC experimental intervention. Phase contrast images were acquired on a Keyence BZ-X810 with a stage incubator (37° C., 5% $CO_2$). Dynamic analysis followed previously published workflows (10-12, 22). Briefly, using phase contrast images instantaneous velocities were mapped by particle image velocimetry utilizing open source PIVLab on MATLAB. Velocity fields were obtained with 2 passes (64×64 and 32×32 pixel size interrogation window with 50% overlap) with a pixel size of 0.75488 μm using a Fast Fourier Transformation method. Trajectories from the PIV were seeded onto a grid and obtained via forward-integration of subsequent fields. These values were then used to determine mean-squared-displacement (MSD) and self-overlap order parameter (Q): MSD(Δt)= ⟨ ri(t+Δt)−ri(t)|2 ⟩ and Q(Δt)= N−1ΣwiNi=1 as previously published. Instantaneous room mean squared velocity (VRMS) of the monolayer was obtained as previously published:

$$VRMS(t)=\sqrt{1/M}\Sigma \langle |v(t)2 \rangle_{jMj=1}$$

Cell Shape Analysis: Cell shape measurements were achieved via cell border delineation by F-actin immunofluorescence. Images were segmented utilizing SeedWater Segmenter. Similar to previously published workflows, we segmented images which were subsequently analyzed in ImageJ for the shape index (q=Perimeter/√Area) and aspect ratio (major and minor axis) for all cells within a given field of view. For each experimental condition an n≥3 was used with at least 3 independent wells per donor per treatment condition. Images were acquired at 40× with approximately 300 cells/field of view in each image. At least 3000 cells were segmented for each experimental condition. To color code aspect ratios, we adapted ImageJ ROI Color Coder.

Human Lung Specimens: Lung specimens from patients with idiopathic pulmonary fibrosis (IPF) and unaffected controls were obtained from the NHLBI Lung Tissue Research Consortium (LTRC; https://ltrcpublic.com/). All protocols were approved by local Institutional Review Boards and individuals gave written, informed consent to participate.

RNA-Seq preparation and analysis: Total RNA was extracted using RNeasy™ Mini Kit (Qiagen™, Hilden, Germany). RNA quality was assessed using the Agilent 2200 TapeStation system (Agilent™, Santa Clara, California). mRNA libraries were prepared from 500 ng total RNA with TruSeq™ stranded mRNA library preparation kits (Illumina™, San Diego, California) and sequenced at the averaged depth of 92.4 M reads on the Illumina® NovaSeq 6000 (Illumina). RNA paired-end reads were aligned at the transcript level to Ensembl GrCh38 using Kallisto with the average mapping rate 90.1%. 120,425 transcripts were detected in the mRNA dataset using Gencode v27. Differential expression was assessed using DESeq2. Comparison across and between control and IPF samples at days 4, 8, and 14 of ALI were performed with additional comparisons within control and IPF groups at different timepoints (i.e. Control day 4 vs Control day 8). Benjamini-Hochberg false discovery rate (FDR)-adjusted p-values<0.05 were considered significant. Pathway enrichment analyses were performed in Enrichr and network analysis was done in Network Analyst using the tissue-specific (lung) interactome dataset, only the largest network was considered.

Poly(ethylene glycol)-norbornene (PEG-NB) Synthesis: Norbornene-functionalized poly(ethylene glycol) was synthesized as described in the art. Briefly, PEG-hydroxyl (PEG-OH; MW 40 kg/mol, 8-arm, hexaglycerol core; JenKemUSA, Plano, Texas) was combined with a 5×molar ratio of pyridine (Thermo Fisher Scientific™, Waltham, Massachusetts) and a 0.5×molar ratio of 4-(dimethylamino)pyridine (DMAP; Sigma-Aldrich™, Germany) with respect to PEG hydroxyls in dichloromethane (DCM; Thermo Fisher Scientific™). In a separate flask, a 10×molar ratio of 5-norbonene-2-carboxylic acid (NBCA; Sigma-Aldrich™) and a 5×molar ratio of N,N'-dicyclohexylcarbodiimide (DCC; Sigma-Aldrich™) with respect to PEG hydroxyls were added to DCM and stirred for 30 minutes at room temperature under argon (Airgas®, Hartford, Connecticut). The solution of PEG-OH and pyridine was added to the solution of NBCA and DCC and stirred for two days under argon. The reacted PEG-NB solution was then filtered through Celite 545 (EMD Millipore, MilliporeSigma, Burlington, Massachusetts) soaked with DCM in a fitted glass funnel under vacuum and washed three times with 5% sodium bicarbonate (Sigma-Aldrich™) in a separatory funnel. PEG-NB solution was precipitated in ice-cold diethyl ether (Thermo Fisher Scientific™). The solution was then centrifuged at −10° C. and 4700 rpm for 10 minutes. The supernatant was decanted off, the precipitate resuspended in ice-cold diethyl ether, and the centrifugation process repeated twice. The product was dried under vacuum overnight at room temperature. This product was then dialyzed in deionized water for four days at room temperature with daily water changes. Dialyzed product was then frozen and lyophilized until dry.

Photoinitiator Synthesis: Lithium phenyl (2,4,6-trimethylbenzoyl) phosphinate (LAP) photoinitiator was synthesized as described in the art. Briefly, equimolar amounts of dimethyl phenylphosphonite (Alfa Aesar, Thermo Fisher Scientific™, Haverhill Massachusetts) and 2,4,6-trimethylbenzoylphosphonite (Acros Organics BVBA, Thermo Fisher Scientific™, The Hague) were added to a round-bottom flask and stirred overnight at room temperature under argon. A 4×molar ratio of lithium bromide (Acros Organics) with respect to dimethyl phenylphosphonite was dissolved in 2-butanone (Acros Organics) in a separate vessel. The reaction was stirred until all components dissolved and this solution was added to the round-bottom flask containing dimethyl phenylphosphonite and 2,3,6-trimethylbenzoylphosphonite. This reaction was heated to 50° C. until a precipitate formed (about 10 minutes). The reaction solution was cooled to room temperature over the course of an hour, filtered through filter paper moistened with 2-butanone in a Buchner funnel under vacuum, and rinsed thrice with 2-butanone. LAP product was dried under vacuum overnight at room temperature, dissolved in deionized water, frozen, and lyophilized until dry.

Hydrogel Fabrication: PEG-NB hydrogels were polymerized using methods known in the art. The hydrogel prepolymer solution was created by combining 5 wt % 8-arm, 40 kg/mol PEG-NB, dithiothreitol (DTT; Sigma-Aldrich™, Germany), 0.05 wt % LAP, and 2 mM of CGRGDS (SEQ ID NO:1) peptide in sterile phosphate buffered saline (PBS, pH=7.2; Life Technologies™, Carlsbad, California). Glass coverslips (18 mm; Thermo Fisher Scientific™, Waltham, Massachusetts) were sialanated with (3-mercaptopropyl)trimethoxysilane (Acros Organics, BVBA, Thermo Fisher Scientific™, The Hague) using a liquid-deposition technique. Hydrogels were photopolymerized in 90 µL drops placed between hydrophobic glass slides treated with SigmaCote® (Sigma-Aldrich™, Germany) and sialanated 18 mm cover slips under 365 nm light at 10 mW/cm$^2$ for 5 minutes. Hydrogels were then swollen in complete medium at 37° C. overnight prior to use in experiments.

Hydrogel Mechanical Characterization: The elastic modulus (E) of swollen hydrogel samples was measured as described in the art. Briefly, cylindrical hydrogel samples (volume=50 µL) were polymerized between hydrophobic glass slides separated by a 0.5-mm silicone gasket, allowed to swell to equilibrium in PBS, and then cut to 8-mm diameter with a circular punch. The storage (G') and loss moduli (G") were measured for four replicates by loading hydrogel samples between an 8-mm parallel plate and a Peltier plate heated to 37° C. on a Discovery Hybrid Rheometer 2 (TA Instruments). The gap distance between the plate and the geometry was adjusted until the G' measurement plateaued, and this percent compression was used for all samples. Samples were subjected to shear at 1% strain through a dynamic angular frequency range of 0.1 to 100 rad/s. Rubber elasticity theory was used to calculate E from G' assuming a Poisson's ratio of 0.5, corresponding to an incompressible material.

Statistics and reproducibility: Data were either analyzed in PRISM or MATLAB with custom scripts. Statistical significance was determined via either an ANOVA or multiple T-tests. For the ANOVA a Kruskal-Wallis test was performed with post-hoc Dunn test ($p<0.05$ was considered statistically significant). For multiple t-tests analysis was corrected using the Holm-Sidak test with statistical significance $p<0.05$. For single t-tests a Mann-Whitney test was used with statistical significance $p<0.05$. HBEC experiments were performed with at least n≥3 donors, whereby cells were grown in the same methods. A n≥3 wells was used per donor for each experimental condition. FIG. 5 describes donor information as well as the experiment where the cells were utilized. Fibroblast experiments utilized n=4 donors for all experiments and each condition was replicated over at least 3 independent hydrogels. Cell dynamics experiments were averaged over 4 positions per well, with a minimum of 3 wells per treatment condition. Experiments were repeated at least 3 independent times and results were averaged over all repeats.

Example 1: Jamming is Dysregulated in IPF Epithelia

Healthy and IPF lungs display significant differences in basal (KRT5) and mucus (MUC5B)-producing cells in the small airways (FIG. 1A). To understand this further, we obtained primary human bronchial epithelial cells (HBECs) from individuals without a history of lung disease and individuals with a diagnosis of Table 1 These cells were cultured at air-liquid-interface (ALI) for 14 days until a well-differentiated pseudostratified epithelium was achieved (FIG. 1B). We found that IPF epithelia recapitulated in vivo lung phenotypes with increased expression of KRT5 and MUC5B (FIG. 1C). Additionally, epithelia pre- and post-establishing ALI demonstrated differences in cellular differentiation rate, composition, and barrier function, but not in proliferation or basal cell subtypes in healthy and IPF epithelia (FIG. 2A-E).

TABLE 1

Primary cell donor information. List of cell type, passage, age, sex, smoking history, and MUC5B variant status used for all experiments.

| Disease Status | Cell Type | Passage | Age | Sex | Smoking History | Isolation Method | Region | Rs35705950 | Assays Used |
|---|---|---|---|---|---|---|---|---|---|
| Control | E | 2 | 62 | Male | Former | Brushing | Distal | GG | Jamming, |
| Control | | | 58 | Male | Never | | airway | GG | RNASeq |
| Control | | | 49 | Male | Former | | | GG | Jamming |
| Control | | | 65 | Female | Former | | | GG | |
| Control | | | 58 | Male | Never | | | GG | |
| Control | | | 66 | Male | Never | | | GG | |
| Control | | | 68 | Female | Former | | | GG | |
| Control | | | 66 | Female | Former | | | GT | |
| Control | | | 61 | Male | Former | | | GT | |
| Control | | | 72 | Female | Never | | | GT | |
| Control | | | 66 | Male | Never | | | GT | |
| | | | 62 ± 6.23 | M 7:F 4 | Former 6:Never 5 | | Distal airway: 11 | GG 7:GT 4 | |
| Control | F | 3 | 56 | Male | Former | Dissection | | GG | Hydrogel |
| Control | | | 64 | Male | Never | | | GG | treatments |
| Control | | | 63 | Female | Never | | | GG | |
| Control | | | 72 | Female | Former | | | GG | |
| | | | 66.3 ± 6.23 | M 2:F 2 | Former 2:Never 2 | | | GG 4 | |
| IPF | E | 2 | 60 | Female | Former | Brushing | Distal | GG | Jamming, |
| IPF | | | 72 | Male | Never | | airway | GT | RNASeq |
| IPF | | | 70 | Male | Former | | | GT | |
| IPF | | | 65 | Male | Never | | | GG | |
| IPF | | | 62 | Male | Former | Dissection | Proximal | GT | Jamming, |
| IPF | | | 68 | Male | Never | | and Distal | GG | Proximal v |
| IPF | | | 58 | Male | Never | | Airway | GG | Distal Airway |
| | | | 65 ± 5.26 | M 6:F 1 | Former 3:Never 4 | | | GG 4:GT 3 | |
| COPD | E | 2 | 67 | Female | Former | Dissection | Distal | GG | Jamming |
| COPD | | | 68 | Male | Former | | Airway | GG | |
| COPD | | | 60 | Male | Former | | | GG | |
| | | | 64.3 ± 3.79 | M 2:F 1 | Former 3 | | | GG 3 | |

E = Epithelial,
F = Fibroblast

To understand how disease status alters this tissue layer, we investigated whether the unjammed to-jammed transition (UJT) was altered in the epithelia. The UJT is a tissue-wide transition from a fluid-like (motile) to solid-like (non-motile) state that has been implicated in vertebrate body-axis elongation, metastasis, and asthma pathogenesis. This transition from a motile to nonmotile state occurs without epithelial dedifferentiation or loss of cellular density. The fluid to-solid transition occurred by day 8 of ALI for control HBECs, while IPF cells persisted in the fluid state past day 14 of ALI. (FIG. 1D). These migratory differences were quantified via cellular mean-squared displacement (MSD) and an overlap parameter (Q), demonstrating a prolonged migratory phenotype present in IPF HBECs (FIGS. 1E and F). Structural measurements of the epithelia validate the occurrence of a jamming transition in control samples by day 8 with an average perimeter-to-area cell-border ratio (q) below the predicted transition value (p0=3.813) (FIG. 1G). Concordantly, the IPF epithelia maintain a culture-wide elongation of the epithelial cell bodies with higher migratory speeds, all indicating the occurrence of the UJT in control prior to IPF cells (FIG. 1H). This prolonged unjammed state in IPF epithelia is indicative of a persistent disruption in epithelial homeostasis.

We next asked whether airway epithelial dysfunction was anatomically restricted in IPF lungs. HBECs from proximal (>2 mm diameter) and distal (<2 mm diameter) airways were obtained from the same patient with IPF and followed through monolayer maturation. Large and small airways diverged around day 9 of ALI with large airways undergoing the UJT similar to control small airway epithelia, while IPF small airways persisted in the unjammed state past day 14 of ALI (FIG. 1I). These migratory differences were validated by MSD and Q confirming the persistence of the unjammed state only in IPF distal airways (FIGS. 1J and K). Additionally, cell shape index was consistent with migratory differences demonstrating cell-body elongation with concordant increases in speed (FIGS. 1L and M). These data indicate that the UJT is temporally preserved in IPF proximal airways but dysregulated in IPF distal airways.

Example 2: ERBB-YAP Activation is Sufficient to Induce Unjamming

To identify gene and signaling pathways related to the UJT in IPF, we performed bulk RNA sequencing of control and IPF HBECs at various ALI days across the UJT (FIG. 3A). We identified 38 genes associated with the unjammed state by comparing genes downregulated across the jamming transition in control HBECs (day 4-day 8) to genes upregulated in IPF HBECs (day 8 and 14) (FIG. 3B, C and data not shown). KEGG analysis of these 38 genes demonstrated an enrichment for MAPK signaling, ERBB signaling, and transcriptional regulation of cancer. Gene ontology analysis (biological process and molecular function) demonstrated an enrichment for genes involved in ERBB and growth factor signaling (Table 2, FIG. 3D).

TABLE 2

Genes correlated with the jamming transition in 802 primary human bronchial epithelial cells. Genes down regulated from day 4 to 8 in control HBECs that are upregulated in IPF HBECs at days 8 and 14 of ALI.

| Common "Jamming" Related Genes Control Day 4 → Day 8 of ALI | | |
|---|---|---|
| Gene Name | Control Day 4 (L2FC) | Control Day 8 (L2FC) |
| A2ML1 | 3.35968 | −3.35968 |
| ADAM17 | 2.36923 | −2.36923 |
| AFAP1L2 | 1.57346 | −1.57346 |
| AP2S1 | 1.32405 | −1.32405 |
| APOO | 2.73311 | −2.73311 |
| AREG | 1.51958 | −1.51958 |
| BEAN1 | 2.29793 | −2.29793 |
| C2CD4A | 1.45859 | −1.45859 |
| CACNA1H | 1.48804 | −1.48804 |
| DHRS9 | 2.10621 | −2.10621 |
| DUSP6 | 1.24182 | −1.24182 |
| ELP2 | 1.98565 | −1.98565 |
| ETV5 | 2.21254 | −2.21254 |
| FAM214B | 2.66521 | −2.66521 |
| GALNT14 | 1.02217 | −1.02217 |
| KIAA1549L | 1.59375 | −1.59375 |
| KRT16P2 | 2.11183 | −2.11183 |
| KRT17 | 2.59168 | −2.59168 |
| LGALS1 | 1.94015 | −1.94015 |
| LINC00704 | 1.39032 | −1.39032 |
| LIPG | 1.3435 | −1.3435 |
| OTUB2 | 1.79158 | −1.79158 |
| PAPPA | 2.30254 | −2.30254 |
| PDE4C | 1.56141 | −1.56141 |
| PHLDA1 | 1.38825 | −1.38825 |
| PRSS23 | 1.19527 | −1.19527 |
| PTK6 | 1.81366 | −1.81366 |
| PYCR1 | 2.84926 | −2.84926 |
| RAC2 | 2.26525 | −2.26525 |
| RHOF | 1.25856 | −1.25856 |
| SEPT9 | 1.80608 | −1.80608 |
| SERPINB5 | 1.60017 | −1.60017 |
| SCH1 | 1.72804 | −1.72804 |
| SPRED3 | 1.69745 | −1.69745 |
| SPRY4 | 1.65284 | −1.65284 |
| TM7SF2 | 2.10907 | −2.10907 |
| TRIM16 | 1.9556 | −1.9556 |
| YES1 | 9.6906 | −9.6906 |

| Common "Jamming" Related Genes Day 8 of ALI | | |
|---|---|---|
| Gene Name | Control Day 8 (L2FC) | IPF Day 8 (L2FC) |
| A2ML1 | −1.130477 | 1.130477 |
| ADAM17 | −1.701 | 1.701 |
| AFAP1L2 | −1.11 | 1.11 |
| AP2S1 | −1.206 | 1.206 |
| APOO | −1.695038 | 1.695038 |
| AREG | −1.337 | 1.337 |
| BEAN1 | −1.634 | 1.634 |
| C2CD4A | −1.305 | 1.305 |
| CACNA1H | −5.393318 | 5.393318 |
| DHRS9 | −1.359514 | 1.359514 |
| DUSP6 | −1.341 | 1.341 |
| ELP2 | −1.620609 | 1.620609 |
| ETV5 | −1.417 | 1.417 |
| FAM214B | −1.066 | 1.066 |
| GALNT14 | −1.006269 | 1.006269 |
| KIAA1549L | −2.124072 | 2.124072 |
| KRT16P2 | −1.567 | 1.567 |
| KRT17 | −1.531 | 1.531 |
| LGALS1 | −1.785 | 1.785 |
| LINC00704 | −2.176459 | 2.176459 |
| LIPG | −1.367 | 1.367 |
| OTUB2 | −1.031 | 1.031 |
| PAPPA | −2.261 | 2.261 |
| PDE4C | −1.78453 | 1.78453 |

TABLE 2-continued

Genes correlated with the jamming transition in 802 primary human bronchial epithelial cells. Genes down regulated from day 4 to 8 in control HBECs that are upregulated in IPF HBECs at days 8 and 14 of ALI.

| PHLDA1 | −1.035 | 1.035 |
| PRSS23 | −1.96 | 1.96 |
| PTK6 | −1.717 | 1.717 |
| PYCR1 | −2.591 | 2.591 |
| RAC2 | −1.096 | 1.096 |
| RHOF | −1.093947 | 1.093947 |
| SEPT9 | −1.931 | 1.931 |
| SERPINB5 | −1.371 | 1.371 |
| SCH1 | −1.185 | 1.185 |
| SPRED3 | −1.254 | 1.254 |
| SPRY4 | −1.289 | 1.289 |
| TM7SF2 | −1.493291 | 1.493291 |
| TRIM16 | −1.088076 | 1.088076 |
| YES1 | −8.143988 | 8.143988 |

Common "Jamming" Related Genes Day 14 of ALI

| Gene Name | Control Day 14 (L2FC) | IPF Day 14 (L2FC) |
| --- | --- | --- |
| A2ML1 | −4.822781 | 4.822781 |
| ADAM17 | −1.701 | 1.701 |
| AFAP1L2 | −1.11 | 1.11 |
| AP2S1 | −1.206 | 1.206 |
| APOO | −2.093187 | 2.093187 |
| AREG | −1.9431 | 1.9431 |
| BEAN1 | −1.634 | 1.634 |
| C2CD4A | −1.305 | 1.305 |
| CACNA1H | −4.893584 | 4.893584 |
| DHRS9 | −1.83051 | 1.83051 |
| DUSP6 | −1.341 | 1.341 |
| ELP2 | −1.272051 | 1.272051 |
| ETV5 | −1.417 | 1.417 |
| FAM214B | −1.066 | 1.066 |
| GALNT14 | −1.502481 | 1.502481 |
| KIAA1549L | −2.25629 | 2.25629 |
| KRT16P2 | −1.567 | 1.567 |
| KRT17 | −1.531 | 1.531 |
| LGALS1 | −1.785 | 1.785 |
| LINC00704 | −2.916479 | 2.916479 |
| LIPG | −1.367 | 1.367 |
| OTUB2 | −1.031 | 1.031 |
| PAPPA | −2.261 | 2.261 |
| PDE4C | −2.027821 | 2.027821 |
| PHLDA1 | −1.035 | 1.035 |
| PRSS23 | −1.96 | 1.96 |
| PTK6 | −1.717 | 1.717 |
| PYCR1 | −2.591 | 2.591 |
| RAC2 | −1.096 | 1.096 |
| RHOF | −1.883034 | 1.883034 |
| SEPT9 | −1.931 | 1.931 |
| SERPINB5 | −1.371 | 1.371 |
| SCH1 | −1.185 | 1.185 |
| SPRED3 | −1.254 | 1.254 |
| SPRY4 | −1.289 | 1.289 |
| TM7SF2 | −1.189712 | 1.189712 |
| TRIM16 | −1.900963 | 1.900963 |
| YES1 | −6.948261 | 6.948261 |

A network analysis of these conserved genes revealed protein-protein interactions between epidermal growth factor receptor (EGFR) and the inducible transcriptional co-activator, YES-associated protein (YAP) (FIG. 3E).

We validated these findings in vivo and in vitro and identified increases in amphiregulin (AREG) in IPF distal airways (FIG. 4A) and increases in ERBB2 protein and YAP nuclear localization in IPF epithelia (FIGS. 4C and D). Control and IPF epithelia demonstrated transcript level increases in ERBB family receptors and YAP target genes in the unjammed phase (FIG. 4E-H). This finding motivated the investigation of whether ERBB or YAP activation could induce unjamming in control epithelia. Control cells (at ALI day 14) were treated with a high-affinity (EGF or TGFα) or low affinity (AREG) EGFR ligands. We found that only AREG treatment had the ability to induce an unjammed state in control epithelia without diminishing barrier function (FIG. 5 A-F). Additionally, a small molecule (XMU-MP-1) inducer of YAP nuclear localization had the ability to elicit an unjammed state (FIGS. 5G and H). This AREG- and XMU-induced unjamming persisted for >48 hours (FIG. 4I-M). Further, neither AREG nor XMU treatment resulted in increased proliferation but did lead to YAP nuclear localization (FIG. 5I-L). EGFR and YAP activation are frequently associated with an epithelia-to-mesenchymal transition (EMT) which is a common modality of collective migration in epithelial layers. However, in our system, long-term treatment with EGFR or YAP activators did not elicit an EMT or partial-EMT phenotype when compared to TGFβ1 treatment (FIG. 6A-H). This finding is concordant with previous work demonstrating that airway epithelial unjamming is structurally, functionally, and physiologically distinct from EMT.

After XMU or AREG treatment at day 14 of ALI, the migratory capacity of control epithelia begins to diminish at ~36 hours, however, we found that dual treatment of AREG and XMU could sustain this migratory phenotype for >48 hours (FIG. 7A-E). We also treated HBECs at ALI day 28 and determined that this unjammed state was induced regardless of monolayer maturity (FIG. 7F-J). Interestingly, we identified that after XMU or AREG treatment, YAP nuclear localization was predominantly in multi-ciliated cells (FOXJ1+) (FIG. 8A-G). Staining of IPF lung tissue revealed FOXJ1+/YAP+ co-positive populations in small airways in regions of minimal fibrosis (FIG. 8H).

Example 3: ERBB-YAP Axis Specifically Regulates IPF Unjamming

Next, we sought to understand if the pathological unjammed state in IPF epithelia could be rescued through inhibition of these targets (EGFR or YAP). Utilizing day 14 IPF HBECs, we treated cells with AG1478 (EGFR inhibitor) or Verteporfin (YAP inhibitor). Treatment with either inhibitor halted migration and induced a cobblestone appearance in the epithelia indicating a shift in the biophysical state of the epithelia to a jammed state (FIG. 9A-E). Additionally, this targeted inhibition reduced the transcription of ERBB receptors, YAP target genes, and MUC5B nearly back to control levels (FIG. 9F-K).

Figure 11A:
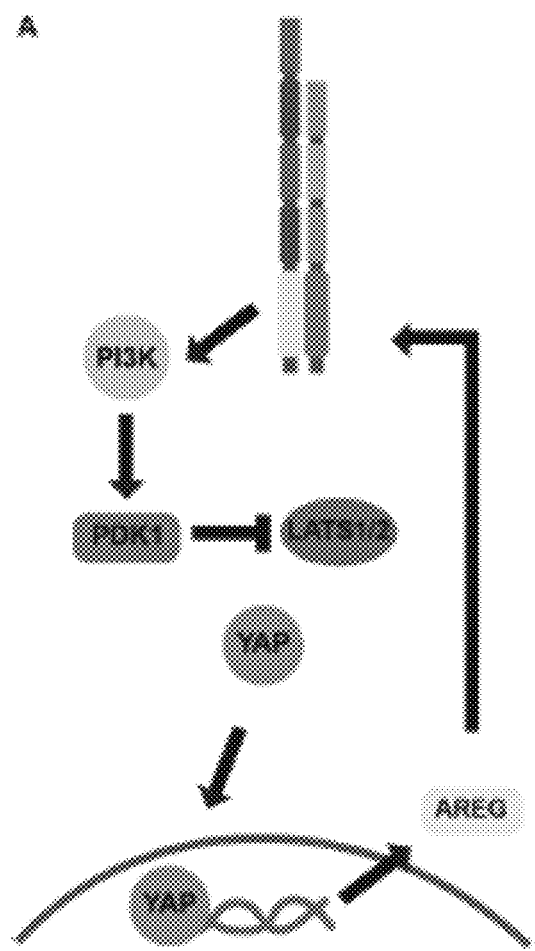
Figure 12A:
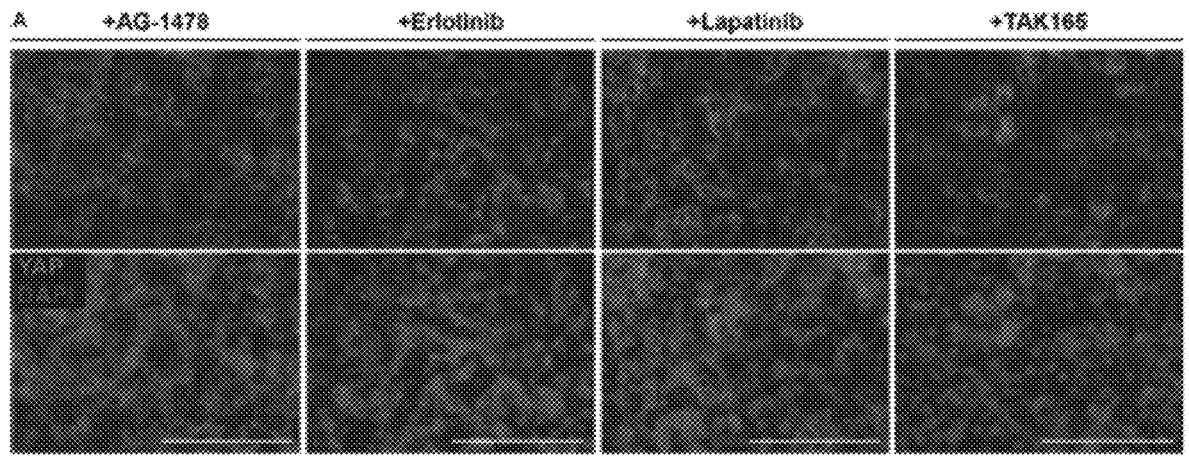
FIG. 12A-C show inhibition of the ERBB-YAP axis in IPF epithelia results in YAP nuclear exclusion. (12A) AG1478, Erlotinib, Lapatinib, or Mubritinib, (12B) GSK2334470 or OSU03012, (12C) LY294002, Verteporfin, or AREG neutralizing antibody immunofluorescence for YAP 48 hours after treatment of IPF HBECs, scale bars represent 100 μm.
Figure 12B:
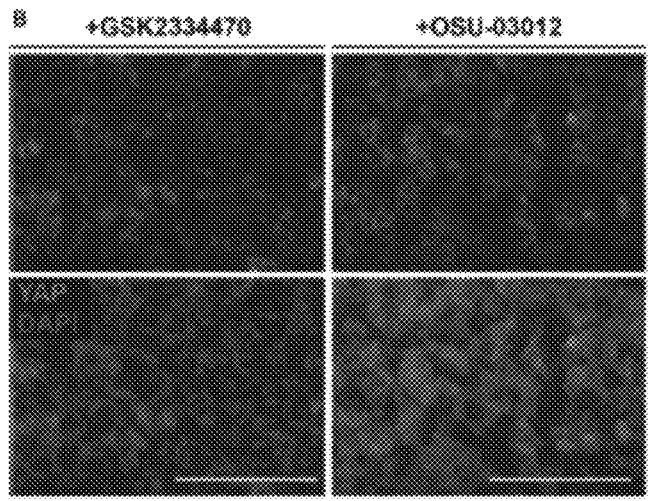
Figure 12C:
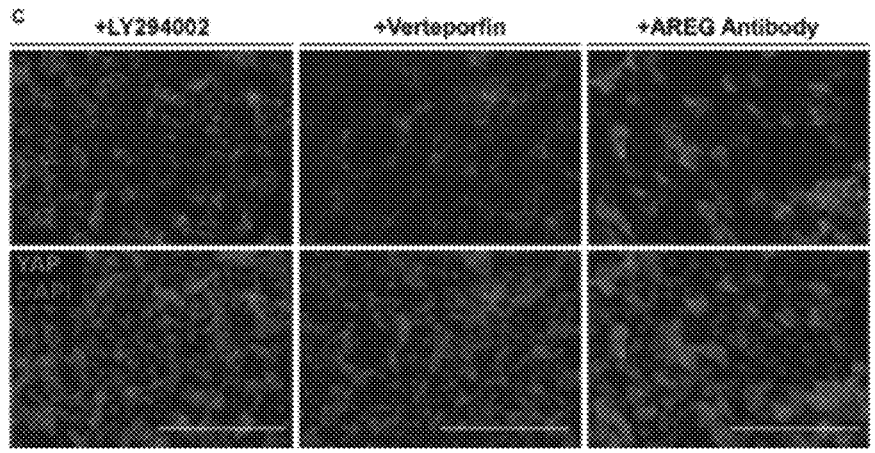
Figure 13A:
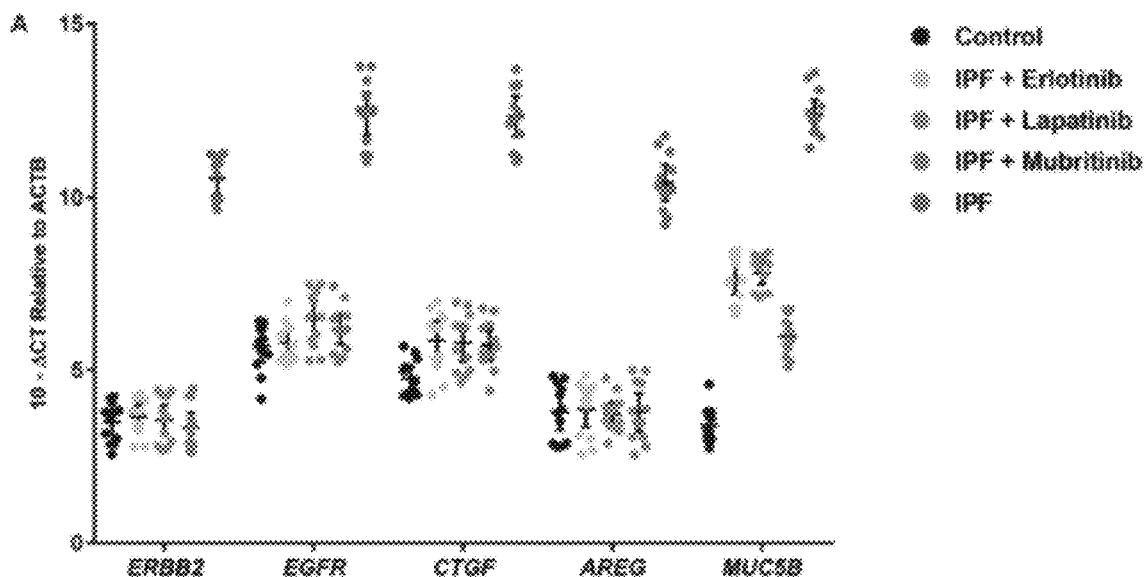
FIG. 13A-C show inhibition of the ERBB-YAP axis in IPF epithelia decreases 738 ERBB-YAP target gene expression. Gene expression of ERBB receptors (EGFR, ERBB2), YAP target genes (CTGF, AREG), and MUC5B 48 hours after treatment with (13A) Erlotinib, Lapatinib, or Mubritinib, (13B) GSK2334470 or OSU03012, or (13C) LY294002, Verteporfin, or AREG neutralizing antibody, error bars represent 95% CI.
Figure 13B:
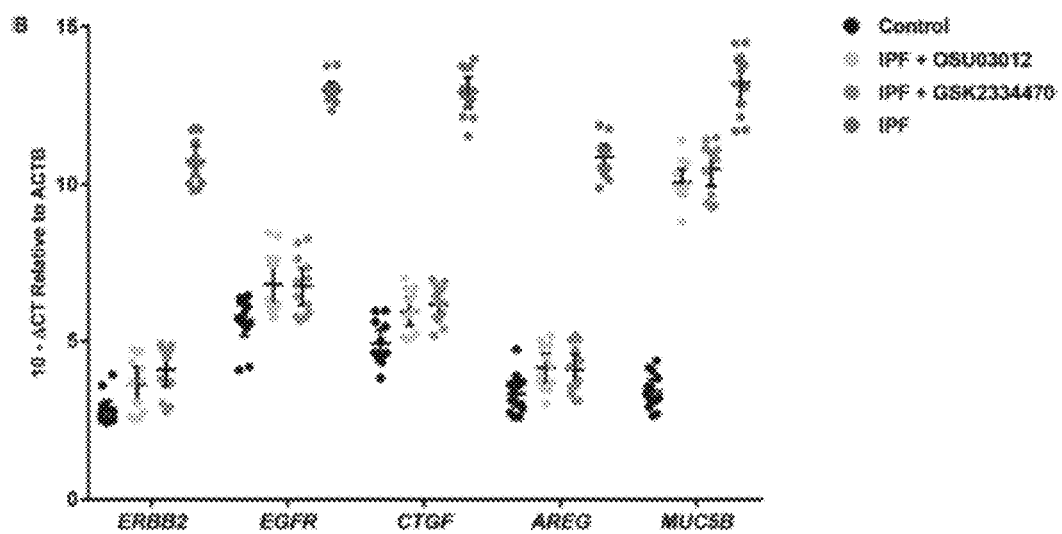
Figure 13C:
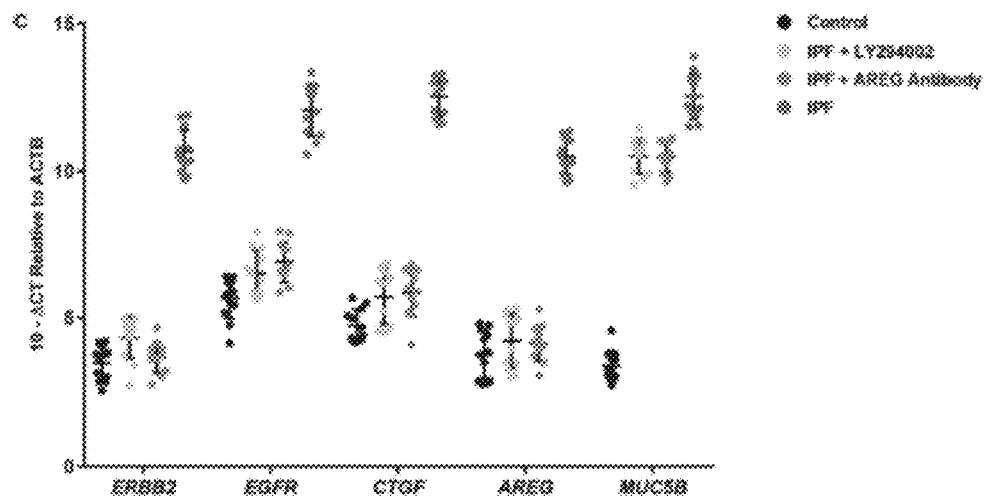

EGFR activation can signal to myriad of downstream effectors. We sought to understand the specificity of the EGFR activation in unjammed IPF epithelia and whether other downstream targets had the ability to induce a jammed state (FIG. 10A). Treatment with MK-2206 (AKT 1/2/3 inhibitor), Stattic (STAT3 inhibitor), Ruxolitinib (JAK1/2 inhibitor), or Sotrastaurin (pan-PKC inhibitor) did not induce the UJT in IPF epithelia (FIGS. 10B and C). Taken together, these findings indicated that the prolonged unjammed state induced by EGFR and YAP in IPF epithelia is likely not due to other downstream EGFR targets (i.e., AKT1/2/3, STAT3, JAK1/2, PCK), but instead is specific to the ERBB-YAP axis. ERBB-YAP signaling axis occurs via a PI3K-PDK1 directed mechanism which disrupts the ability of LATS1/2 to retain YAP in the cytoplasm (FIG. 11A). To determine the signaling requirements of EGFR-YAP prolonged unjamming in IPF, we utilized day 14 IPF HBECs and tested the ability of specific inhibitors in the EGFR-YAP axis to induce the UJT. Inhibition of the intermediate signaling effectors in the EGFR-YAP axis all induced the UJT, which when followed persisted for >144 hours after only the initial treatment (FIG. 11B-S. This inhibition was accompanied by concomitant exclusion of YAP from the nucleus and concordant gene expression (FIG. 12 and FIG. 13). Taken together, these data demonstrate the requirement of the EGFR-YAP signaling axis in maintaining a 136 hour prolonged unjammed state in IPF epithelia.

Figures 14D, 14E:
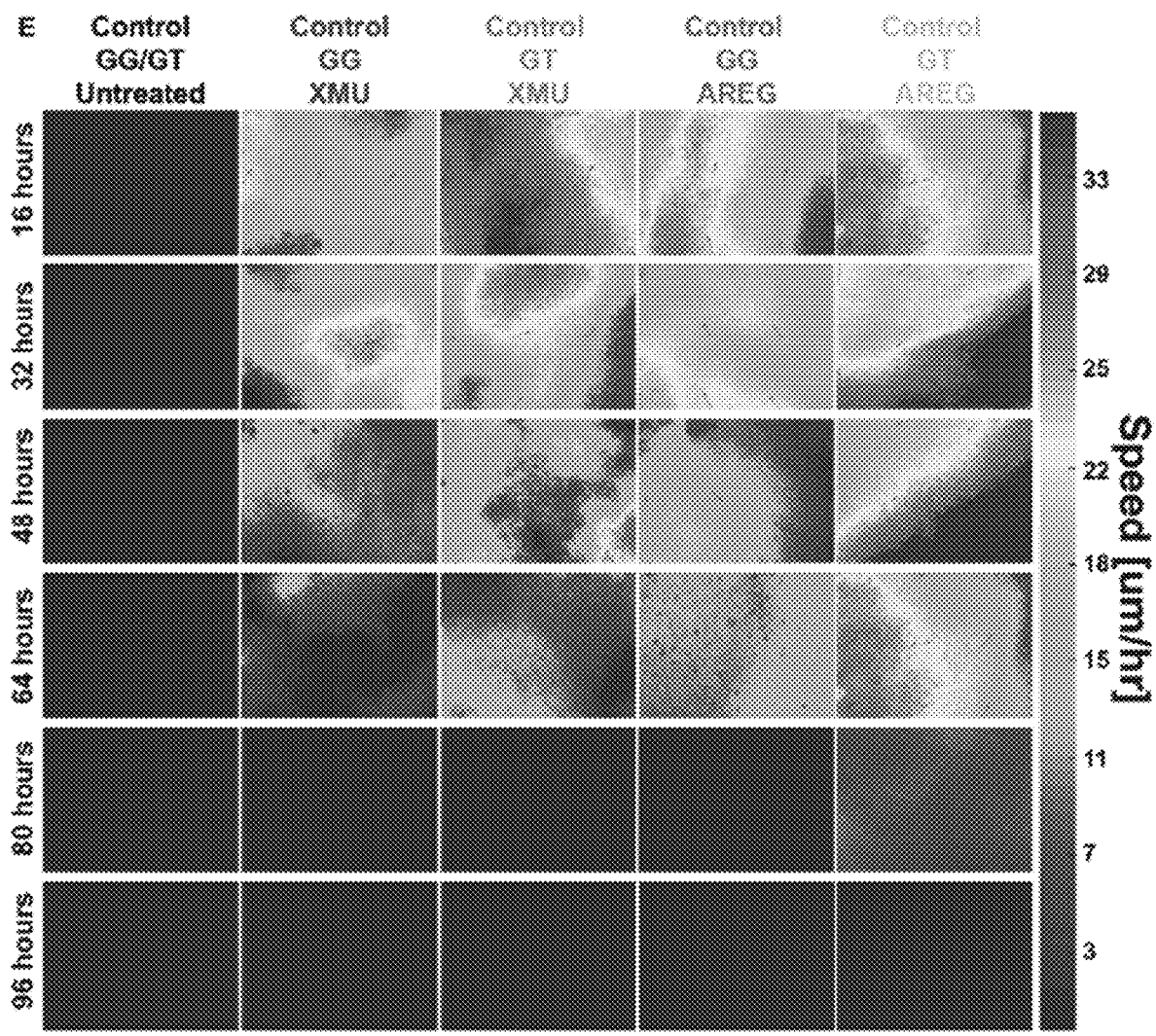

Example 4: Unjamming is Responsive to Genetic Risk Variants and is Disease Specific We next wanted to understand whether known genetic risk factors specific to IPF affected AREG or YAP-driven unjamming. The gain-of-function MUC5B promoter variant rs35705950 is the dominant genetic IPF risk variant which results in MUC5B overexpression in the distal airway epithelium. We treated control HBECs from individuals with no copies (GG) or one copy (GT) of the MUC5B promoter variant with AREG or XMU. Untreated HBECs persisted in the jammed state regardless of their MUC5B status, however, GT epithelia treated with AREG had a higher root-mean-squared velocity than their GG counterparts (FIGS. 14A and B). Additionally, GT epithelia treated with AREG persisted in the unjammed state significantly longer than GG epithelia (FIG. 14C-E). This genotype-dependent unjamming did not alter barrier function and was confirmed via cell shape measurements. These data demonstrate a MUC5B-driven differential response to AREG-induced unjamming in airway epithelia.

We then asked whether EGFR-YAP dependent unjamming was specific to IPF epithelia or if this axis was common among other chronic lung disease, such as chronic obstructive pulmonary disease (COPD). While COPD HBECs persisted in an unjammed state past day 14, inhibition of the EGFR-YAP axis failed to induce jamming (FIG. 15A-J). These data suggest that EGFR-YAP driven unjamming is specific to IPF and that COPD has a non-EGFR-YAP dependent mechanism regulating the unjammed state.

Example 5: Dynamics and Signaling Regulate Epithelial-Driven Fibrosis

Next, we evaluated whether IPF HBECs could induce a pro-fibrotic response in human lung fibroblasts (HLF). We found that AREG secretion into the basal media was increased in IPF and unjammed control HBECs (FIGS. 16A and B) and that this secretion was decreased in IPF HBECs after pharmacological jamming (FIG. 16C). This finding raised the question whether AREG could drive a pro-fibrotic state in fibroblast. To pursue this, we seeded healthy HLFs onto physiologically soft (3 kPa) hydrogels to prevent artificial activation of the HLFs (FIGS. 17A-D and 18). HLFs were treated with conditioned media from control (jammed), control+YAP (unjammed), control+AREG (unjammed), and IPF (unjammed) HBEC cultures (FIG. 19B-C). Treatment of HLF with conditioned media from control-unjammed or IPF-unjammed HBECs resulted in increases in the total number of fibroblasts and markers of activation when compared to control untreated epithelia (FIG. 19D-G). This treatment also induced significant gene expression changes in canonically pro-fibrotic genes (FIG. 20A-O). These data indicate that the pathologic unjamming of the epithelia activates fibroblasts in the surrounding mesenchyme.

We then asked whether AREG was the primary driver of this fibrotic response. We treated HLFs with IPF conditioned HBEC media supplemented with TGFBRI inhibitor (SB431542), AREG neutralizing antibody (iAREG), or SB431542+iAREG (FIG. 19H) and found that treatment reduced fibroblast activation (FIG. 19H-I and K-L). However, none of these treatments alone were able to fully rescue the increase in cell number or the associated pro-fibrotic gene expression (FIG. 19J and FIG. 21A-O). Interestingly, AREG inhibition induced a more significant differentiation-related rescue than TGFBRI inhibition alone (FIG. 19I-L). This supports our hypothesis that the epithelial driven fibrotic response seen in our system is multifactorial and that AREG plays a substantial role.

Next, we tested if direct inhibition of the epithelia had the ability to more robustly prevent the fibrosis-like phenotype observed. Conditioned media were collected from EGFR-, YAP-, and AREG-inhibited IPF HBECs 48 hours after treatment and was used to culture HLFs (FIG. 4M). Treatment significantly reduced HLF differentiation, decreased the total number of cells, (FIG. 19N-O and reduced HLF gene expression of canonically pro-fibrotic targets (FIG. 22A-O). Notably, direct targeting of unhealthy HBECs provides a more substantial rescue when compared to targeting fibroblasts.

Conclusions

Our results indicate that IPF distal airway epithelium plays an active role in driving fibrosis and is dynamically and structurally distinct from normal airway epithelia. Further, the ERBB-YAP axis provides a modifiable cascade to reverse the persistent biophysical defects of IPF epithelia. The unjammed state represents a biophysical property by which collective migration of epithelial layers can traverse large distances. Taken together, we propose that the biophysical properties of the airway epithelium are dynamic and actively participate in disease progression integrating signaling and genetic causes of pulmonary fibrosis.

Example 6

Utilizing explanted lung tissue from patients with idiopathic pulmonary fibrosis (IPF), we preformed CT-guided dissections of the airway tree, isolating airway epithelial cells from the proximal (cartilaginous airways), distal (respiratory airways), and honeycomb cyst epithelia (regions with microscopic honeycombing) within a single patient (FIGS. 23 A and B).

When these airway epithelial cells were cultured in vitro, we found that proximal cultures behave most similarly to healthy, control patient samples confirming our previous findings (FIG. 23C). Additionally, we identified that distal and honeycomb cultures persisted in a collective migratory phase (FIG. 23C). This fluid, or unjammed, phase has been characterized across development and disease, and has been used as a moniker for epithelial function; the unjammed phase describes a collective migratory, or fluid-like, characteristic of the epithelium in contrast to the jammed phase whereby cells are non-migratory, or static. Canonical dynamic measurements of this fluid-like phase confirmed the airway epithelial dysfunction was potentiated along the proximal-distal axis in IPF patients (FIG. 23 C-E). These dynamic measurements were also confirmed at the level of cell-structure with a persistently elongated cell shape across the epithelium in distal and honeycomb samples, whereas proximal cultures underwent this jamming transition to a solid-like phase characterized by the acquisition of a cobblestone-like epithelium (FIG. 23F-H).

Figure 24C:
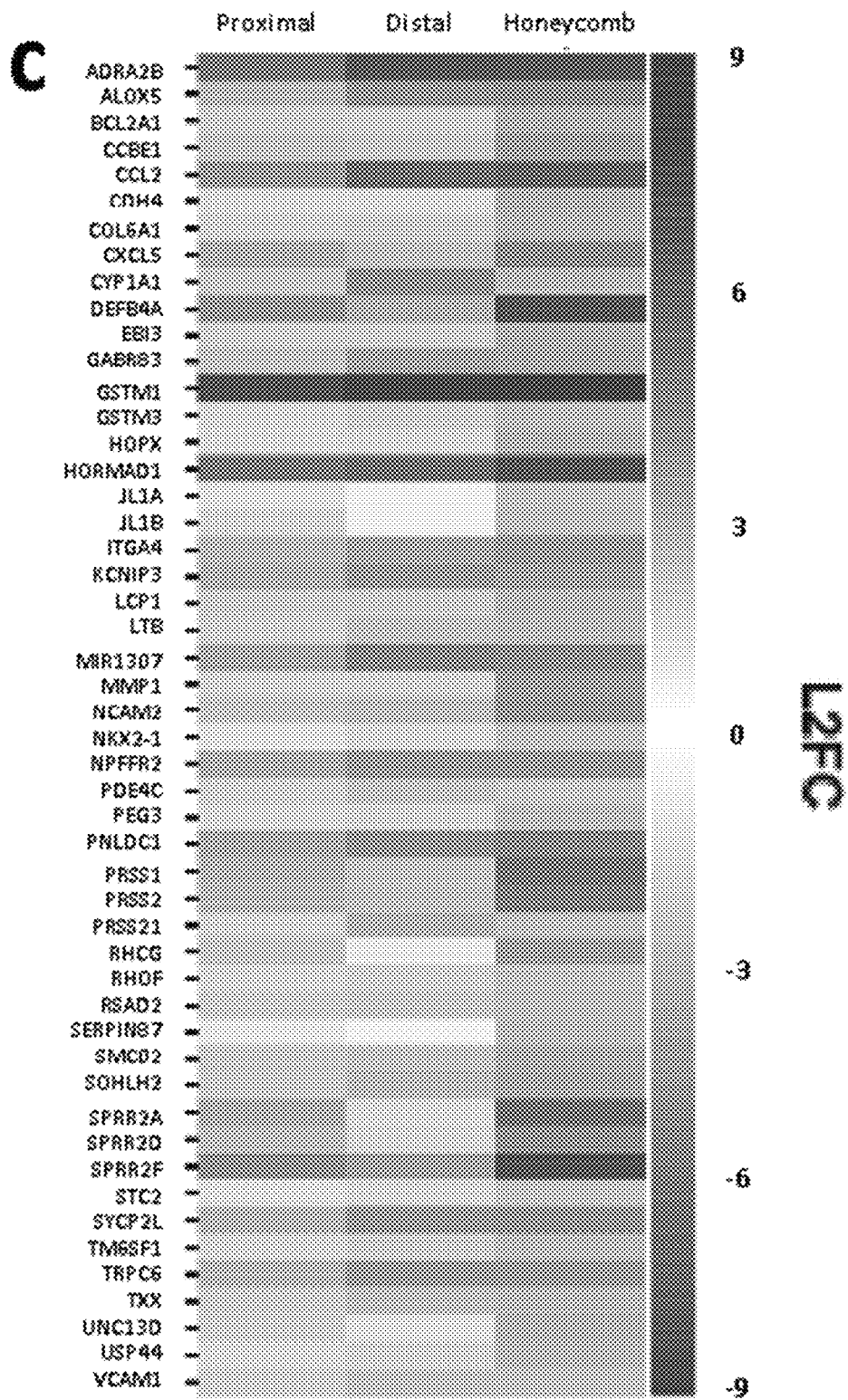
FIG. 24A-O show epithelia from distal or honeycomb regions express distal-like airway epithelial genes. (24A-F) Cytokine stimulated proximal, jammed cultures with IL-6 family cytokines is able to induce epithelial fluidization without compromising epithelial barrier function. (24H) Pretreated proximal cultures with inhibitors of downstream IL-6 genes followed by stimulation with IL-6 revealed JAK/STAT signaling is dispensable for IL-6 family cytokine induced unjamming. (24I-O) SRC and YAP are essential for the acquisition of unjammed fluid-like phenotype measured by cell dynamics (24I-K) and shape (24L-N). (24O) KRT5+ and YAP increase in nucleus of cells after IL-6 family cytokine stimulation.

To identify the molecular regulators of this biophysical dysfunction along the intra-airway proximal-distal axis, we preformed bulk RNA-sequencing. We initially identified that epithelia from distal or honeycomb regions expressed previously reported 'distal-like' airway epithelial genes (FIG. 24A-C). This suggested to use that the airway epithelia cultured from these various genes indeed maintain the in vivo characteristics when cultured in vitro. We then compared genes down-regulated across this jamming transition in proximal epithelia, to genes persistently upregulated in distal and honeycomb cultures, we identified 660 conserved genes (FIG. 24A). These conserved genes were enriched for previously identified pathways in IPF (i.e., HIPPO and ERBB signaling); interestingly, however we also identified a strong signature for genes enriched for cytokine-mediated signaling and cellular responses to cytokine stimuli (FIGS. 24B and C). Specifically, within this cytokine-enriched category, we identified a strong interleukin-6 (IL6)-family signature. IL-6 family cytokines (i.e., interleukin-6, interleukin-11, oncostatin-M) signal through heterodimerization with a shared receptor, glycoprotein 130 (gp130), and a ligand-specific receptor (e.g., interleukin-6 receptor, interleukin-11 receptor, oncostatin-M receptor). This prompted the question of whether IL-6 family cytokine stimulation could induce this pro-repair unjammed phenotype in healthy proximal cultures. To answer this question, we stimulated proximal, jammed cultures with IL-6 family cytokines and identified that indeed cytokine stimulation was able to induce epithelial fluidization without compromising epithelial barrier function (FIG. 24D-F). Interestingly, the preferential activation of IL-6 trans-signaling through co-stimulation of IL-6 and the IL-6 soluble receptor (sIL6R) was able to produce a much more robust and sustained phase change in the epithelia (FIG. 24D).

Figure 24N:
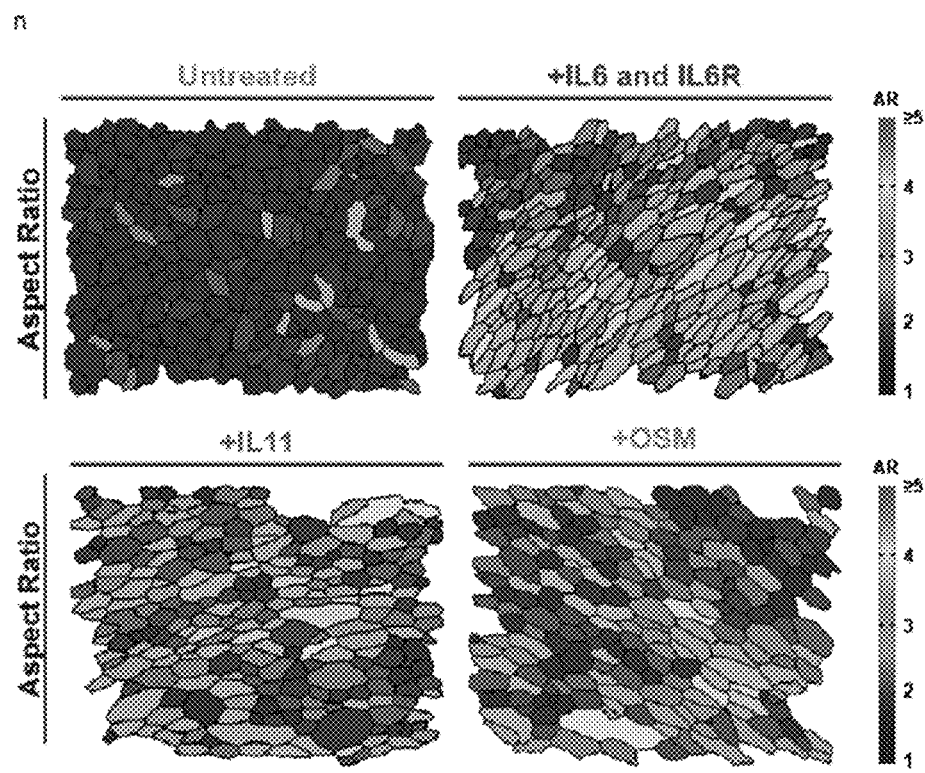
Figure 24O:
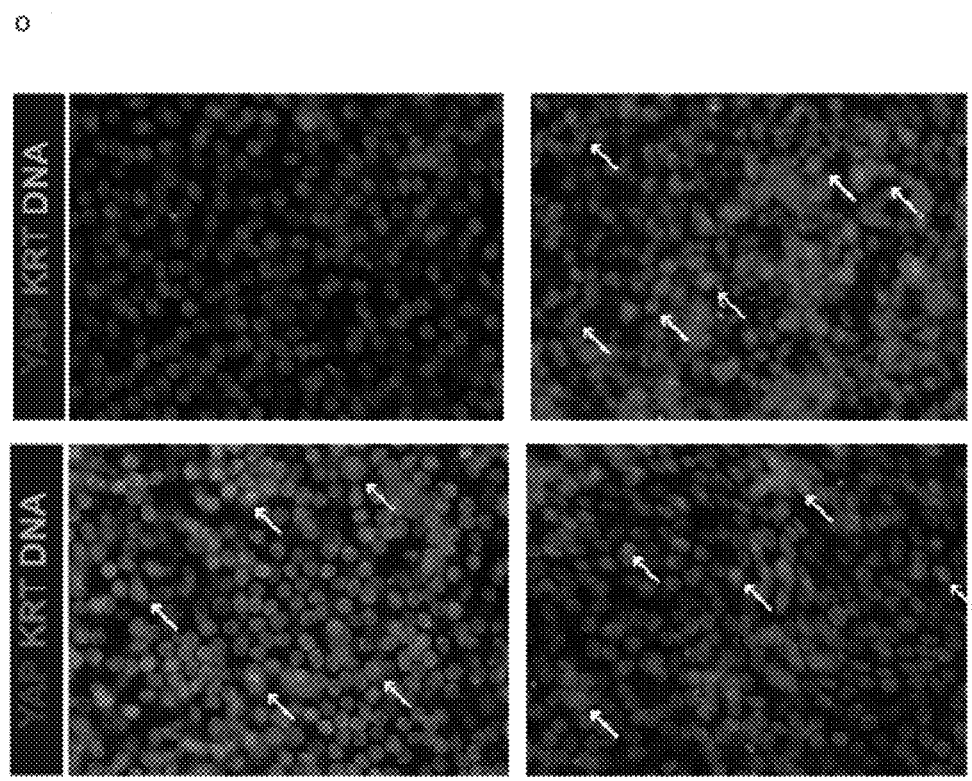

IL-6 family cytokine signaling is canonically viewed through a JAK/STAT lens, whereby receptor activation leads to JAK/STAT phosphorylation and activation. Additionally, JAK/STAT signaling has been implicated in a variety of collective migratory phenomenon across development and disease. As such, we asked if JAK1/2 or STAT3 activation was required for this induced unjammed phase, or if IL-6 family cytokine-related unjamming was similar to other models of induced unjamming in its SRC/YAP-dependency. To test this, we pre-treated proximal cultures with Ruxolitinib (JAK1/2 inhibitor), Stattic (STAT3 inhibitor), Saracatinib (SRC family kinase inhibitor—SFK), or Verteporfin (YAP inhibitor) and subsequently stimulated these cultures with IL-6 family cytokines (FIG. 24H. This treatment scheme surprisingly revealed that JAK/STAT signaling was dispensable for IL-6 family cytokine induced unjamming in proximal cultures, but instead that SRC and YAP were essential for the acquisition of this fluid-like phenotype (FIG. 24I-K). This finding was true when measuring cell dynamics as well as shape (FIG. 24L-N). Additionally, we identified an increase in KRT5+ and YAP nuclear positive cells after IL-6 family cytokine stimulation (FIG. 24O). Together these data indicate that SFK and YAP signaling are regulators of unjamming across multiple models of induced-epithelial dysfunction and that IL-6 family cytokine signaling converges on SRC/YAP activation to achieve epithelial fluidization.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. "About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±10% or 5% of the stated value. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of screening a test compound for induction of an unjammed-to-jammed transition (UJT) in fibrotic primary human bronchial epithelial cells (HBECs) isolated from a subject with a fibrotic lung disease, comprising
culturing the fibrotic primary HBECs at an air-liquid interface for a time sufficient to provide a differentiated pseudostratified epithelium;
contacting the cultured cells with the test compound; and
monitoring the motility of the cultured cells to identify the cultured cells as moving or stationary;
wherein stationary cultured cells indicate that the test compound induces the UJT.

2. The method of claim 1, wherein the test compound decreases expression of MUC5B, inhibits IL-6 expression or activity, inhibits IL-6 signaling pathway, inhibits epidermal growth factor receptor (EGFR) expression or activity, inhibits Yes-associated protein (YAP) expression, inhibits YAP activation, inhibits YAP target gene activation, inhibits SRC expression, or inhibits SRC family kinase expression or activity.

3. The method of claim 1, wherein the fibrotic primary HBECs are isolated from a subject with idiopathic pulmonary fibrosis (IPF), rheumatoid arthritis-associated interstitial lung disease (RA-ILD), chronic hypersensitivity pneumonitis, autoimmune related pulmonary fibrosis, drug-induced pulmonary fibrosis, radiation-induced pulmonary fibrosis, environmental pulmonary fibrosis (hypersensitivity pneumonitis), asbestosis, or occupational fibrosis.

4. The method of claim 2, wherein the fibrotic primary HBECs are isolated from a subject with idiopathic pulmonary fibrosis (IPF), rheumatoid arthritis-associated interstitial lung disease (RA-ILD), chronic hypersensitivity pneumonitis, autoimmune related pulmonary fibrosis, drug-induced pulmonary fibrosis, radiation-induced pulmonary fibrosis, environmental pulmonary fibrosis (hypersensitivity pneumonitis), asbestosis, or occupational fibrosis.

5. The method of claim 1, wherein the HBECs are from less than 2 mm diameter airways.

6. The method of claim 2, wherein the HBECs are from less than 2 mm diameter airways.

7. The method of claim 1, wherein determining if the cultured cells are moving or stationary comprises quantifying a cellular mean-squared displacement (MSD) and an overlap parameter (Q).

8. The method of claim 1, wherein monitoring the cultured cells comprises microscopy, time-lapse imaging microscopy, fluorescence microscopy, multi-photon microscopy, quantitative phase microscopy, surface enhanced Raman spectroscopy, videography, manual visual analysis, automated visual analysis, or traction force microscopy.

9. The method of claim 2, wherein monitoring the cultured cells comprises microscopy, time-lapse imaging microscopy, fluorescence microscopy, multi-photon microscopy, quantitative phase microscopy, surface enhanced Raman spectroscopy, videography, manual visual analysis, automated visual analysis, or traction force microscopy.

10. The method of claim 1, wherein the cultured fibrotic primary HBECs are cultured in a multi-well plate, and a plurality of test compounds or biomarkers are screened or identified.

\* \* \* \* \*